United States Patent
Ogawa et al.

(10) Patent No.: US 8,440,672 B2
(45) Date of Patent: *May 14, 2013

(54) DIPHENYL SUBSTITUTED ALKANES

(75) Inventors: Anthony Ogawa, Mountainside, NJ (US); Feroze Ujjainwalla, Scotch Plains, NJ (US); Ellen K. Vande Bunte, Colts Neck, NJ (US); Lin Chu, Scotch Plains, NJ (US); Debra Ondeyka, Fanwood, NJ (US); Ihor Kopka, Hampton, NJ (US); Bing Li, Towaco, NJ (US); Hyun Ok, Colonia, NJ (US); Minal J. Patel, East Orange, NJ (US); Jinyou Xu, Scotch Plains, NJ (US); Rosemary Sisco, Reading, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 201 days.

This patent is subject to a terminal disclaimer.

(21) Appl. No.: 12/377,136

(22) PCT Filed: Aug. 29, 2007

(86) PCT No.: PCT/US2007/018991
§ 371 (c)(1),
(2), (4) Date: Feb. 11, 2009

(87) PCT Pub. No.: WO2008/030369
PCT Pub. Date: Mar. 13, 2008

(65) Prior Publication Data
US 2010/0168076 A1    Jul. 1, 2010

Related U.S. Application Data

(60) Provisional application No. 60/961,598, filed on Jul. 23, 2007, provisional application No. 60/933,886, filed on Jun. 8, 2007, provisional application No. 60/841,758, filed on Sep. 1, 2006.

(51) Int. Cl.
*A61K 31/506* (2006.01)
*A61K 31/501* (2006.01)
*A61K 31/444* (2006.01)
*C07D 401/14* (2006.01)
*C07D 401/04* (2006.01)

(52) U.S. Cl.
USPC ............. 514/252.03; 514/275; 514/252.02; 514/334; 514/210.02; 544/238; 544/331; 546/257

(58) Field of Classification Search
None
See application file for complete search history.

(56) References Cited

U.S. PATENT DOCUMENTS

| | | | |
|---|---|---|---|
| 4,598,080 | A | 7/1986 | Toth et al. |
| 4,853,398 | A | 8/1989 | Carr et al. |
| 5,668,146 | A | 9/1997 | Brooks et al. |
| 5,795,900 | A | 8/1998 | Brooks et al. |
| 6,051,573 | A | 4/2000 | Clark |
| 6,140,088 | A | 10/2000 | Hanson et al. |
| 6,204,275 | B1 | 3/2001 | Friesen et al. |
| 6,486,331 | B2 | 11/2002 | Hanson et al. |
| 2003/0171544 | A1 | 9/2003 | Riermeier et al. |
| 2004/0053382 | A1 | 3/2004 | Senkpeil et al. |
| 2004/0104937 | A1 | 6/2004 | An |
| 2007/0203147 | A1 | 8/2007 | Coburn et al. |
| 2009/0054435 | A1 | 2/2009 | Imoto |
| 2009/0197883 | A1 | 8/2009 | Armstrong et al. |
| 2009/0258851 | A1* | 10/2009 | Chu et al. ............... 514/210.2 |
| 2010/0168076 | A1 | 7/2010 | Ogawa et al. |
| 2010/0190761 | A1 | 7/2010 | Ogawa et al. |
| 2011/0003815 | A1 | 1/2011 | Ogawa et al. |
| 2011/0034483 | A1 | 2/2011 | Hills et al. |
| 2011/0190346 | A1 | 8/2011 | Chu et al. |

FOREIGN PATENT DOCUMENTS

| | | |
|---|---|---|
| WO | WO97/12865 | 4/1997 |
| WO | WO00/50402 | 8/2000 |
| WO | WO02/33110 | 4/2002 |
| WO | WO02/077789 | 10/2002 |
| WO | WO2005/007672 | 1/2005 |

(Continued)

OTHER PUBLICATIONS

Botteghi et al. in Journal of Organometallic Chemistry (1986), 304(1-2), 217-25 (Abstract and structure).*

(Continued)

*Primary Examiner* — Dennis Heyer
(74) *Attorney, Agent, or Firm* — Maria V. Marucci; Valerie J. Camara

(57) ABSTRACT

The instant invention provides compounds of Formula I which are 5-lipoxygenase activating protein inhibitors. Compounds of Formula (I) are useful as anti-atherosclerotic, anti-asthmatic, anti-allergic, anti-inflammatory and cytoprotective agents.

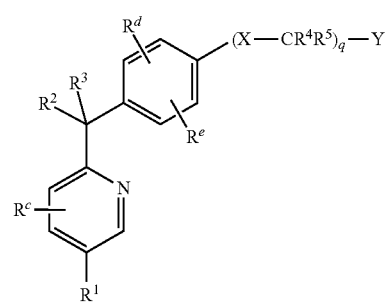

24 Claims, No Drawings

FOREIGN PATENT DOCUMENTS

| | | |
|---|---|---|
| WO | WO2005/009951 A2 | 2/2005 |
| WO | WO2005/097767 | 10/2005 |
| WO | WO2006/044602 | 4/2006 |
| WO | WO2006/044602 A2 | 4/2006 |
| WO | WO2006/098912 | 9/2006 |
| WO | WO2006/098912 A1 | 9/2006 |
| WO | WO 2006/136830 * | 12/2006 |
| WO | WO2007/056210 A2 | 5/2007 |
| WO | WO2007/120574 A2 | 10/2007 |
| WO | WO2008/030369 | 3/2008 |
| WO | WO2008/156721 | 12/2008 |
| WO | WO2009/048547 | 4/2009 |
| WO | WO2009/108550 | 9/2009 |

OTHER PUBLICATIONS

Patani et al. in Chemical Reviews 1996, 96, 3147-3176.*
Evans et al. in Trends on Pharmacological Sciences 29(2), 72-78 (2007).*
Wermuth C. G,. et al—The Practice of Medicinal Chemistry, 1996, p. 203-237.
Charleson, S., et al—Molecular Pharmacology, vol. 41, pp. 873-879, 1992.
Poupaert, J.H.—Encyclopedia of Pharmaceutical Technology, James Swarbrick Ed., 3rd Ed., 2007, p. 1362-1369.
Chabner, B.A. et al.—Goodman & Gilman's: The Pharmacological Basis of Therapeutics, 2006 p. 1315-1403.

* cited by examiner

DIPHENYL SUBSTITUTED ALKANES

CROSS REFERENCE TO RELATED APPLICATIONS

This application is a U.S. National Phase application under 35 U.S.C. §371 of PCT Application No. PCT/US2007/018991, filed Aug. 29, 2007 which claims priority under 35 U.S.C. §119(e) from U.S. Provisional Application Ser. No. 60/961,598, filed Jul. 23, 2007, and from U.S. Provisional Application Ser. No. 60/933,886, filed Jun. 8, 2007, and from U.S. Provisional Application Ser. No. 60/841,758, filed Sep. 1, 2006.

FIELD OF THE INVENTION

The instant invention involves compounds that inhibit 5-lipoxygenase activating protein (FLAP), compositions containing such compounds and methods of treatment using such compounds for the treatment and prevention of atherosclerosis and related diseases and conditions.

BACKGROUND OF THE INVENTION

Inhibition of leukotriene biosynthesis has been an active area of pharmaceutical research for many years. Leukotrienes are potent contractile and inflammatory mediators derived through the oxygenation of arachidonic acid by 5-lipoxygenase.

One class of leukotriene biosynthesis inhibitors are those known to act through inhibition of 5-lipoxygenase (5-LO). In general, 5-LO inhibitors have been sought for the treatment of allergic rhinitis, asthma and inflammatory conditions including arthritis. One example of a 5-LO inhibitor is the marketed drug zileuton, which is indicated for the treatment of asthma. More recently, it has been reported that 5-LO may be an important contributor to the atherogenic process; see Mehrabian, M. et al., Circulation Research, 2002 Jul. 26, 91(2):120-126.

A new class of leukotriene biosynthesis inhibitors (now known as FLAP inhibitors) distinct from 5-LO inhibitors is described in Miller, D. K. et al., "Identification and isolation of a membrane protein necessary for leukotriene production," Nature, vol. 343, No. 6255, pp. 278-281 (18 Jan. 1990). See also Dixon, R. A. et al, "Requirement of a 5-lipoxygenase-activating protein for leukotriene synthesis," Nature, vol 343, no. 6255, pp. 282-4 (18 Jan. 1990). 5-LO inhibitor compounds were used to identify and isolate the inner nuclear membrane 18,000 dalton protein 5-lipoxygenase-activating protein (FLAP). These compounds inhibit the formation of cellular leukotrienes but have no direct effect on soluble 5-LO activity. In cells, arachidonic acid is released from membrane phospholipids by the action of cytosolic phospholipase 2. This arachidonic acid is transferred to nuclear membrane bound 5-lipoxygenase by FLAP. The presence of FLAP in cells is essential for the synthesis of leukotrienes. Additionally, based on studies described in Helgadottir, A., et al., Nature Genetics, Vol 36, No. 3 (March 2004) pp. 233-239, it is believed that the gene encoding 5-lipoxygenase activating protein confers risk for myocardial infarction and stroke in humans.

Despite significant therapeutic advances in the treatment and prevention of atherosclerosis and ensuing atherosclerotic disease events, such as the improvements that have been achieved with HMG-CoA reductase inhibitors, further treatment options are clearly needed. The instant invention addresses that need by providing compounds, compositions and methods for the treatment or prevention of atherosclerosis as well as related conditions.

SUMMARY OF THE INVENTION

The instant invention relates to compounds of Formula I which are FLAP inhibitors, methods for their preparation, and methods and pharmaceutical formulations for using these compounds in mammals, especially humans. This invention provides compounds of structural Formula I:

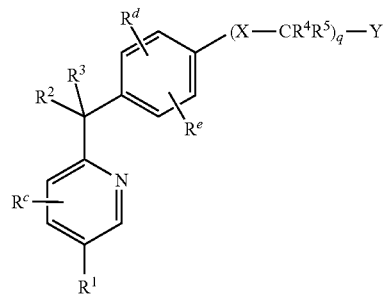

I and the pharmaceutically acceptable salts thereof. This invention also involves the use of compounds described herein to slow or halt atherogenesis. Therefore, one object of the instant invention is to provide a method for treating atherosclerosis, which includes halting or slowing the progression of atherosclerotic disease once it has become clinically evident, comprising administering a therapeutically effective amount of a compound of Formula I to a patient in need of such treatment. Another object is to provide methods for preventing or reducing the risk of developing atherosclerosis and atherosclerotic disease events, comprising administering a prophylactically effective amount of a compound of Formula I to a patient who is at risk of developing atherosclerosis or having an atherosclerotic disease event.

The compounds of Formula I are also useful as anti-asthmatic, anti-allergic, anti-inflammatory and cytoprotective agents. They are also useful in treating angina, cerebral spasm, glomerular nephritis, hepatitis, endotoxemia, uveitis, and allograft rejection. The instant invention provides methods of treatment comprising administering a therapeutically effective amount of a compound of Formula I to a patient in need of the above-described treatments.

A further object is to provide the use of FLAP inhibitors of Formula I in combination with other therapeutically effective agents, including other anti-atherosclerotic drugs. These and other objects will be evident from the description contained herein.

DETAILED DESCRIPTION OF THE INVENTION

The instant invention provides compounds of structural Formula I

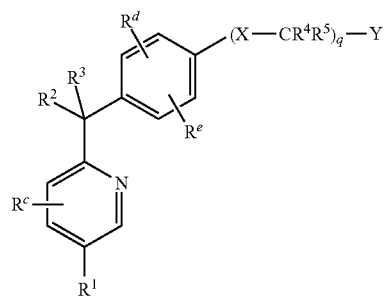

I and the pharmaceutically acceptable salts thereof wherein:
q is an integer selected from 0 (zero) and 1 (one);
$R^1$ is selected from the group consisting of (a) a 5-membered aromatic or partially unsaturated heterocyclic ring containing 2 to 4 heteroatoms selected from N, S and O, wherein the heterocyclic ring is optionally substituted with $R^6$, (b) a 6-membered aromatic or partially unsaturated heterocyclic ring containing 1 to 2 heteroatoms selected from N and O, wherein the heterocyclic ring is optionally substituted with $R^6$;

(c) an 8-membered aromatic or partially unsaturated ortho-fused bicyclic ring system containing 3-5 heteroatoms selected from one sulfur and 2-4 of nitrogen wherein one carbon in the ring is optionally substituted with a group selected from =O, =S, —SMe, —$NH_2$, —$CF_3$, —Cl, —$C_{1-4}$alkyl and $C_{1-4}$alkyl substituted with a group selected from —$NH_2$, —OH, —$OC_{1-4}$alkyl, —CN and 1-3 of fluoro, and (d) a 9-membered aromatic or partially unsaturated ortho-fused bicyclic ring system containing 3-4 nitrogen atoms, wherein one carbon in the ring is optionally substituted with a group selected from =O, =S, —SMe, —$NH_2$, —$CF_3$, —Cl, —$C_{1-4}$alkyl and $C_{1-4}$alkyl substituted with a group selected from —$NH_2$, —OH, —$OC_{1-4}$alkyl, —CN and 1-3 of fluoro;

(e) —$C_{1-6}$alkenyl, and —$C_{2-6}$alkenyl, said alkyl, alkenyl and alkynyl groups being optionally substituted with $R^{12}$ and optionally substituted with $R^{13}$;

(f) —$C_{3-6}$ cycloalkyl optionally substituted with 1-3 substituents selected from the group consisting of fluoro, —$NH_2$, —OH and —$C_{1-3}$alkyl optionally substituted with 1-3 of fluoro;

(g) —O—$R^{6a}$ wherein $R^{6a}$ is selected from the group consisting of (1) —$C_{1-6}$alkyl optionally substituted with $R^{12}$ and optionally substituted with $R^{13}$, (2) —$C_{3-6}$ cycloalkyl optionally substituted with $R^{12}$ and optionally substituted with $R^{13}$ and (3) —$C_{2-6}$alkyl-$R^{10}$; with the proviso that when q is 0, $R^{6a}$ is not —$C_{1-6}$alkyl substituted with $Z^1$; and (h) —H, —OH, —CN, —$CO_2R^{4a}$, —$C(O)NR^7R^8$, —$NR^7R^8$, —$NR^bSO_pR^a$, —$NR^bC(O)R^a$, —$NR^bC(O)NR^aR^b$, —$S(O)_pR^a$, and —$S(O)_pNR^aR^b$;

p is an integer selected from 0, 1 and 2;

$R^2$ is selected from the group consisting of (a) —$C_{1-6}$alkyl optionally substituted with one or more substituents selected from the group consisting of —OH and fluoro (for example, 1-3 of fluoro), (b) —$C_{3-6}$ cycloalkyl optionally substituted with 1-3 of fluoro, and

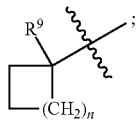

(c)

n is an integer selected from 0, 1, 2 and 3;

$R^3$ is selected from the group consisting of —H, —F, —OH, and —$C_{1-3}$alkyl optionally substituted with 1-5 fluoro (including for example —$CF_3$); or $R^2$ and $R^3$ are taken in combination and represent a mono- or bi-cyclic ring system containing 3 to 8 carbon atoms, said system being optionally substituted with 1-2 groups selected from: $C_{1-3}$alkyl, $OC_{1-3}$ alkyl, F, OH, mono-, di- or tri-fluoro$C_{1-3}$alkyl and mono-, di- and tri-fluoro$C_{1-3}$ alkoxy;

X is selected from the group consisting of —O—, —S— and —$C(R^{14})_2$—;

$R^{4a}$ is selected from the group consisting of —H, —$C_{1-6}$alkyl and —$C_{3-6}$ cycloalkyl;

$R^4$ is selected from the group consisting of —H, —$C_{1-6}$alkyl and —$C_{3-6}$ cycloalkyl;

$R^5$ is selected from the group consisting of —H, —F, and —$CH_3$;

$R^6$ is selected from the group consisting of (a) —$C_{1-6}$alkenyl optionally substituted with one or more substituents selected from the group consisting of —OH, —$NH_2$, —CN, —O—$C_{1-4}$alkyl and fluoro (for example, 1-3 of fluoro), (b) —$C_{1-6}$alkyl-$R^{10}$, (c) —$OC_{1-6}$alkyl optionally substituted with one or more substituents selected from the group consisting of —OH, —$NH_2$ and fluoro, (d) —$C_{3-6}$ cycloalkyl optionally substituted with one or more substituents selected from the group consisting of methyl, —OH, —$NH_2$, —$CF_3$ and fluoro, (e) —$NR^7R^8$, (f) —$SO_2C_{1-3}$alkyl, (g) —$CO_2$—$R^8$, (h) —OH, (i) =O (oxo), —SH, (k) =S, (l) —SMe, (m) —Cl, (n) —$CF_3$, (o)—CN and (p) $R^{10}$;

$R^7$ is selected from the group consisting of (a) —H, (b) —$C_{1-6}$alkyl optionally substituted with one or more substituents selected from the group consisting of —F, —$NH_2$ and —OH, (c) —$C_{3-6}$ cycloalkyl optionally substituted with one or more substituents selected from the group consisting of methyl, —$CF_3$, —F, —$NH_2$ and —OH, (d) —$COC_{1-6}$alkyl optionally substituted with one or more substituents selected from the group consisting of —F and —OH, (e) —$COC_{3-6}$cycloalkyl optionally substituted with one or more substituents selected from the group consisting of methyl, —$CF_3$, —F, —$NH_2$ and —OH, and (f) a 4-6 membered saturated heterocyclic ring containing one N, wherein the ring is bonded to the nitrogen in —$NR^7R^8$ through a carbon atom in the ring, and wherein the ring is optionally substituted with one or more substituents selected from the group consisting of methyl, —$CF_3$, —F, —$NH_2$ and —OH;

$R^8$ is selected from the group consisting of (a) —H, (b) —$C_{1-6}$alkyl optionally substituted with one or more substituents selected from the group consisting of —F, —$NH_2$ and —OH, and (c) —$C_{3-6}$cycloalkyl optionally substituted with one or more substituents selected from the group consisting of methyl, —$CF_3$, —F, —$NH_2$ and —OH;

$R^9$ is selected from the group consisting of —H, —OH, —$C_{1-3}$alkyl and —F;

$R^{10}$ is a heterocyclic ring selected from the group consisting of (a) azetidinyl optionally substituted with one or more of methyl, —F and —OH, (b) pyrrolidinyl optionally substituted with one or more of methyl, —F and —OH, (c) piperidinyl optionally substituted with one or more of methyl, —F and —OH and (d) morpholinyl optionally substituted with one or more of methyl, —F and —OH; and Y is selected from the group consisting of (a) a 5-membered aromatic or partially unsaturated heterocyclic ring containing 1 to 4 heteroatoms selected from 1 to 4 of N and zero to 1 of S, wherein the heterocyclic ring is optionally substituted with $R^{11}$, (b) a 6-membered aromatic or partially unsaturated heterocyclic ring containing 1 to 2 N heteroatoms, wherein the heterocyclic ring is optionally substituted with $R^{11}$, (c) a 9-membered bicyclic aromatic or partially unsaturated heterocyclic ring containing 1 to 4 N heteroatoms, wherein the heterocyclic ring is optionally substituted with $R^{11}$ and (d) a 10-membered bicyclic aromatic or partially unsaturated heterocyclic ring containing 1 to 4 N heteroatoms, wherein the heterocyclic'ring is optionally substituted with $R^{11}$; and $R^{11}$ is selected from the group consisting of —F, —$NH_2$, —OH, —$OC_{3-4}$cycloalkyl, —$C_{1-3}$alkyl optionally substituted with 1-3 fluoro, and —$OC_{1-3}$alkyl optionally substituted with phenyl or 1-3 fluoro.

$R^{12}$ is selected from the group consisting of: —$CO_2R^{4a}$, —$C(O)NR^7R^8$, —$N(R^a)_2$, —$NR^bSO_pR^a$, —$NR^bC(O)R^a$, —$NR^bC(O)NR^aR^b$, —$S(O)_pNR^aR^b$, —$S(O)_pR^a$, —F, —$CF_3$, phenyl, Hetcy and $Z^1$, $R^{13}$ is selected from the group consisting of —OH, —$NH_2$ and 1-5 of —F;

$R^{14}$ is selected from the group consisting of —H and —$C_{1-4}$alkyl optionally substituted with 1-3 fluoro groups;

each $R^a$ is independently selected from the group consisting of
a) —H,
b) —$C_{1-4}$alkyl, —$C_{2-4}$alkenyl and —$C_{2-4}$alkynyl, wherein each is optionally substituted with 1-2 substituents selected from the group consisting of: —OH, —$OC_{1-4}$alkyl, —CN, —$NH_2$, —$NHC_{1-4}$alkyl, and —$N(C_{1-4}$alkyl$)_2$, and —$CF_3$, and optionally with 1-3 of fluoro,
c) Hetcy and Hetcy-$C_{1-4}$alkyl-, the Hetcy moieties being optionally substituted on carbon with 1-2 substituents selected from the group consisting of —F, —OH, —$CO_2H$, —$C_{1-4}$alkyl, —$CO_2C_{1-4}$alkyl, —$OC_{1-4}$alkyl, —$NH_2$, —$NHC_{1-4}$alkyl, —$N(C_{1-4}$alkyl$)_2$, —NHC(O)$C_{1-4}$alkyl, oxo, —$C(O)NHC_{1-4}$alkyl and —$C(O)N(C_{1-4}$alkyl$)_2$; and optionally substituted on nitrogen when present with a group selected from —$C_{1-4}$alkyl and —$C_{1-4}$acyl; and the alkyl portion of Hetcy-$C_{1-4}$alkyl- being optionally substituted with a member selected from the group consisting of —OH, —CN, —$OC_{1-4}$alkyl, —$NH_2$, —$NHC_{1-4}$-alkyl, —$N(C_{1-4}$alkyl$)_2$ and 1-3 of fluoro,
d) $Z^2$ and $Z^2$—$C_{1-4}$alkyl-, the alkyl portion of $Z^2$—$C_{1-4}$alkyl- being optionally substituted with a substituent selected from the group consisting of —OH, —CN, —$OC_{1-4}$alkyl, —$NH_2$, —$NHC_{1-4}$alkyl, —$N(C_{1-4}$alkyl$)_2$ and 1-3 of fluoro;

each $R^b$ is independently selected from the group consisting of —H and —$C_{1-3}$alkyl optionally substituted with 1-2 members selected from the group consisting of $NH_2$, —OH, —F, —CN and —$CF_3$;

$R^c$, $R^d$, and $R^e$ are each independently selected from —H, —F, —Cl, —OH, —CN, —$C_{1-4}$alkyl optionally substituted with 1-3 of fluoro, and —$OC_{1-4}$alkyl optionally substituted with 1-3 of fluoro;

Hetcy is selected from the group consisting of azetidinyl, pyrrolidinyl, piperidinyl, piperazinyl, morpholinyl, tetrahydrofuranyl and β-lactamyl, δ-lactamyl, γ-lactamyl and tetrahydropyranyl;

$Z^1$ is selected from the group consisting of:
a) $Z^2$,
b) an 8-membered aromatic or partially unsaturated ortho-fused bicyclic ring system containing 3-5 heteroatoms selected from one sulfur and 2-4 of nitrogen wherein one carbon in the ring is optionally substituted with a group selected from =O, =S, —SMe, —$NH_2$, —$CF_3$, —Cl, —$C_{1-4}$alkyl and $C_{1-4}$alkyl substituted with a group selected from —$NH_2$, —OH, —CN and 1-3 of fluoro, and
c) a 9-membered aromatic or partially unsaturated ortho-fused bicyclic ring system containing 3-4 nitrogen atoms, wherein one carbon in the ring is optionally substituted with a group selected from =O, =S, —SMe, —$NH_2$, —$CF_3$, —$C_{1-4}$alkyl and $C_{1-4}$alkyl substituted with a group selected from —$NH_2$, —OH, —$OC_{1-4}$alkyl, —CN and 1-3 of fluoro; and $Z^2$ is selected from the group consisting of:
a) a 5-membered aromatic or partially unsaturated heterocyclic ring containing 2-4 nitrogen atoms, wherein one nitrogen in the ring is optionally substituted with a group selected from —$C_{1-4}$alkyl and —$C_{1-4}$alkyl substituted with a group selected from —$NH_2$, —OH, —CN and 1-3 of fluoro, and one carbon in the ring is optionally substituted with a group selected from =O, =S, —SMe, —$CF_3$, —Cl, —$C_{1-4}$alkyl and —$C_{1-4}$alkyl substituted with a group selected from —$NH_2$, —OH, —$OC_{1-4}$alkyl, —CN and 1-3 of fluoro,
b) a 5-membered aromatic or partially unsaturated heterocyclic ring containing 2-3 heteroatoms selected from one oxygen or one sulfur and 1-2 of nitrogen, wherein one nitrogen in the ring is optionally substituted with a group selected from $C_{1-4}$alkyl and $C_{1-4}$alkyl substituted with a group selected from —$NH_2$, —OH, —CN and 1-3 of fluoro, and one carbon in the ring is optionally substituted with a group selected from =O, —SMe, —$CF_3$, —Cl, and $C_{1-4}$alkyl optionally substituted with a group selected from —$NH_2$, —OH, —$OC_{1-4}$alkyl, —CN and 1-3 of fluoro, and
c) a 6-membered aromatic or partially unsaturated heterocyclic ring containing 1-2 nitrogen atoms, wherein one nitrogen in the ring is optionally substituted with a group selected from —$C_{1-4}$alkyl and —$C_{1-4}$alkyl substituted with a group selected from –$NH_2$, —OH, —CN and 1-3 of fluoro, and one carbon in the ring is optionally substituted with a group selected from =O, =S, —SMe, —$NH_2$, —$CF_3$, —Cl, —$C_{1-4}$alkyl and —$C_{1-4}$alkyl substituted with a group selected from —$NH_2$, —OH, —$OC_{1-4}$alkyl, —CN and 1-3 of fluoro.

Another embodiment of this invention includes compounds having the following structural Formula Ia:

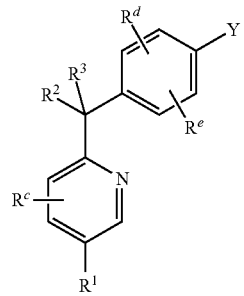

Ia and the pharmaceutically acceptable salts thereof, wherein the variables ($R^1$, Y, etc.) are as defined in Formula I. Still another embodiment of this invention includes compounds having the following structural Formula Ib:

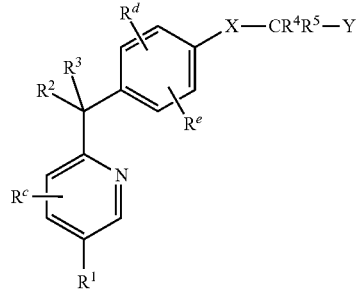

Ib and the pharmaceutically acceptable salts thereof, wherein the variables ($R^1$, Y, etc.) are as defined in Formula I.

An additional embodiment of this invention includes compounds falling within the scope of Formula I and Ia having structural Formula Ia-1:

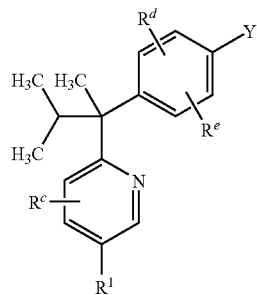

Ia-1 and the pharmaceutically acceptable salts thereof, wherein the variables ($R^1$, Y, etc.) are as defined in Formula I. Yet another embodiment of this invention includes compounds falling within the scope of Formula I and Ib having structural Formula Ib-1:

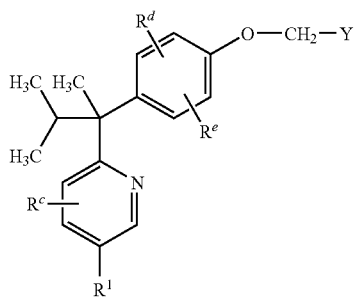

Ib-1 and the pharmaceutically acceptable salts thereof, wherein the variables ($R^1$, Y, etc.) are as defined in Formula I.

Within each of the embodiments defined by Formula I, Ia and Ia-1 is a first class of compounds wherein Y is a 6-membered aromatic heterocyclic ring containing 1 to 2 N heteroatoms wherein the heterocyclic ring is optionally substituted with $R^{11}$. In a first sub-class of each first class are compounds wherein Y is selected from:

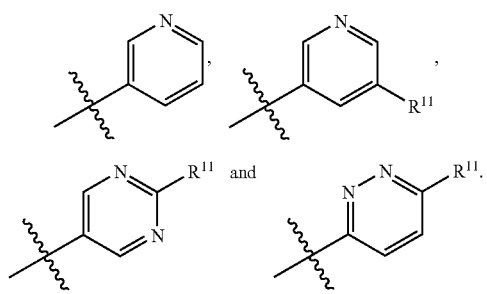

In a second subclass within each first class, Y is selected from:

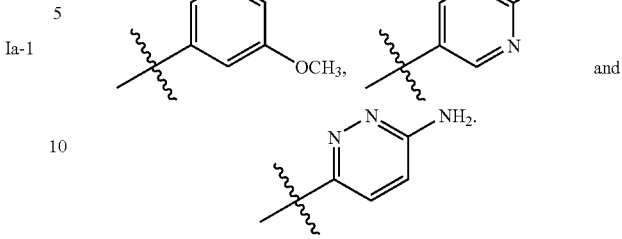

Within each of the embodiments defined by Formula I, Ia and Ia-1, as well as within each of the first classes and first sub-classes thereof, is a second class of compounds wherein $R^{11}$, when present, is selected from the group consisting of —$NH_2$ and —$OC_{1-3}$alkyl optionally substituted with phenyl or 1-3 of fluoro.

Within each of the embodiments defined by Formula I, Ib and Ib-1 is a third class of compounds wherein Y is selected from (a) a 5-membered aromatic heterocyclic ring containing 1 to 2 heteroatoms selected from 1 to 2 of N and zero to 1 of S, wherein the heterocyclic ring is optionally substituted with $R^{11}$, and (b) a 6-membered aromatic heterocyclic ring containing 1 to 2 N heteroatoms, wherein the heterocyclic ring is optionally substituted with $R^{11}$. In a sub-class of each third class are compounds wherein Y is selected from:

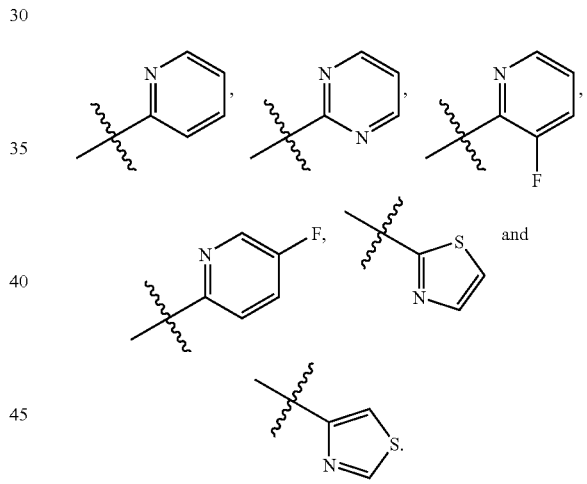

In another sub-class of each third class of compounds are those wherein Y is a 6-membered aromatic heterocyclic ring containing 1 to 2 N heteroatoms, wherein the heterocyclic ring is optionally substituted with $R^{11}$, and in a further sub-class, Y is selected from:

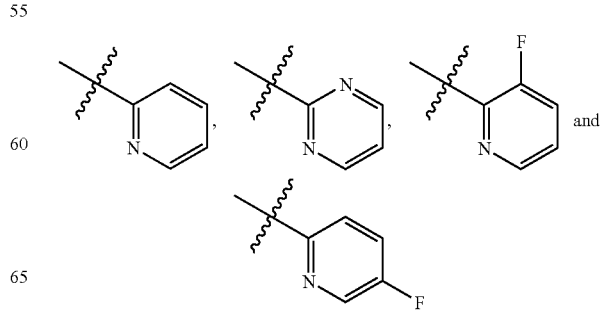

In still another sub-class of each third class of compounds are those wherein Y is a 5-membered aromatic or partially unsaturated heterocyclic ring containing one N and one S, and in a further sub-class, Y is selected from:

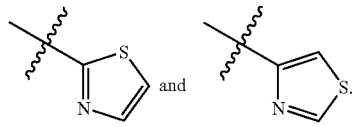 [SMILES: *c1nccs1 ; *c1cscn1]

Within each of the embodiments defined by Formula I, Ib and Ib-1, as well as within the third classes and sub-classes thereof defined above, is a fourth class of compounds wherein $R^{11}$ is —F or is absent (i.e., Y is unsubstituted).

Within the embodiments defined by Formula I, Ia and Ib, as well as within each of the first, second, third and fourth classes and in each of any sub-classes thereof, is a fifth class of compounds wherein $R^2$ is selected from the group consisting of i-propyl, t-butyl, cyclopropyl, cyclobutyl,

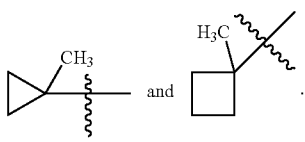

In a sub-class of each fifth class of compounds are those wherein $R^2$ is selected from i-propyl and t-butyl.

Within the embodiments defined by Formula I, Ia and Ib, as well as within each of the first, second, third, fourth and fifth classes and in each of any sub-classes thereof, is a sixth class of compounds wherein $R^3$ is selected from the group consisting of —H and —CH$_3$. In a further sub-class thereof are compounds wherein $R^3$ is —H when $R^2$ is t-butyl; and $R^3$ is —CH$_3$ when $R^2$ is i-propyl.

Within the embodiment defined by Formula I as well as within each of the first through sixth classes and in each of any sub-classes thereof, and the embodiment defined by Formula Ib as well as within each of the third through sixth classes and in each of any sub-classes thereof, is a seventh class of compounds wherein $R^4$ is selected from the group consisting of —H, —CH$_3$ and —CH$_2$CH$_3$.

Within the embodiment defined by Formula I as well as within each of the first through seventh classes and in each of any sub-classes thereof, and the embodiment defined by Formula Ib as well as within each of the third through seventh classes and in each of any sub-classes thereof, is an eighth class of compounds wherein $R^5$ is —H.

Within each of the embodiments defined by Formula I, Ia, Ib, Ia-1 and Ib-1, as well as within each of the first through eighth classes and sub-classes that are associated with any of Formula I, Ia, Ib, Ia-1 and Ib-1, is a ninth class of compounds wherein $R^c$, $R^d$ and $R^e$ are each —H.

Within each of the embodiments defined by Formula I, Ia, Ib, Ia-1 and Ib-1, as well as within each of the first through ninth classes and sub-classes that are associated with any of Formula I, Ia, Ib, Ia-1 and Ib-1, is a tenth class of compounds wherein $R^1$ is selected from the group consisting of:
(a) a 5-membered aromatic or partially unsaturated heterocyclic ring containing a total of 2 to 4 heteroatoms selected from two to four of N, zero to one of O, and zero to one of S, wherein the heterocyclic ring is optionally substituted with $R^6$,
(b) a 6-membered aromatic or partially unsaturated heterocyclic ring containing 1 to 2 heteroatoms selected from N and O, wherein the heterocyclic ring is optionally substituted with $R^6$,
(c) —C$_{1-4}$alkyl optionally substituted with $R^{12}$, and particularly wherein $R^{12}$ is selected from Hetcy and $Z^1$, and optionally substituted with $R^{13}$, and particularly wherein $R^{13}$ is selected from —OH and —NH$_2$,
(d) —OR$^{6a}$ wherein R$^{6a}$ is —C$_{1-4}$ alkyl optionally substituted with $R^{13}$, and particularly wherein $R^{13}$ is 1-5 of fluoro,
(e) —CO$_2$C$_{1-6}$alkyl,
(f) —C(O)NR$^7$R$^8$,
(g) —CN, and
(h) —C$_{3-6}$ cycloalkyl optionally substituted with $R^{12}$, and particularly wherein $R^{12}$ is selected from Hetcy and $Z^1$, and optionally substituted with $R^{13}$, and particularly wherein $R^{13}$ is selected from —OH and —NH$_2$.

In a first sub-class of each tenth class are compounds wherein $R^1$ is a 5-membered aromatic or partially unsaturated heterocyclic ring containing a total of 2 to 4 heteroatoms selected from two to four of N, zero to one of O, and zero to one of S, wherein the heterocyclic ring is optionally substituted with $R^6$, and particularly wherein $R^1$ is selected from:

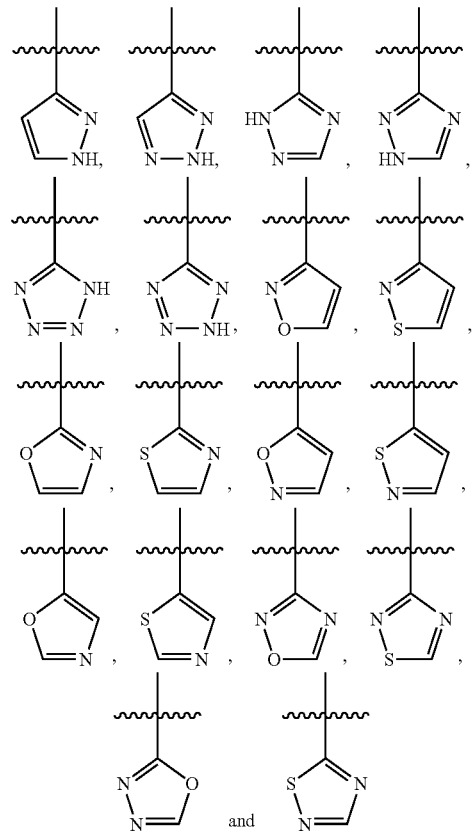

and is optionally substituted with $R^6$.

In second sub-class of each tenth class are compounds wherein $R^1$ is a 6-membered aromatic heterocyclic ring containing 1 to 2N heteroatoms, wherein the heterocyclic ring is optionally substituted with $R^6$, and particularly wherein $R^1$ is selected from:

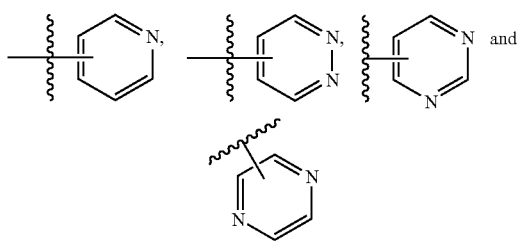

and is optionally substituted with $R^6$.

In a third sub-class of each tenth class are compounds wherein $R^1$ is selected from
(a) —C(CH$_3$)$_2$OH, (b) —C(CH$_3$)$_2$NH$_2$ (c) cycloalkyl optionally substituted with one or more substituents selected from the group consisting of —OH and —NH$_2$, (d) —OCH$_3$ optionally substituted with 1-3 of fluoro, (e) —CN, (f) —CO$_2$C$_{1-6}$alkyl, and (g) —C(O)NR$^7$R$^8$ wherein R$^8$ is —H and R$^7$ is selected from (i) —H, (ii) —C$_{1-6}$alkyl optionally substituted with one or more substituents selected from the group consisting of —F and —OH, (iii) cycloalkyl optionally substituted with one or more substituents selected from the group consisting of —F and —OH, and (iv) a 4-6 membered saturated heterocyclic ring containing one N, wherein the ring is bonded to the nitrogen in —NR$^7$R$^8$ through a carbon atom in the ring, e.g., where R$^8$ is —H and R$^7$ is a 6-membered saturated heterocyclic ring, then —NR$^7$R$^8$ represents

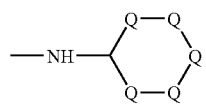

wherein one Q represents —NH— and the remaining Q's represent —CH$_2$—,
and wherein the saturated heterocyclic ring is optionally substituted with one or more substituents selected from the group consisting of methyl, —CF$_3$, —F, —NH$_2$ and —OH.

Within each of the embodiments defined by Formula I, Ia, Ib, Ia-1 and Ib-1, as well as within each of the first through tenth classes and sub-classes associated with any of Formula I, Ia, Ib, Ia-1 and Ib-1, is an eleventh class of compounds wherein R$^6$, when present, is selected from the group consisting of
(a) —CR$^x$R$^y$R$^z$ wherein R$^x$ is selected from —H, —C$_{1-3}$alkyl and —F, R$^y$ is selected from —H, —C$_{1-3}$alkyl and —F, and R$^z$ is selected from —H, —C$_{1-3}$alkyl, —OC$_{1-3}$alkyl, —F, —NH$_2$ and —OH; or R$^x$ and R$^y$ are joined together with the carbon to which they are attached to form a cyclopropyl ring having the following structure

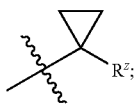

(b) —C$_{1-3}$alkyl-R$^{10}$,
(c) —R$^{10}$,
(d) —OC$_{1-4}$alkyl optionally substituted with 1-5 fluoro,
(e) —NR$^7$R$^8$,
(f) —SO$_2$CH$_3$,
(g) oxo and
(h) —CO$_2$C$_{1-6}$alkyl.

In a sub-class of each eleventh class of compounds are those wherein $R^6$ is from the group consisting of —C(CH$_3$)$_2$OH, —C(CH$_3$)$_2$NH$_2$, —CH$_2$OH,

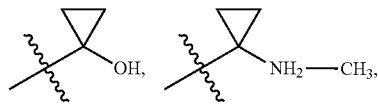 [SMILES: *C1(O)CC1 ; *C1(NC)CC1]

—CF$_3$, —CH$_2$—R$^{10}$, —CH(CH$_3$)—R$^{10}$, —C(CH$_3$)$_2$—R$^{10}$, —SO$_2$CH$_3$, and —NR$^7$R$^8$ wherein R$^7$ is selected from —H and —C$_{1-3}$alkyl, and R$^8$ is selected from —H, —C$_{1-3}$alkyl, and a 4-6 membered saturated heterocyclic ring containing one N, wherein the ring is bonded to the nitrogen in —NR$^7$R$^8$ through a carbon atom in the ring, and wherein the ring is optionally substituted with one or more substituents selected from the group consisting of methyl, —CF$_3$, —F, —NH$_2$ and —OH.

Within each of the embodiments defined by Formula I, Ia, Ib, Ia-1 and Ib-1, as well as within each of the first through eleventh classes and sub-classes associated with any of Formula I, Ia, Ib, Ia-1 and Ib-1, is a twelfth class of compounds wherein R$^{10}$ is selected from

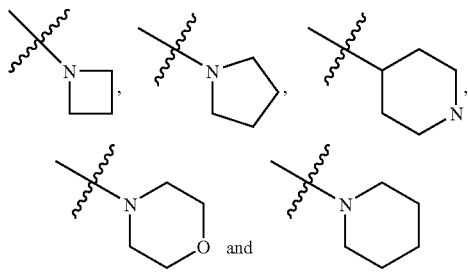

and is optionally substituted with a substituent selected from —OH and 1-2 of fluoro.

Within each of the embodiments defined by Formula I, Ia, Ib, Ia-1 and Ib-1, as well as within each of the first through tenth classes and sub-classes associated with any of Formula I, Ia, Ib, Ia-1 and Ib-1, is a thirteenth class of compounds wherein R$^{12}$, when present, is Hetcy. In a further sub-class thereof are compounds wherein R$^{12}$ is absent.

Within each of the embodiments defined by Formula I, Ia, Ib, Ia-1 and Ib-1, as well as within each of the first through tenth and thirteenth classes and sub-classes associated with any of Formula I, Ia, Ib, Ia-1 and Ib-1, is a fourteenth class of compounds wherein R$^{13}$, when present, is —OH. In a further sub-class thereof, R$^{12}$ is absent and R$^{13}$ is —OH or is absent.

The term "alkyl" means carbon chains which may be linear or branched, or combinations thereof, containing the indicated number of carbon atoms. Examples of alkyl groups include methyl, ethyl, propyl, iso-propyl (i-propyl), butyl, sec- and tert-butyl (s-butyl, t-butyl), pentyl, hexyl; and the like. "Cycloalkyl" is intended to be a cyclized alkyl ring having the indicated number of carbon atoms Examples of cycloalkyl include cyclopropyl, cyclobutyl, cyclopentyl, and cyclohexyl. The cycloalkyl ring may be substituted on any available carbon which results in the creation of a stable structure, including the ring carbon which serves as the point of attachment to the rest of the molecule. Preferably, cycloalkyl is cyclopropyl or cyclobutyl, and more particularly, when it is substituted with —CH$_3$ or —CF$_3$, the substituent is on the ring carbon which serves as the point of attachment to the rest of the molecule.

The terms "heterocycle" and derivatives thereof such as "heterocyclyl" and "heterocyclic ring" mean an aromatic, partially unsaturated or saturated ring containing one or more carbon atoms and one or more heteroatoms such as nitrogen, oxygen and sulfur, but may be more specifically defined where appropriate in the specification, for example with respect to degree of saturation, number of members (i.e. atoms) in the ring and/or the type and quantity of heteroatoms in the ring. The point of attachment in a compound structure may be via any carbon or nitrogen in the heterocyclic ring which results in the creation of a stable structure, unless specified otherwise. The heterocyclic ring may be substituted on any available carbon or nitrogen in the ring which results in the creation of a stable structure, unless specified otherwise.

The phrase "optionally substituted with one or more substituents" is intended to mean that the total number of substituents on the optionally substituted moiety overall may be zero, one or more than one, and that each carbon and heteroatom (when present) available for substitution in the given moiety may independently be unsubstituted or mono- or poly-substituted, with one or more substituents that are the same or different at each occurrence and which result in the creation of a stable structure. The term "poly-substituted" is intended to mean two or more substituents, e.g. di-, tri-, tetra-, penta-substitution and higher as appropriate, valence and stability permitting. For example, $C_{1-3}$ alkyl optionally substituted with one or more of fluoro includes, but is not limited to, —$CH_3$, —$CH_2F$, —$CHF_2$, —$CF_3$, —$CH_2CH_3$, —$CH_2$—$CH_2F$, —$CHF$—$CH_2F$, —$CF_2$—$CF_3$, —$CH(CF_3)$—$CH_3$, —$CF_2$—$CF_2$—$CF_3$, and the like. In some instances, the number of substituents which may optionally be present on a moiety is specified, for example but not limited to, 1-3 of —F (fluoro). For example, methyl optionally substituted with 1-3 of —F includes —$CH_3$, —$CH_2F$, —$CHF_2$ and —$CF_3$.

Some of the compounds encompassed herein may exist as tautomers, e.g., keto-enol tautomers. For the purpose of illustration, when $R^1$ is a 5-membered heterocyclic ring and $R^6$ is oxo, the resulting compound may be capable of tautomerism, as exemplified below:

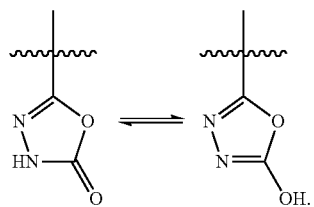 [SMILES: *c1n[nH]c(=O)o1 ; *c1nnc(O)o1]

Where compounds of this invention are capable of tautomerization, all individual tautomers as well as mixtures thereof are included in the scope of this invention.

Reference to the compounds of this invention as those of "Formula I" "Formula Ia," "Formula Ib," or any other generic structural formulas used herein is intended to encompass compounds falling within the scope of the structural Formula including pharmaceutically acceptable salts, esters and solvates thereof where such forms are possible, unless specified otherwise. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particular examples are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like, and particularly citric, fumaric, hydrobromic, hydrochloric, trifluoroacetic, maleic, phosphoric, sulfuric, and tartaric acids.

Pharmaceutically acceptable esters can optionally be made by esterification of an available carboxylic acid group or by formation of an ester on an available hydroxy group in a compound. Such esterified compounds may serve as prodrugs which can be hydrolyzed back to their acid or hydroxy form. Examples of pharmaceutically acceptable esters include, but are not limited to; —$C_{1-4}$ alkyl and —$C_{1-4}$ alkyl substituted with phenyl.

The compounds of Formula I may contain one or more asymmetric centers, and can thus occur as racemates, racemic (i.e., enantiomeric) mixtures, single enantiomers, diastereoisomeric mixtures and individual diastereoisomers. The present invention includes all such isomers, as well as salts, esters and solvates of such racemates, mixtures, enantiomers and diastereoisomers. Furthermore, some of the crystalline forms of compounds of the present invention may exist as polymorphs and as such are intended to be included in the present invention. In addition, some of the compounds of the instant invention may form solvates with water or common organic solvents. Such solvates and hydrates are likewise encompassed within the scope of this invention.

Compounds of structural Formula I or intermediates may be separated into their individual enantiomers or diastereoisomers by, e.g., fractional crystallization from suitable solvents, e.g., DCM/hexanes or EtOAc/hexanes, or via chiral chromatography using an optically active stationary phase. Absolute stereochemistry may be determined by X-ray crystallography of crystalline products or crystalline intermediates which are derivatized, if necessary, with a reagent containing a stereogenic center of known configuration.

The ability of the compounds of this invention to inhibit biosynthesis of the leukotrienes makes them useful for preventing or reversing the symptoms induced by the leukotrienes in a human subject. Accordingly, this invention provides a method for preventing the synthesis, the action, or the release of leukotrienes in a mammal which comprises administering to said mammal a FLAP inhibitory effective amount of a compound of this invention. Such FLAP inhibitory activity can be measured using the FLAP Assay described herein. Since leukotrienes are potent inflammatory mediators, also provided is method of treating an inflammatory condition in a mammal which comprises administering a therapeutically effective amount of a compound of this invention to a mammal in need of such treatment.

The inhibition of the mammalian biosynthesis of leukotrienes also indicates that the compounds and pharmaceutical compositions thereof are useful to treat, prevent or ameliorate atherosclerosis in mammals, and especially in humans. Therefore, the compounds of Formula I can be used for the treatment of atherosclerosis comprising administering a therapeutically effective amount of a compound of Formula I to a patient in need of such treatment. A further aspect of this invention involves a method for preventing or reducing the risk of developing atherosclerosis, comprising administering a prophylactically effective amount of a compound of Formula I to a patient in need of such treatment, for example, a patient who is at risk of developing atherosclerosis.

Atherosclerosis is characterized by the deposition of atheromatous plaques containing cholesterol and lipids on the innermost layer of the walls of large and medium-sized arteries. Atherosclerosis encompasses vascular diseases and conditions that are recognized and understood by physicians practicing in the relevant fields of medicine. Atherosclerotic cardiovascular disease including restenosis following revascularization procedures, coronary heart disease (also known as coronary artery disease or ischemic heart disease), cerebrovascular disease including multi-infarct dementia, and peripheral vessel disease including erectile dysfunction, are all clinical manifestations of atherosclerosis and are therefore encompassed by the terms "atherosclerosis" and "atherosclerotic disease."

A FLAP inhibitor of this invention may be administered to prevent or reduce the risk of occurrence, or recurrence where the potential exists, of a coronary heart disease (CHD) event, a cerebrovascular event, and/or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists.

Accordingly, the instant invention also provides a method for preventing or reducing the risk of a first or subsequent occurrence of an atherosclerotic disease event comprising the administration of a prophylactically effective amount of a FLAP inhibitor of Formula I to a patient at risk for such an event. The patient may already have atherosclerotic disease at the time of administration, or may be at risk for developing it.

The method of this invention particularly serves to prevent or slow new atherosclerotic lesion or plaque formation, and to prevent or slow progression of existing lesions or plaques, as well as to cause regression of existing lesions or plaques. Accordingly, one aspect of this invention encompassed within the scope of treatment of atherosclerosis involves a method for halting or slowing the progression of atherosclerosis, including halting or slowing atherosclerotic plaque progression, comprising administering a therapeutically effective amount of a FLAP inhibitor of Formula I to a patient in need of such treatment. This method also includes halting or slowing progression of atherosclerotic plaques existing at the time the instant treatment is begun (i.e., "existing atherosclerotic plaques"), as well as halting or slowing formation of new atherosclerotic plaques in patients with atherosclerosis.

Another aspect of this invention encompassed within the scope of treatment of atherosclerosis involves a method for regression of atherosclerosis, including regression of atherosclerotic plaques existing at the time the instant treatment is begun, comprising administering a therapeutically effective amount of a FLAP inhibitor of Formula I to a patient in need of such treatment. Another aspect of this invention involves a method for preventing or reducing the risk of atherosclerotic plaque rupture comprising administering a prophylactically effective amount of a FLAP inhibitor of Formula I to a patient in need of such treatment.

The ability of the compounds of Formula I to inhibit biosynthesis of the leukotrienes makes them useful for preventing or reversing the symptoms induced by the leukotrienes in a human subject. This inhibition of the mammalian biosynthesis of leukotrienes indicates that the compounds and pharmaceutical compositions thereof are useful to prevent or reduce the risk for, treat or ameliorate in mammals and especially in humans: 1) pulmonary disorders including diseases such as asthma, chronic bronchitis, and related obstructive airway diseases, 2) allergies and allergic reactions such as allergic rhinitis, contact dermatitis, allergic conjunctivitis, and the like, 3) inflammation such as arthritis or inflammatory bowel disease, 4) pain, 5) skin disorders such as atopic eczema, and the like, 6) cardiovascular disorders such as angina, formation of atherosclerotic plaques, myocardial ischemia, hypertension, platelet aggregation and the like, 7) renal insufficiency arising from ischaemia induced by immunological or chemical (cyclosporin) etiology and 8) migraine or cluster headache, 9) ocular conditions such as uveitis, 10) hepatitis resulting from chemical, immunological or infectious stimuli, 11) trauma or shock states such as burn injuries, endotoxemia and the like, 12) allograft rejection, 13) prevention of side effects associated with therapeutic administration of cytokines such as Interleukin II and tumor necrosis factor, 14) chronic lung diseases such as cystic fibrosis, bronchitis and other small- and large-airway diseases, 15) cholecystitis, 16) multiple sclerosis, 17) proliferation of myoblastic leukemia cells, 18) pulmonary fibrosis, 19) respiratory syncytial virus, 20) acne and 21) sleep apnea. Moreover, the compounds of this invention can be administered to patients, including adult and pediatric patients, for the relief of symptoms of allergic rhinitis, including seasonal allergic rhinitis.

Particularly, the compounds of this invention can be administered to patients, including adult and pediatric patients, for the prophylaxis of asthma and for chronic treatment of asthma. The compounds of this invention can be administered to patients, including adult and pediatric patients, for the treatment of asthma: (1) as an alternative to low-dose inhaled corticosteroids (ICS) for patients with mild persistent asthma, (2) as concomitant therapy with low-dose inhaled corticosteroids (ICS) for patients with mild persistent asthma, or (3) as concomitant therapy in patients with persistent asthma who are inadequately controlled on inhaled corticosteroids (ICS) or on combined ICS/long-acting beta-agonist (LABA) therapy. The compounds can be used for treatment of asthmatic patients including, but not limited to, steroid resistant/non-responder asthmatics, asthmatics for whom leukotriene modifiers have previously failed, smoking asthmatics, and aspirin sensitive asthmatics.

The compounds can be administered to patients to: (1) improve FEV1 (Forced Expitory Volume in one minute), (2) improve morning and evening PEF (Peak Expitory flow), (3) reduce beta-agonist use (measured by puffs/day), (4) reduce inhaled/systemic steroid use. (5) improve daytime asthma symptoms, (6) reduce number of nocturnal awakenings, 7) improve asthma control days, (8) reduce number of asthma exacerbations, wherein an exacerbation is defined as: requiring systemic steroid, an emergency room visit, hospitalization, an unscheduled asthma related doctor visit, decrease in A.M. PEF by >20% or A.M. PEF <180 l/min, increased SABA (short-acting beta-agonist) use >70% from baseline (minimum increase 2 puffs), or increased symptom score of >50%, (9) reduce the number of asthma attacks (measured as % of days with at least one attack over a specified period of total days), wherein the attack is one that requires systemic steroid use, an emergency room visit, hospitalization, or an unscheduled asthma related doctor visit, (10) reduce the number of acute asthma attacks, (11) reduce blood and sputum eosinophils, and/or (12) prevent and treat EIB (exercised induced bronchoconstriction).

The FLAP inhibitors of this invention can also be used in a therapeutically effective amount for promoting osteogenesis in a patient in need of such treatment. For example, the compounds could be used to promote osteogenesis to accelerate or enhance bone fracture healing, treat bone defects, and enhance bone formation. The compounds can be administered alone or in combination with one or more additional active agents that inhibit bone resorption, regulate calcium resorption from bone, enhance bone accumulation, enhance bone formation, induce bone formation, impair growth of microorganisms, reduce inflammation, and/or reduce pain.

The compounds of the present invention may also be used to treat or prevent mammalian (especially, human) disease states such as erosive gastritis; erosive esophagitis; diarrhea; cerebral spasm; premature labor, spontaneous abortion; dysmenorrhea; ischemia; noxious agent-induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure. Leukotriene biosynthesis inhibitors also act as inhibitors of tumor metastasis and exhibit cytoprotective action and therefore the compounds of this invention may also be useful in this regard.

The FLAP inhibitors of this invention can also be administered for prevention, amelioration and treatment of glomerulonephritis (see Guasch A., Zayas C. F., Badr K F. (1999), "MK-591 acutely restores glomerular size selectivity and reduces proteinuria in human glomerulonephritis," Kidney Int., 56:261-267); and also for and prevention, amelioration and treatment of kidney damage resulting from diabetes complications (see Valdivielso J M, Montero A., Badr K F., Munger K A. (2003), "Inhibition of FLAP decreases proteinuria in diabetic rats," J. Nephrol., 16(1):85-940.)

In addition, the compounds of this invention can also be used for the treatment of chronic obstructive pulmonary disease (COPD). As described in S. Kilfeather, Chest, 2002, vol 121, 197, airway neutrophilia in COPD patients is believed to be a contributing source of inflammation and is associated with airway remodeling. The presence of neutrophils is mediated in part by $LTB_4$, and treatment with the instant compounds could be used to reduce neutrophilic inflammation in patients with COPD and reduce the rate of COPD exacerbations. In particular, the compounds of this invention could be used for daily, preferably once-daily, maintenance treatment of airflow obstruction associated with COPD, including chronic bronchitis and emphysema.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions, and the like. Two assays can be used to measure cytoprotective ability. These assays are: (A) an ethanol-induced lesion assay and (B) an indomethacin-induced ulcer assay and are described in EP 140,684.

In particular, the compounds of the invention would be useful to reduce the gastric erosion caused by co-administration of a cyclooxygenase-2 selective inhibitor and low-dose aspirin. Cyclooxygenase-2 selective inhibitors are widely used as effective anti-inflammatory drugs with less potential for gastrointestinal complications as compared to traditional, non-selective non-steroidal anti-inflammatory drugs. However, the combined use of a cyclooxygenase-2 selective inhibitor with low-dose aspirin for cardio protection may compromise the gastrointestinal safety of this class of compounds. By virtue of its activity as a 5-lipoxygenase inhibitor, the compounds of the invention would be expected to be gastric protective in this regard. See Fiorucci, et al. FASEB J. 17:1171-1173, 2003. Cyclooxygenase-2 selective inhibitors for use with the invention include but are not limited to etoricoxib (ARCOXIA™) and celecoxib (CELEBREX®). A compound of this invention in combination with a cyclooxygenase-2 selective inhibitor could be administered in unit dosage form or separately to a patient on low-dose aspirin therapy. Alternatively, the cyclooxygenase-2 inhibitor could be administered in unit dosage form with low-dose aspirin, in which case a compound of this invention would be administered separately. All three active ingredients in unit dosage form is also encompassed. Conventional dosage amounts of the cyclooxygenase-2 selective inhibitor and aspirin (for cardio protection) may be utilized. Aspirin could be administered at 81 mg once daily.

The term "patient" includes mammals, especially humans, who use the instant active agents for the prevention or treatment of a medical condition. Administering of the drug to the patient includes both self-administration and administration to the patient by another person. The patient may be in need of treatment for an existing disease or medical condition, or may desire prophylactic treatment to prevent or reduce the risk of onset of atherosclerosis.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician. The term "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician.

It is understood that a specific daily dosage amount can simultaneously be both a therapeutically effective amount, e.g., for treatment to slow progression of existing atherosclerosis, and a prophylactically effective amount, e.g., for prevention of an atherosclerotic disease event or formation of new lesions.

In general, FLAP inhibitors can be identified as those compounds which have an $IC_{50}$ in the "FLAP Binding Assay" that is less than or equal to 1 μM, and preferably 500 nM or less, more preferably 100 nM or less, and most preferably 25 nM or less.

An effective amount of a FLAP inhibitor in the method of this invention is in the range of about 0.01 mg/kg to about 30 mg/kg of body weight per day, preferably 0.1 mg to about 15 mg per kg, and most preferably 0.5 to 7.5 mg per kg, in single or divided doses. A single daily dose is preferred but not necessary. For an average body weight of 70 kg, the dosage level is therefore from about 1 mg to about 2000 mg of drug per day, e.g. 10 mg, 25 mg, 50 mg, 75 mg, 100 mg, 125 mg, 150 mg, 175 mg, 200 mg, 250 mg or 500 mg per day, preferably given as a single daily dose or in divided doses two to four times a day, or in sustained release form. It will be understood, however, that the specific dose level for any particular patient will depend upon a variety of factors including the age, body weight, general health, sex, diet, time of administration, route of administration, rate of excretion, drug combination and the severity of the patient's condition. A consideration of these factors is well within the purview of the ordinarily skilled clinician for the purpose of determining the therapeutically effective or prophylactically effective dosage amount needed to prevent, counter, or arrest the progress of the condition. It is expected that the FLAP inhibitor will administered chronically on a daily basis for a length of time appropriate to treat or prevent the medical condition relevant to the patient, including a course of therapy lasting months, years or the life of the patient.

One or more additional active agents may be administered with a compound of Formula I. The term "additional active agent (or agents)" is intended to mean a pharmaceutically active agent (or agents) different from the compound of Formula I. In a broad embodiment, any suitable additional active agent or agents, including but not limited to anti-atherosclerotic agents such as a lipid modifying compound, anti-diabetic agents and/or anti-obesity agents and agents used for the treatment of metabolic syndrome, may be used in combination with the compound of Formula I in a single dosage formulation, or may be administered to the patient in a separate dosage formulation, which allows for concurrent or sequential administration of the active agents. The additional active agent or agents may have more than one pharmaceutical activity, for example it may have both lipid-modifying effects and anti-diabetic activity. Examples of additional active agents which may be employed include but are not limited to HMG-CoA reductase inhibitors, which include statins in their lactonized or dihydroxy open acid forms and pharmaceutically acceptable salts and esters thereof, including but not limited to lovastatin (MEVACOR®, see U.S. Pat. No. 4,342,767), simvastatin (ZOCOR®, see U.S. Pat. No. 4,444,784), pravastatin, particularly the sodium salt thereof (PRAVACHOL®, see U.S. Pat. No. 4,346,227), fluvastatin particularly the sodium salt thereof (LESCOL®, see U.S. Pat. No. 5,354,772), atorvastatin, particularly the calcium salt thereof (LIPITOR®, see U.S. Pat. No. 5,273,995), pitavastatin also referred to as NK-104 (see PCT international publication number WO 97/23200) and rosuvastatin (CRESTOR®; see U.S. Pat. No. 5,260,440); 5-lipoxygenase inhibitors; cholesterol ester transfer protein (CETP) inhibitors, for example JTT-705; HMG-CoA synthase inhibitors; squalene epoxidase inhibitors; squalene synthetase inhibitors (also known as squalene synthase inhibitors), acyl-coenzyme A: cholesterol acyltransferase (ACAT) inhibitors including selective inhibitors of ACAT-1 or ACAT-2 as well as dual inhibitors of ACAT-1 and -2; microsomal triglyceride transfer protein (MTP) inhibitors; niacin; niacin receptor agonists such as acipimox and acifran, as well as niacin receptor partial agonists; bile acid sequestrants; LDL (low density lipoprotein) receptor inducers; platelet aggregation inhibitors, for example glycoprotein IIb/IIIa fibrinogen receptor antagonists and aspirin; human peroxisome proliferator activated receptor gamma (PPARγ) agonists including the compounds commonly referred to as glitazones for example pioglitazone and rosiglitazone and, including those compounds included within the structural class known as thiazolidinediones as well as those PPARγ agonists outside the thiazolidinedione structural class; PPARα agonists such as clofibrate, fenofibrate including micronized fenofibrate, and gemfibrozil; PPAR dual α/γ agonists; vitamin $B_6$ (also known as pyridoxine) and the pharmaceutically acceptable salts thereof such as the HCl salt; vitamin $B_{12}$ (also known as cyanocobalamin); folic acid or a pharmaceutically acceptable salt or ester thereof such as the sodium salt and the methylglucamine salt; anti-oxidant vitamins such as vitamin C and E and beta carotene; beta-blockers; angiotensin II antagonists such as losartan and losartan with hydrochlorothiazide; angiotensin converting enzyme inhibitors such as enalapril and captopril; calcium channel blockers such as nifedipine and diltiazam; endothelian antagonists; agents that enhance ABCA1 gene expression; FXR and LXR ligands including both inhibitors and agonists; bisphosphonate compounds such as alendronate sodium; and cyclooxygenase-2 inhibitors such as etoricoxib, celecoxib and valdecoxib. Anti-obesity agents can be employed in combination with a compound of this invention including, but not limited to, sibunamine, orlistat, topiramate, naltrexone, bupriopion, phentermine, and phentermine/topiramate combination (QNEXA®); NPY5 antagonists; Acetyl-CoA Carboxylase-1 and -2 (ACC) inhibitors; MCH1R antagonists; and CB1 antagonists/inverse agonists such as those described in WO03/077847 and WO05/000809. Additional anti-diabetes agents which may be employed in combination with a compound of this invention include but are not limited to DPP-4 (dipeptidylpeptidase-4) inhibitors such as sitagliptin (JANUVIA®) and vildagliptin (GALVUS®); sulfonylureas e.g., chlorpropamide, tolazamide, glyburide, glipizide, and glimepiride; biguanides, e.g., metformin; alpha-glucosidase inhibitors e.g., acarbose and miglitol; meglitinides e.g., repaglinide; glucagon-receptor antagonists; and glucokinase activators.

Other advantageous pharmaceutical combinations comprise the compounds of this invention in combination with anti-cholinergics such as ipratropium bromide and tiotropium, bronchodilators such as the beta agonist salbutamol, metaproterenol, terbutaline, fenoterol, salmeterol, formoterol and the like, and the anti-asthmatic drugs theophylline, choline theophyllinate and enprofylline, the calcium antagonists nifedipine, diltiazem, nitrendipine, verapamil, nimodipine, felodipine, etc., and the corticosteroids, hydrocortisone, methylprednisolone, betamethasone, dexamethasone, beclomethasone, and the like. Particularly, for the prophylaxis and treatment of asthma, compounds of this invention can be used in combination with orally inhaled corticosteroids, such as beclomethasone (e.g. QVAR® Inhalation Aerosol), budesonide (e.g. Pulmicort Respules), flunisolide (e.g., AEROBID® and AEROBID®-M Inhaler System), fluticasone (e.g., FLOVENT® DISKUS® inhalation powder, FLOVENT® HFA Inhalation Aerosol), mometasone (e.g., ASMANEX® TWISTHALER®), and triamcinolone (e.g., AZMACORT® Inhalation Aerosol), and also with inhaled corticosteroid/LABA products such as fluticasone propionate/salmeterol (e.g., ADVAIR DISKUS®). The instant compounds could also be used in combination with leukotriene receptor antagonists such as montelukast (e.g., SINGULAIR®); phosphodiesterase 4 (PDE4) inhibitors such as roflumilast, N-Cyclopropyl-1-[3-(1-oxido-3-pyridinylethynyl)phenyl]-1,4-dihydro[1,8]naphthyridin-4-one-3-carboxamide and the compounds disclosed in PCT Publication WO2003/018579; and Very Late Antigen 4 (VLA4) inhibitors such as the compounds disclosed in U.S. Pat. No. 6,229,011, particularly R411 (N-(2-Chloro-6-methylbenzoyl)-4-[(2,6-dichlorobenzoyl)amino]-L-phenylalanine-2-(diethylamino)ethyl ester which is an ester pro-drug of the active moiety, N-(2-chloro-6-methylbenzoyl)-4-[(2,6-dichlorobenzoyl)amino]-L-phenylalanine), and the compounds disclosed in PCT publication WO2006/023396.

Still another type of agent that can be used in combination with the compounds of this invention are cholesterol absorption inhibitors. Cholesterol absorption inhibitors block the movement of cholesterol from the intestinal lumen into enterocytes of the small intestinal wall. This blockade is their primary mode of action in reducing serum cholesterol levels. These compounds are distinct from compounds which reduce serum cholesterol levels primarily by mechanisms of action such as acyl coenzyme A—cholesterol acyl transferase (ACAT) inhibition, inhibition of triglyceride synthesis, MTP inhibition, bile acid sequestration, and transcription modulation such as agonists or antagonists of nuclear hormones. Cholesterol absorption inhibitors include but are not limited to those described in U.S. Pat. No. 5,846,966, U.S. Pat. No. 5,631,365, U.S. Pat. No. 5,767,115, U.S. Pat. No. 6,133,001, U.S. Pat. No. 5,886,171, U.S. Pat. No. 5,856,473, U.S. Pat. No. 5,756,470, U.S. Pat. No. 5,739,321, U.S. Pat. No. 5,919,672, U.S. Pat. No. 6,498,156, US2004/0082561, US2004/0067913, US2004/0063929, US2002-0137689, WO 05/047248, WO 05/021497, WO 05/021495, WO 05/000353, WO 04/005247, WO 00/63703, WO 00/60107, WO 00/38725, WO 00/34240, WO 00/20623, WO 97/45406, WO 97/16424, WO 97/16455, and WO 95/08532. An exemplary cholesterol absorption inhibitor is ezetimibe, marketed in the U.S. under the tradename ZETIA® described in U.S. Pat. No. Re 37721 and the Physician's Desk Reference as well as VYTORIN®, which is a combination of ezetimibe with simvastatin.

This and other cholesterol absorption inhibitors can be identified according to the assay of hypolipidemic compounds using the hyperlipidemic hamster described in U.S. Pat. Re 37721, beginning in column 20, in which hamsters are fed a controlled cholesterol diet and dosed with test compounds for seven days. Plasma lipid analysis is conducted and data is reported as percent reduction of lipid versus control.

Therapeutically effective amounts of cholesterol absorption inhibitors include dosages of from about 0.01 mg/kg to about 30 mg/kg of body weight per day, preferably about 0.1 mg/kg to about 15 mg/kg. For an average body weight of 70 kg, the dosage level is therefore from about 0.7 mg to about 2100 mg of drug per day, e.g. 10, 20, 40, 100 or 200 mg per day, preferably given as a single daily dose or in divided doses two to six times a day, or in sustained release form. This dosage regimen may be adjusted to provide the optimal therapeutic response when the cholesterol absorption inhibitor is used in combination with a compound of the instant invention.

In the method of treatment of this invention, the FLAP inhibitors may be administered via any suitable route of administration such as orally, parenterally, or rectally in dosage unit formulations containing conventional non-toxic pharmaceutically acceptable carriers, adjuvants and vehicles. The term parenteral as used herein includes subcutaneous injections, intravenous, intramuscular, infrasternal injection or infusion techniques. Oral formulations are preferred.

For oral use, the pharmaceutical compositions of this invention containing the active ingredient may be in forms such as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients, which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc.

Oral immediate-release and time-controlled release dosage forms may be employed, as well as enterically coated oral dosage forms. Tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. One example of a time-controlled release device is described in U.S. Pat. No. 5,366,738. They may also be coated by the technique described in U.S. Pat. Nos. 4,256,108; 4,166,452; and 4,265,874 to form osmotic therapeutic tablets for controlled release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxy-propylmethycellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier.

A therapeutically effective amount of a compound of Formula I can be used for the preparation of a medicament useful for treating or preventing any of the medical conditions described herein, in dosage amounts described herein. For example, a compound of Formula I can be used for the preparation of a medicament useful for preventing or reducing the risk of developing atherosclerotic disease, halting or slowing the progression of atherosclerotic disease once it has become clinically manifest, and preventing or reducing the risk of a first or subsequent occurrence of an atherosclerotic disease event. Additionally, the medicament may be useful for the treatment of asthma, allergies and allergic conditions, inflammation, COPD or erosive gastritis. The medicament comprised of a compound of Formula I may also be prepared with one or more additional active agents, such as those described herein.

The compounds of structural Formula I of the present invention can be prepared according to the procedures of the following Schemes and Examples, using appropriate materials and are further exemplified by the specific examples which follow. Moreover, by utilizing the procedures described herein, one of ordinary skill in the art can readily prepare additional compounds of the present invention claimed herein. The compounds illustrated in the examples are not, however, to be construed as forming the only genus that is considered as the invention. All temperatures are degrees Celsius unless otherwise noted. Mass spectra (MS) were measured by electron-spray ion-mass spectroscopy (ES-MS).

The instant compounds are generally isolated in a pharmaceutically acceptable form which can either be the free base or free acid if an acid group is present, or an appropriate salt derivative, such as those described above. The free amine bases corresponding to the isolated salts can be generated by neutralization with a suitable base, such as aqueous sodium hydrogencarbonate, sodium carbonate, sodium hydroxide, or potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization.

Some abbreviations used herein are as follows:

ABCA1 is adenosyltriphosphate-binding cassette-family A1; Ac is acetyl; AIBN is 2,2'-azobis(2-methylpropionitrile); aq. is aqueous; Ar is Aryl; Bn is benzyl; Doc is tertbutylcarbamoyl; br is broad; Bu is butyl; $^t$Bu is tert-butyl; celite is Celite® diatomaceous earth; cpm is counts per minute; δ is chemical shift; DCM is dichloromethane; d is doublet; DEAD is diethylazodicarboxylate; DIAD is diisopropylazodicarboxylate; DIPEA is diisopropylethylamine; DMAP is 4-dimethylaminopyridine; DMF is N,N-dimethylformamide; dppf is 1,1'-bis(diphenylphosphino)ferrocene; DMSO is dimethyl sulfoxide; EDC is N-(3-dimethylaminopropyl)-N'-ethylcarbodiimide hydrochloride; EDTA is ethylendiamine tetraacetic acid; equiv. is equivalent(s); ES-MS is electrospray ion-mass spectroscopy; Et is ethyl; $Et_2O$ is diethyl ether; EtOH is ethanol, EtOAc is ethyl acetate; FXR is farnesoid X receptor; g is gram; h is hours; HATU is O-(7-azabenzotriazol-1-yl)-N,N,N',N'-tetramethyluronium hexafluorophosphate; HetAr or HAR is Heteroaryl; HMG-CoA is 3-hydroxy-3-methyl-glutaryl coenzyme A; $^1$HNMR is proton nuclear magnetic resonance; HOAt is 1-hydroxy-7-azabenzotriazole; HOBt is 1-hydroxybenzotriazole; HPLC is high performance liquid chromatography; Hz is hertz; i is Iso; $IC_{50}$ is concentration at which 50% inhibition exists; J is internuclear coupling constant; kg is kilogram; LG is leaving group; $LTB_4$ is leukotriene $B_4$; LXR is liver X receptor; m is multiplet; M is molar; Me is methyl; m.p. is melting point; mg is milligram; μg is microgram; MeCN is acetonitrile; MeOH is methanol; MHz is megahertz; min is minute; mL is milliliter; mm is millimeter, μL is microliter; mM is milimolar; μM is micromolar, mmol is milimoles; Ms is methanesulfonyl; MS is mass spectrum, and a mass spectrum obtained by ES-MS may be denoted herein by "ES"; m/z is mass to charge ratio; n is normal; nm is nanometer, nM is nanomolar; NMM is N-methylmorpholine; NMO is N-methylmorpholine-N-oxide; NMP is N-methylpyrrolidin-2-one; nPr is n-propyl; p is pentet; p is para; PEG is polyethylene glycol; Ph is phenyl; Phth is phthalimidoyl; PPARα is peroxisome proliferator activated receptor alpha; Pr is propyl; iPr is isopropyl; PyBOP is benzotriaxole-1-yl-oxy-tris-pyrrolidino-phosphonium hexafluorophosphate; q is quartet; rt is room temperature; s is singlet; sec is secondary; t is triplet; $^t$BuOH is tert-butanol; tert is tertiary; Tf is trifluoromethanesulfonyl; TFA is trifluoroacetic acid; and THF is tetrahydrofuran; Ts is tosyl; UV is ultraviolet; x g is times gravity; ° C. is degrees Celsius.

Reaction schemes A-R illustrate the methods employed in the synthesis of the compounds of Formula I. All abbreviations are as defined above unless indicated otherwise. In reaction schemes A-R, substituents on the rings are labeled with R, which corresponds to $R^c$, $R^d$ and $R^e$ as defined in structural Formula I. In the Schemes, all substituents are as defined above in Formula I unless indicated otherwise.

Reaction schemes A-R illustrate the methods employed in the synthesis of the compounds of the present invention of structural Formula I. All abbreviations are as defined above unless indicated otherwise. In reaction schemes A-R, substituents on the rings are labeled with R, which corresponds to $R^c$, $R^d$ and $R^e$ as defined in structural Formula I.

Reaction scheme A illustrates a preferred method of synthesis of a compound type 8. In this method, a ketone or aldehyde of type 1 is treated with an organometallic reagent of type 2, capable of transferring an aryl group, to afford a compound of type 3. Preferred organometallic reagents for effecting this transformation include organolithium (2, M=Li) and organomagnesium (2, M=Mg; Grignard) compounds. When organolithium reagents are employed, the reaction can be conducted in a variety of solvents, such as hexanes or diethyl ether or the like, at temperatures between −78° C. and rt. When Grignard reagents are employed as shown in scheme A, it is customary to conduct the reaction in a suitable ethereal solvent such as THF or diethyl ether, or mixtures thereof, at temperatures between −78° C. and the boiling temperature of the solvent. The organolithium and Grignard reagents are commonly purchased from commercial sources, but can be prepared synthetically according to known methods of organic synthesis. The resulting alcohol 3 can be treated with a protected aminomethylfuran derivative of type 4 in an electrophilic aromatic substitution process generally referred to as a Friedel Crafts arylation reaction. The preferred protecting group for the amino functionality in 4 as depicted in scheme A is phthalimide, but is by no means limited to such a group. Typical conditions for performing the arylation of 3 include the generation of an intermediate carbocation of type 5 derived from 3, followed by in situ trapping with a suitable aromatic coupling partner of type 4 to afford a product of type 6. It is customary to conduct the reaction in the presence of either suitable Bronstead acids such as tetrafluoboric acid or the like, or Lewis acids such as boron trifluoride or the like (*J. Am. Chem. Soc.* 2005, 127, 9348-9349). The reaction may also be performed in the presence of a variety of inert organic solvents, such as dichloromethane or 1,2-dichloroethane or the like, at temperatures typically between −78° C. and rt. Preferred conditions for removal of the phthalimide protecting group involve treatment of 6 with reagents such as sodium methoxide or hydrazine or n-butylamine, in solvents such as MeOH or EtOH, at temperatures typically between rt and the boiling temperature of the solvent. The product of the reaction is an amine of type 7 which can be transformed to a compound of type 8 in the presence of a suitable activating reagent, such as bromine or iodine, or additionally, aqueous hydrochloric or hydrobromic acid. The reaction can be conducted in a variety of aqueous solvent mixtures that include solvents such as MeOH or EtOH or the like, at temperatures between it and −20° C. The product 8 can be further elaborated to other compounds of the present invention (I) as described in the subsequent schemes.

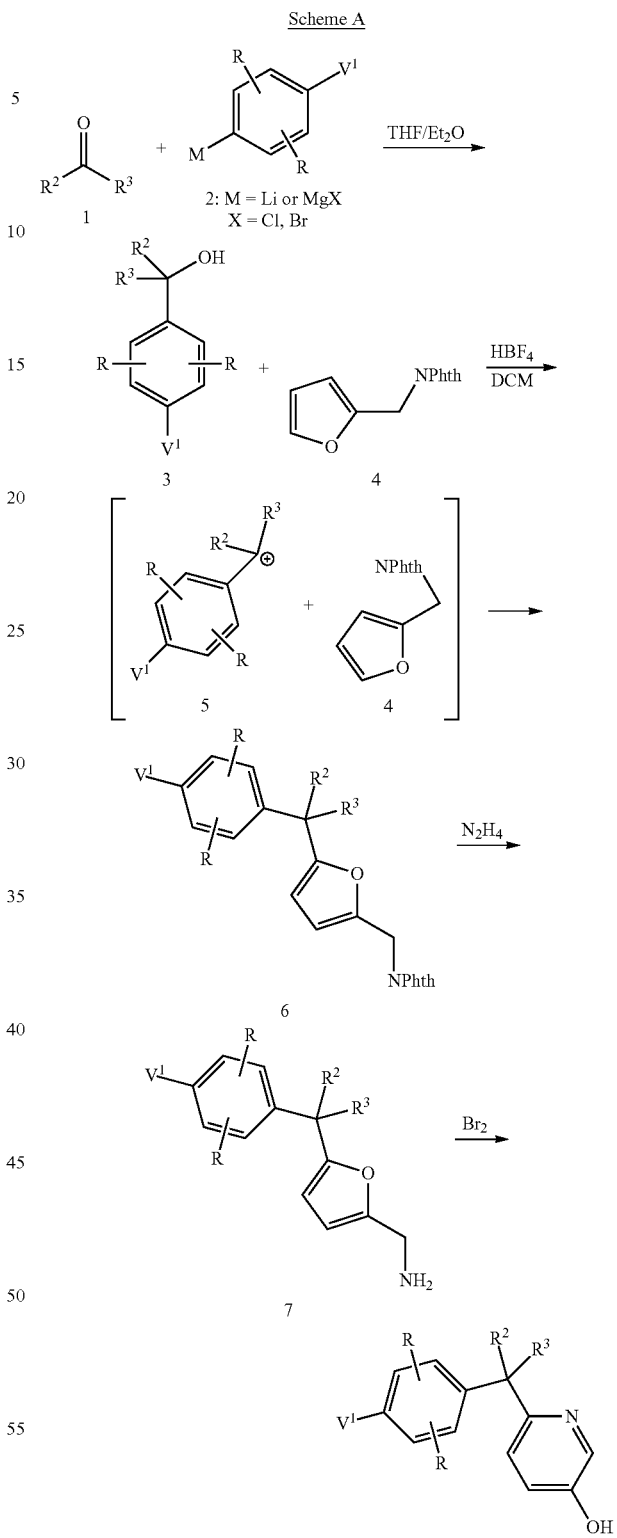

Reaction scheme B illustrates a preferred method of synthesis of a compound of type 16. In this method, an acid chloride derivative of type 9, often generated from the respective carboxylic acid precursor using methods known to those skilled in the art of organic synthesis, is treated with an organometallic reagent of type 10 or type 11 to afford a product of type 12. Preferred organometallic reagents for effecting this transformation include organomagnesium (Grignard) and organozinc compounds. When Grignard reagents (10) are employed, the preferred conditions are similar to those described in scheme A. When organozinc reagents (11) are employed, the reaction is generally conducted in the presence of a suitable organotransition metal catalyst such as bis(triphenylphosphino)palladium(II) dichloride or copper(I) chloride or the like, in a variety of solvents such as THF or diethyl ether, at temperatures between −20° C. and rt (*Chem. Rev.* 1993, 93, 2117-2188). The Grignard and organozinc reagents are commonly purchased from commercial sources, but can be prepared synthetically according to known methods of organic synthesis. The resulting ketone 12 can then be treated with an organometallic reagent of type 2 under similar conditions to those described in scheme A to furnish a product of type 13. The hydroxyl group in 13 can be removed in a reaction sequence commonly referred to as the Barton-McCombie Deoxygenation (*J. Chem. Soc., Perkin Trans. I* 1975, 1574-1585). The reaction process requires initial activation of the hydroxyl moiety, which is achieved via alkylation of this group with a reagent such as phenyl thionochloroformate, in the presence of a suitable tertiary amine base such as pyridine, to afford a thiocarbonate derivative of type 14. Acylations of this type can be conducted in a variety of inert organic solvents such as dichloromethane or 1,2-dichloroethane, at temperatures typically between −20° C. and rt. Alternatively, a xanthate derivative of type 15 may also be prepared, often by a three step sequence involving treatment of 13 with a base such as sodium hydride or potassium hydride, followed by introduction of carbon disulfide, and finally, in situ alkylation with an agent such as methyl iodide. Xanthate formation is generally performed in an ethereal solvent such as THF or diethyl ether, at temperatures typically between −20° C. and rt. Deoxygenation of 14 or 15 can be effected with a reducing agent such as a trialkyltin hydride, often in the presence of a free radical initiator such as AIBN or the like. Reactions of this type are performed in an inert organic solvent such as benzene or toluene or dimethoxyethane, that has been appropriately degassed, and at temperatures often corresponding to the boiling temperature of the solvent. It may be preferable to use an additive, such as potassium iodide or tetrabutylammonium iodide or the like, to accelerate or promote the reaction. The product is a compound of type 16, which can be elaborated to compounds of the present invention (I) as described in the subsequent schemes.

Scheme B

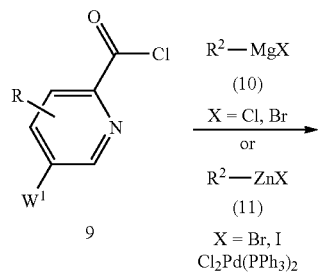

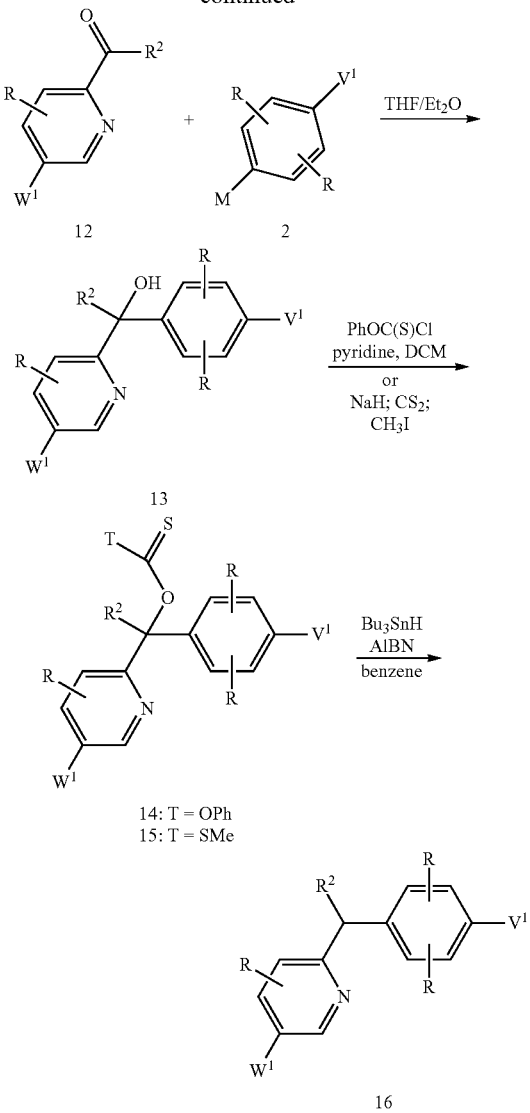

$W^1 = R^1$ as shown in formula 1 or a group that can be converted to $R^1$

Reaction scheme C illustrates an alternative method of synthesis of compounds of structural formula 20. In this method, a compound of type 17 is treated with bis(pinacolato) diboron in the presence of a suitable palladium catalyst, such as [1,1'-bis(diphenylphosphino)ferrocene]dichloropalladium (II) and an auxiliary nucleophile such as potassium acetate or the like. The reaction is generally conducted in an inert organic solvent, such as DMSO or dioxane or the like, at elevated temperatures generally between 70° C. and 100° C., for a period of 1-24 h (*J. Org. Chem.* 1995, 60, 7508-7510). The product of this reaction is an intermediate boronate of type 18, which can participate in organotransition metal catalyzed cross-coupling reactions commonly referred to as the Suzuki reaction, in which the aforementioned boronate (18) is treated with an aryl- or heteroaryl-coupling partner of type 19, in the presence of a suitable palladium catalyst, such as [1,1'-bis(diphenylphosphino)ferrocene]dichloropalladium (II) or tetrakistripheny 1 phosphinepalladium(0) or the like, and a base such as aqueous sodium carbonate or aqueous tribasic sodium phosphate or the like (*Pure Appl. Chem.* 1991, 63, 419-422). The reaction is usually performed in an inert organic solvent such as a toluene-EtOH mixture or dioxane, at temperatures above rt, for a period of 3-24 h. Recent advancements in the Suzuki reaction have allowed this type of transformation to be conducted in many cases at rt (for example, see: *J. Am. Chem. Soc.* 2000, 122, 4020-4028 and references cited therein). The product is a compound of type 20, which can be elaborated to compounds of the present invention (I) as described in the subsequent schemes.

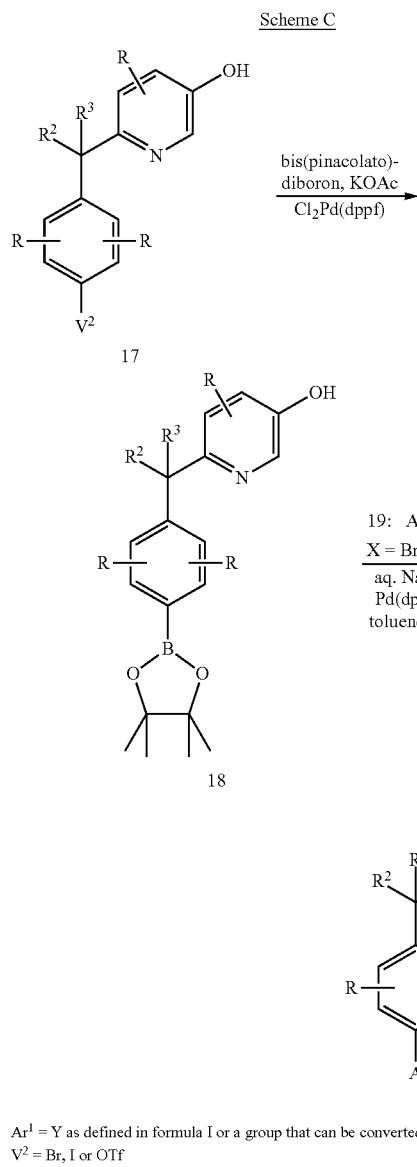

Ar$^1$ = Y as defined in formula I or a group that can be converted to Y
V$^2$ = Br, I or OTf Reaction scheme D illustrates a preferred method of synthesis of compounds of type 23. In this method, an aryl iodide of type 21 is treated with an alcohol of type 22 in the presence of a copper (I) catalyst and a suitable ligand, such as 1,10-phenanthroline. The reaction is performed in the presence of a mild base, such as cesium carbonate, or potassium fluoride-alumina, in a non-polar solvent, such as toluene, at elevated temperatures between 100° C. and the boiling point of the solvent, for reaction times up to 48 h. (*Org. Lett.* 2002, 4, 973-976. and *Synlett* 2005, 1101-1104.) Recent literature exists for performing the above method in the presence of a suitable palladium catalyst-ligand system. (*J. Am. Chem. Soc.* 2005, 127, 8146-8149, and references cited therein.) The product of the reaction is 23, which was be elaborated to compounds of the present invention (I) as described in the subsequent schemes.

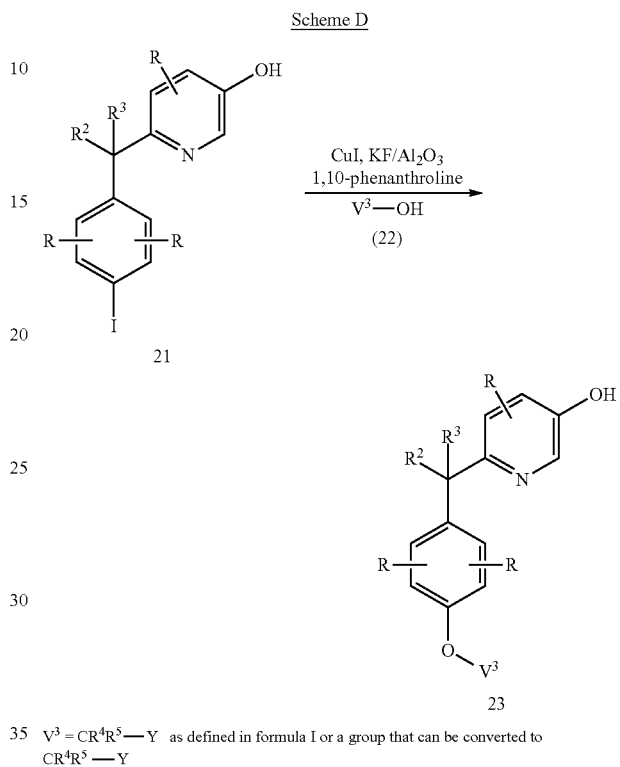

V$^3$ = CR$^4$R$^5$—Y as defined in formula I or a group that can be converted to CR$^4$R$^5$—Y Reaction scheme E illustrates the preferred method of synthesis of compounds of structural formula 28 and 29. In this method, compounds of type 21 are treated with agents of type 24, in which PG is a suitable protecting group, exemplified by, but not limited to, tert-butyldimethylsilyl, and X is a suitable leaving group, such as halide, mesylate or trifluoromethylsulfonate, to afford protected hydroxypyridine compounds of type 25. The reaction may be performed under a variety of conditions known to those skilled in the art. (Greene, T. W.; Wuts, P. G. M. *Protective Groups in Organic Synthesis*, Wiley-Interscience, 1999, 3$^{rd}$ Edn., and references therein) Compounds of type 25 can then be treated with a terminal alkyne of type 26 in an organotransition metal catalyzed cross-coupling process commonly referred to as the Sonogashira reaction. The reaction is performed in the presence of a suitable palladium catalyst and a copper(I) co-catalyst: such as copper(I) iodide, and typically employs an excess of an amine base, such as triethylamine and diethylamine. The reaction is conducted in an inert organic solvent such as DMF, at temperatures ranging from ambient temperature to about 100° C., for a period of 3-24 hours. The product of the reaction is an alkyne of type 27 which can then be converted into an alkene derivative of type 28 or a saturated alkane derivative of type 29. If 28 is desired, preferred conditions for performing the partial reduction of 27 involve the use of a Lindlar catalyst reagent system under an atmospheric or elevated pressure of hydrogen. The reaction is usually conducted in an inert organic solvent, such as EtOH and EtOAc, or combinations thereof, and at room temperature for a period of 3-15 hours. If 29 is desired, then the reduction of 27 is performed with any one of a variety of palladium-on-carbon catalysts, at either atmospheric or elevated pressure of hydrogen. Products of the reaction can be deprotected following procedures cited in the above reference and elaborated to compounds of the present invention (I) as described in the subsequent schemes.

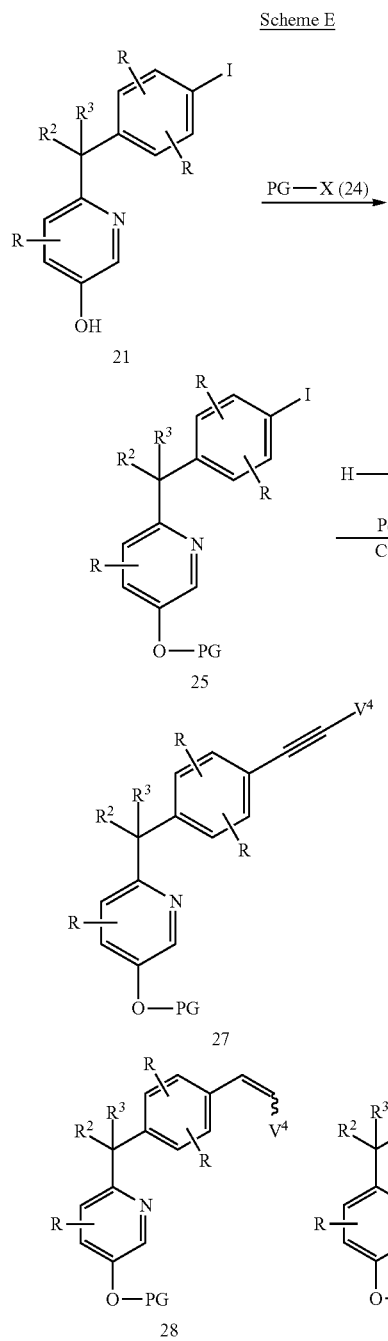

PG = a protecting group that can be selectivley removed
X = a suitable leaving group, such as Cl, Br or OTf
$V^4$ = Y as defined in formula I or a group that can be converted to Y Reaction scheme F illustrates a preferred method for the synthesis of compounds of the structural formula 32. In this method, 30 is reacted with a triflating agent, such as trifluoromethansulfonic anhydride or 2-(N,N,-bis(trifluoromethansulfonyl)amino pyridine, or the like, in the presence of a tertiary amine base, such as triethylamine or diisopropylethylamine, to afford an intermediate compound of type 31. The triflating reaction is typically performed in aprotic organic solvents, such as DCM or THF, at temperatures that range from −78° C. to room temperature. Compounds of type 31 can be treated with methanol in the presence of a suitable palladium catalyst, such as [1,1'-bis(diphenylphosphino)-ferrocene]dichloropalladium(II), or the like, and a tertiary amine base, such as triethylamine, or diisopropylethylamine, or the like, in an inert organic solvent like DMF. The reaction is usually conducted at elevated temperature, typically between 50° C. and 100° C., for periods of 3-24 h, under an atmosphere of carbon monoxide (*Tetrahedron Lett.* 1986, 27, 3931-3934). In certain cases, it may be preferable to use elevated pressures of carbon monoxide, or an additive, such as lithium chloride, to promote or accelerate the reaction. The product of the reaction is an ester of structural formula 32, which can be elaborated to compounds of the present invention (I) as described in the subsequent schemes.

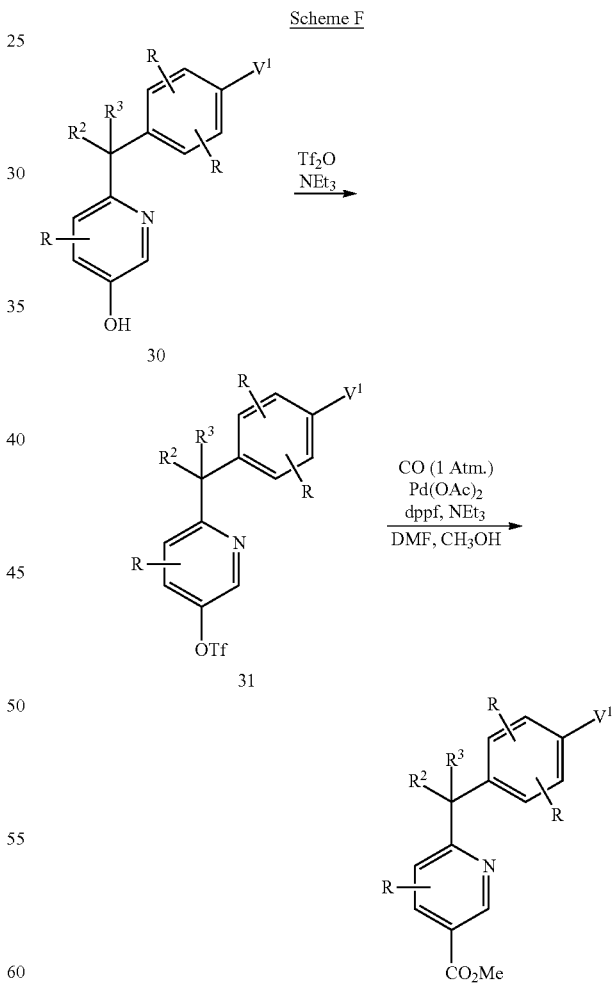

Reaction scheme G illustrates a preferred method for the elaboration of a compound type 31 to afford a compound of type 33. In this method, 31 is treated with a cyanide source such as potassium cyanide or trimethylsilylcyanide or the like, in the presence of a suitable palladium catalyst/ligand reagent system. It may be preferable to use an inorganic additive such as a copper(I) salt and/or a base such as triethylamine to accelerate or promote the reaction. It is customary to conduct the reaction in inert organic solvent, preferably a dipolar aprotic solvent, such as DMF or NMP or MeCN, at elevated reaction temperatures typically between 50-140° C., for a period of 3-24 hours. The product of the reaction is a nitrile of type 33, which can be elaborated to compounds of the present invention (I) as described in subsequent schemes.

Scheme G

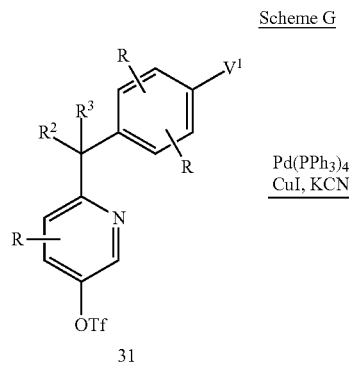

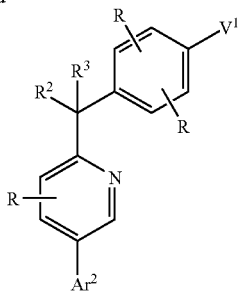

Ar² = R¹ as defined in formula I or a group that can be converted to R¹

Reaction scheme I illustrates a preferred method of synthesis of compounds of structural formula 36 following methods similar to those previously described in Scheme C.

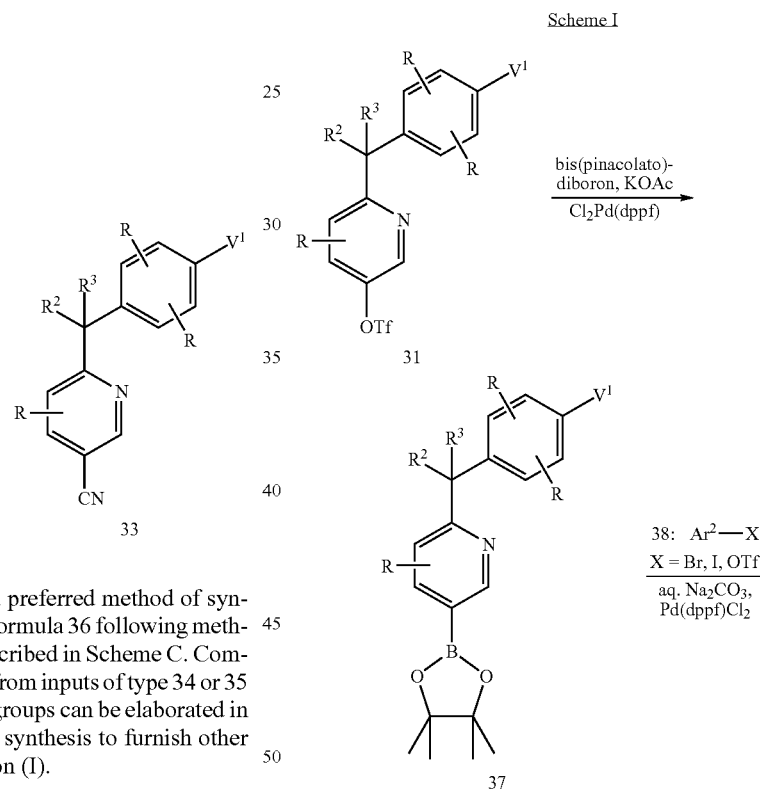

Reaction scheme H illustrates a preferred method of synthesis of compounds of structural formula 36 following methods similar to those previously described in Scheme C. Compounds of type 36 that are derived from inputs of type 34 or 35 that contain additional functional groups can be elaborated in numerous ways known in organic synthesis to furnish other compounds of the present invention (I).

Scheme H

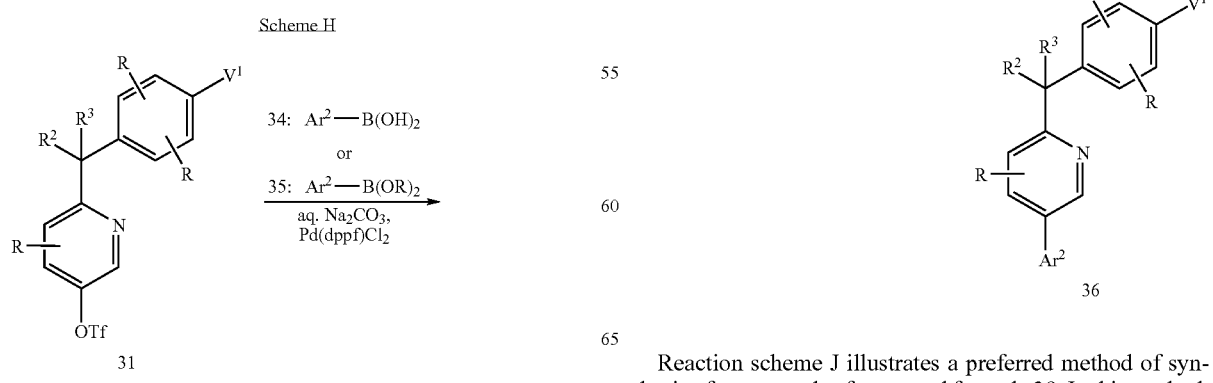

Reaction scheme J illustrates a preferred method of synthesis of compounds of structural formula 39. In this method, compounds of type 32 can be hydrolyzed to carboxylic acids of type 39 using a variety of methods known to those skilled in organic synthesis. The product carboxylic acid of structural formula 39 can be used in a variety of methods known in organic synthesis to afford compounds of the present invention (I).

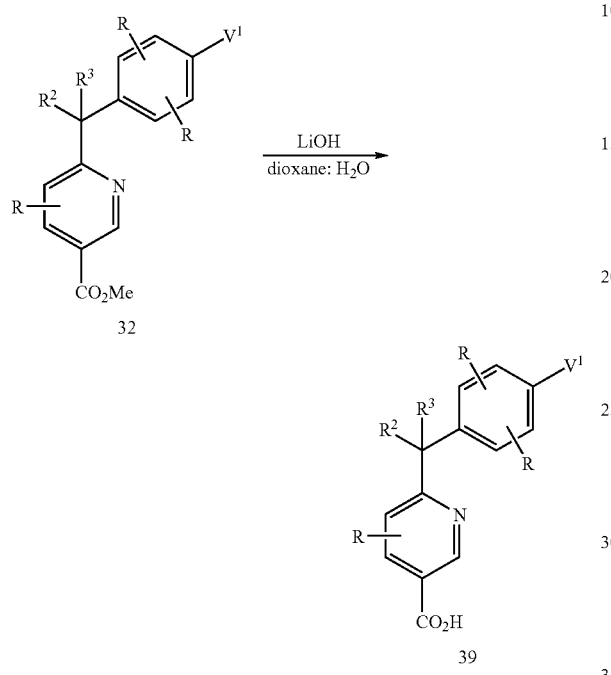

Reaction scheme K illustrates the preferred method of synthesis of compounds of structural formula 40, 41 and 42. In this method, 31 is treated with either allyltributylstannane or vinyltributylstannane in the presence of a suitable palladium catalyst such as [1,1'-bis(diphenylphosphino)-ferrocene]dichloropalladium(II), in an inert organic solvent like DMF or NMP. The reaction is usually conducted at elevated temperatures, typically between 50-120° C., for periods of 2-24 hours. In certain cases, it may be essential to use an additive such as lithium chloride to promote the reaction. Often, the reaction times can be significantly reduced if the reaction is conducted under microwave irradiation. The product of the reaction is an alkene of structural formula 40 which can be synthetically elaborated, using a variety of methods known in organic synthesis. For example, 40 can be oxidatively cleaved to afford an aldehyde of type 41, which can be further oxidized to a carboxylic acid derivative of structural formula 42. A preferred method for the oxidative cleavage reaction is the two-step process shown in reaction scheme I. Alkene 40 is first oxidized to a vicinal diol using catalytic osmium tetraoxide in the presence of a stoichiometric reoxidant such as NMO, in a solvent system such as acetone-water. The intermediate vicinal diol which forms is generally not isolated, but is in turn subjected to cleavage with sodium periodate in a suitable mixed solvent system like THF-water to afford 41. Both steps in the oxidative cleavage sequence are generally completed during periods of several minutes to a few hours, at temperatures between 0° C. and room temperature. Aldehyde 41 can then be further oxidized to 42 using a buffered chlorite oxidation system. In this method, 41 is treated with sodium chlorite and monobasic sodium phosphate in the presence of a chlorine scavenger, such as 2-methyl-2-butene. The reaction is conducted typically in a solvent system like n-butanol-water, for periods of 1-6 hours, at temperatures between 0° C. and room temperature. In certain cases, 41 can be directly converted to 42 using the sodium periodate/ruthenium trichloride reagent system. Both 41 and 42 can be elaborated in numerous ways known in organic synthesis to furnish other compounds of the present invention (I).

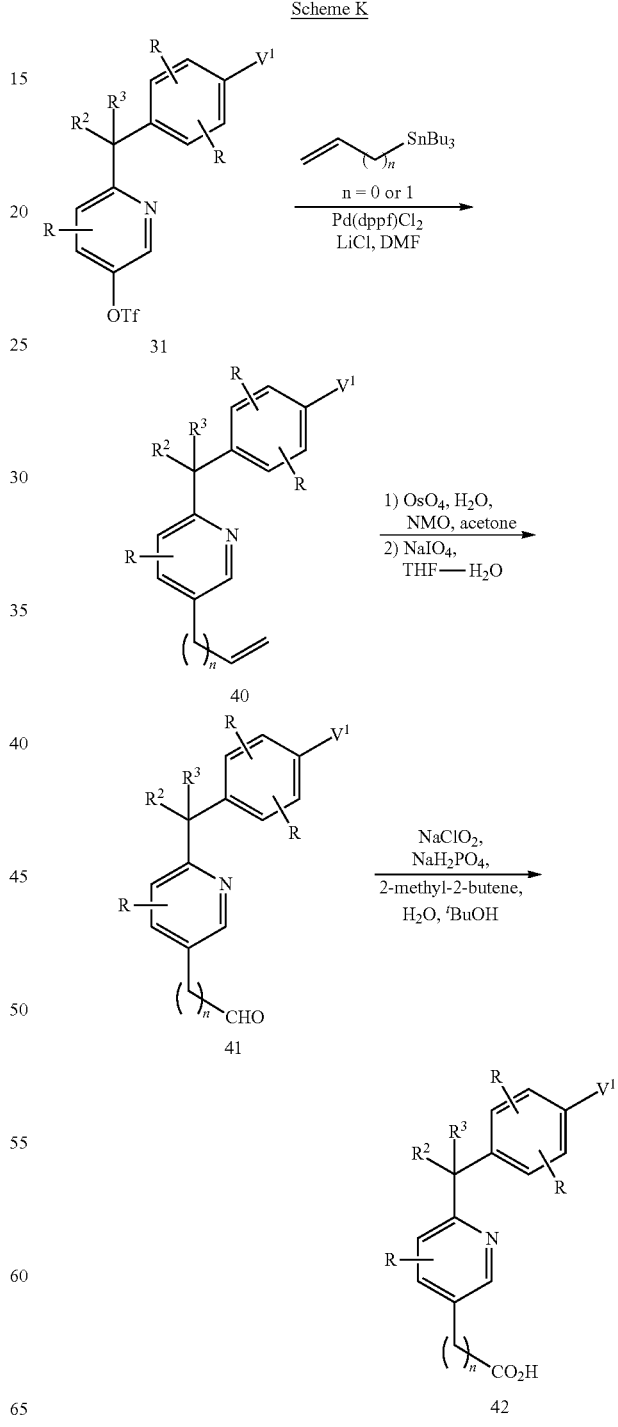

Reaction scheme L illustrates the preferred method of synthesis of a compound of type 43. In this method, compounds of type 31 can be reduced by treatment with an appropriate reducing agent, such as a trialkylammonium formate, or ammonium formate, or triethylsilane, or the like, in the presence of a suitable homogeneous palladium catalyst, such as [1,1'-bis(diphenylphosphino)ferrocene]-dichloropalladium (II) in an inert organic solvent, preferably a polar aprotic solvent, such as DMF, or NMP. The reaction is usually run at elevated temperatures, typically between 50-90° C., to afford an aryl compound of type 43.

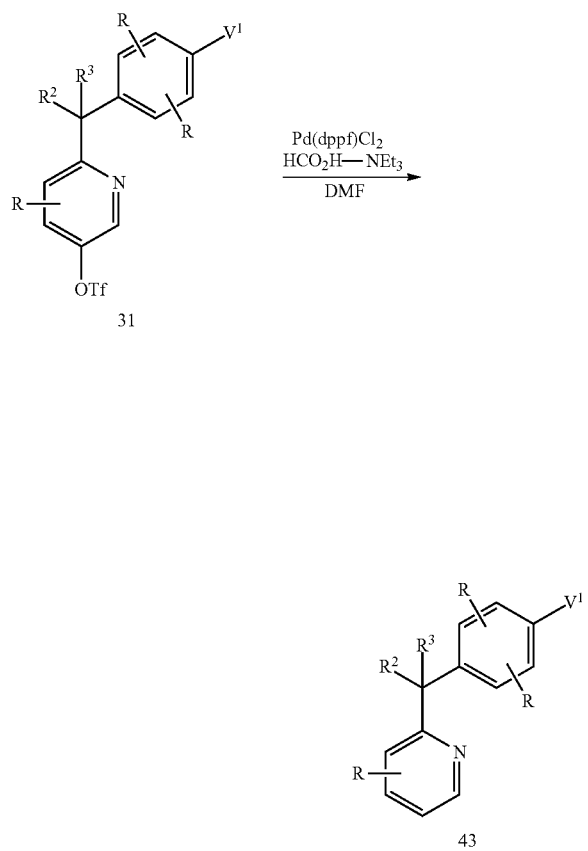

Scheme L

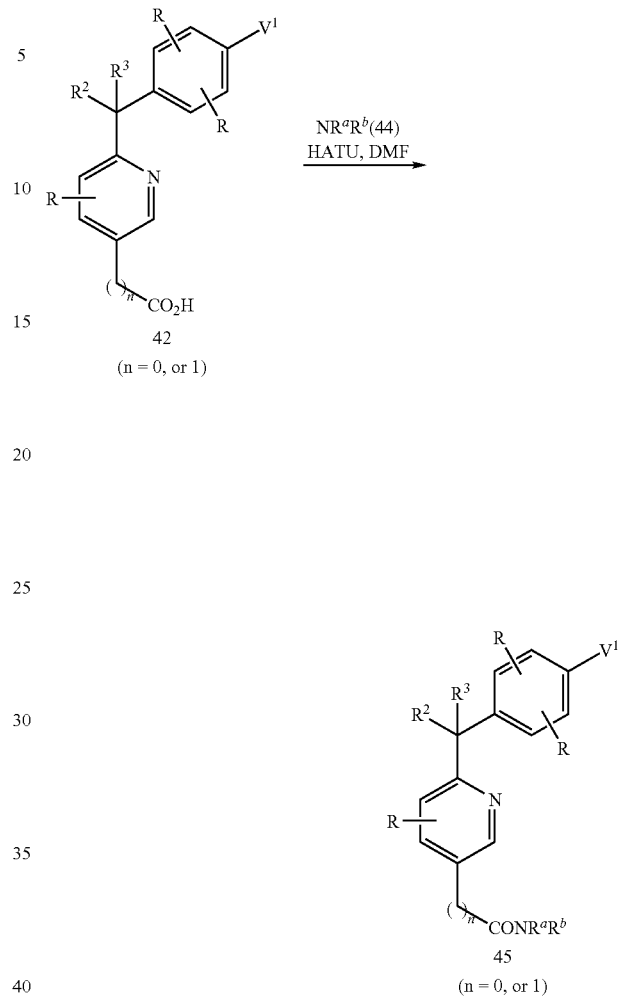

Scheme M

Reaction scheme M illustrates the preferred method of synthesis of compounds of structural formula 45. In the most general case, 42 is treated with an amine of type 44 to afford an amide of type 45. The amide bond coupling reaction illustrated in reaction scheme M is conducted in an appropriate inert solvent such as DMF, DCM or the like and may be performed with a variety of reagents suitable for amide coupling reactions such as HATU, EDC or PyBOP. Preferred conditions for the amide bond coupling reaction shown in reaction Scheme M are known to those skilled in organic synthesis. Such modifications may include, but are not limited to, the use of basic reagents such as triethylamine, DIPEA, or NMM; or the addition of an additive such as HOAt or HOBt. Alternatively, 44 may be treated with an activated ester or acid chloride derivative of 42, which also affords 45. The amide bond coupling shown in reaction Scheme M is usually conducted at a temperatures between 0° C. and room temperature, occasionally at elevated temperatures, and the coupling reaction is typically conducted for periods of 1 to 24 hours.

Reaction scheme N illustrates a preferred method for the synthesis of a compound of type 47. In this method, 42 is subjected to the Curtius reaction to afford the N-Boc protected amine derivative of structural formula 46. The reaction is performed by reacting 42 with diphenylphosphoryl azide in the presence of a tertiary amine such as triethylamine or DIPEA in a solvent such as toluene. The initial product is generally accepted to be the acyl azide, which is rearranged to the isocyanate in a thermal process analogous to the Wolff rearrangement of acyl carbenes. The rearrangment is conducted typically at the reflux temperature of the solvent, for instance 110° C., and the rearrangement is usually completed in periods of 1-5 hours. The intermediate isocyanate which forms is generally not isolated, but is in turn subjected to in situ reaction with a suitable alcohol such as tert-butyl alcohol to afford carbamate 46. The N-Boc group can be removed by a suitable deprotection method such as treatment with hydrogen chloride in EtOAc or TFA in DCM. The deprotection is conducted typically at temperatures between 0° C. and room temperature, and the reaction is usually complete in 0.5-3 hours. The product amine of structural formula 47 can be used as a coupling partner using a variety of methods known in organic synthesis to afford compounds of the present invention.

Scheme N

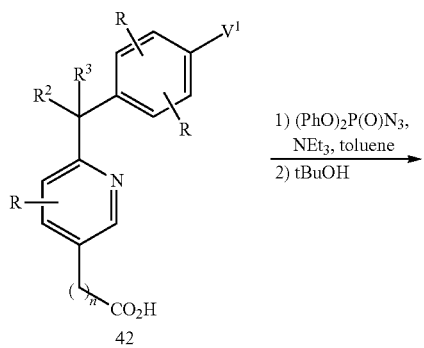
42
(n = 0, or 1)

1) (PhO)₂P(O)N₃, NEt₃, toluene
2) tBuOH
→

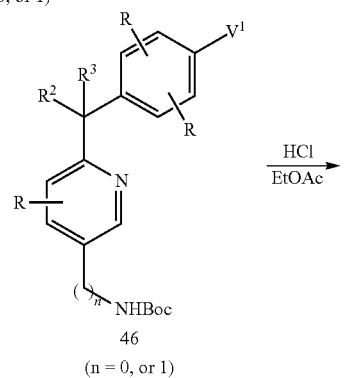
46
(n = 0, or 1)

HCl
EtOAc
→

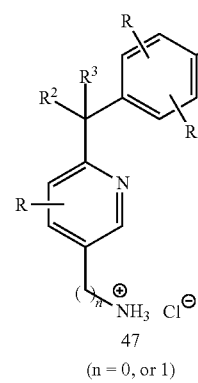
47
(n = 0, or 1)

Scheme O

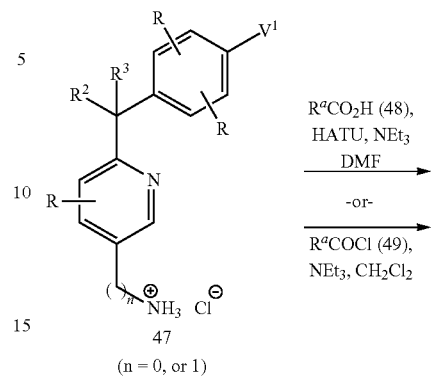
47
(n = 0, or 1)

R^aCO₂H (48), HATU, NEt₃
DMF
—or—
R^aCOCl (49), NEt₃, CH₂Cl₂
→

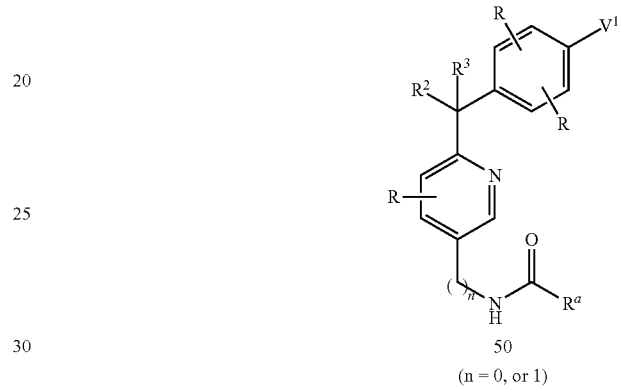
50
(n = 0, or 1)

Reaction scheme O illustrates preferred methods for the syntheses of compounds of type 50. For example, 47 can participate in amide bond coupling reactions with a carboxylic acid of type 48 to afford an amide of structural formula 50, using the reagents and conditions described for the generalized amide coupling protocol shown in reaction Scheme O in the presence of a suitable tertiary amine base, such as triethylamine, or diisopropylethylamine, or the like. Alternatively, 47 may also be treated with an activated ester or acid chloride derivative of type 49, which also affords 50. Typical conditions for effecting such a transformation include treatment of 47 with acid chloride 49 in the presence of excess tertiary amine base such as triethylamine. It is customary to perform the reaction in an inert organic solvent such as DMF or DCM, at temperatures between 0° C. and the reflux temperature of the solvent, frequently at room temperature and for periods of 1-24 hours.

As shown in reaction scheme P, 47 can also be elaborated using the Fukuyama modification of the Mitsunobu reaction (Fukuyama, T.; Jow, C.-K.; Cheung, M. *Tetrahedron Lett.* 1995, 36, 6373-74). For example, 47 may be reacted with an arylsulfonyl chloride such as 2-nitrobenzenesulfonyl chloride, 4-nitrobenzenesulfonyl chloride or 2,4-dinitrobenzenesulfonyl chloride and a tertiary amine base such as 2,4,6-collidine or 2,6-lutidine in an inert organic solvent such as DCM. Alternatively, the reaction can also be performed under the classical Schotten-Baumann conditions as shown in scheme P, in which 47 and the arylsulfonyl chloride are allowed to react in aqueous alkaline solution. The product of this reaction is the sulfonamide of type 51, which can be further modified by reaction with an alcohol of type 52 in the presence of triphenylphosphine and an activating agent such as DEAD, DIAD, or the like. The reaction is performed in a suitable inert organic solvent such as benzene, toluene, THF or mixtures thereof, typically at room temperature, and the reaction is generally complete in 0.5-3 hours. The product of this reaction is the dialkylsulfonamide of type 53, which can be desulfonylated by treatment with either a nucleophilic amine like n-propylamine, in a solvent such as DCM, or with mercaptoacetic acid and triethylamine in DCM. In either case, the reaction is conducted typically at room temperature, for periods of 5 minutes to 1 hour. When a 2- or 4-nitrobenzenesulfonyl derivative is employed, the cleavage of the sulfonamide is accomplished with either the combination of thiophenol and potassium carbonate in a solvent like DMF, or with mercaptoacetic acid and lithium hydroxide in DMF. In either case, the reaction is conducted at room temperature, for periods of 1-3 hours. The secondary amine product of type 54 can be modified further using a variety of methods known in organic synthesis to provide other compounds of the present invention. For example, 54 may be subjected to a reductive amination reaction with an aldehyde or ketone of type 55 using the conditions described in the bottom of reaction Scheme P to afford compounds of type 56.

Scheme P

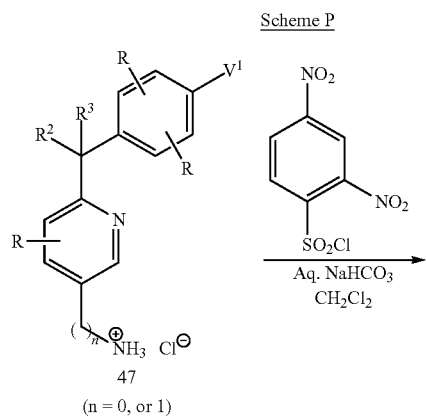

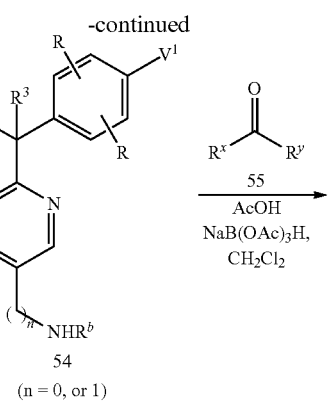

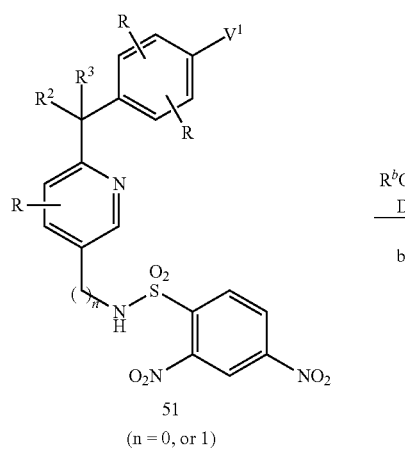

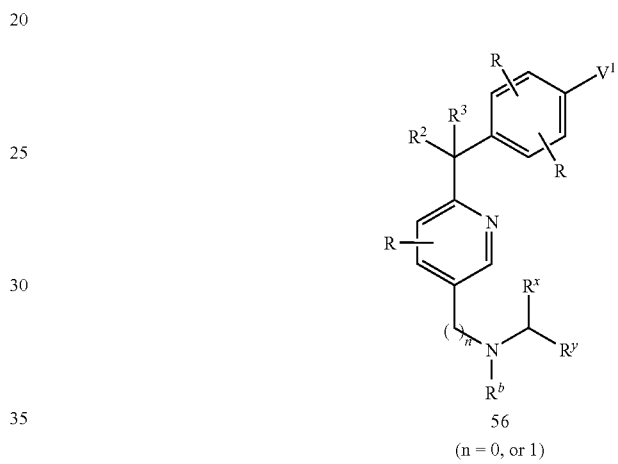

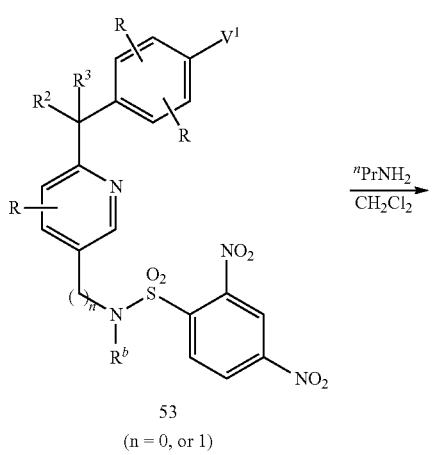

In compound 56, substituent —CHR$^x$R$^y$=a group within the scope of R$^a$ as defined in formula I or a group that can be converted to R$^a$ Scheme Q illustrates in the most generalized manner how compounds of type 57 can be elaborated to a variety of heterocyclic derivatives of structural formula 58 using known methods in organic synthesis. Specific examples of such transformations are shown in the Examples section.

Leading references for effecting such transformations include:

1) Joule, J. A; Mills, K. and Smith, G. F. Heterocyclic Chemistry, Chapman & Hall, 1995, 3rd Edn., and references cited therein;

2) Katritzky, A. R.; Rees, C. W. (Eds), Comprehensive Heterocyclic Chemistry: The Structure, Reactions, Synthesis, and Uses of Heterocyclic Compounds, Pergamon Press, Oxford, 1984, 8v, and references cited therein; and 3) Comprehensive Heterocyclic Chemistry II: Review of the Literature 1982-1995: The Structure, Reactions, Synthesis and Uses of Heterocyclic Compounds, Pergamon Press, New York, 2nd Edn., 1996, 11v, and references cited therein. (Comprehensive Heterocyclic Chemistry, vol. 4-6 Pergamon Press, New York, 1984, and references therein).

4) For compounds shown in Example 1, see: *J. Med. Chem.* 1992, 35, 3691-3698 and references cited therein.

5) For compounds shown in Example 3, see: *Org. Lett.* 2001, 3, 3165-3168 and references cited therein.

Scheme Q

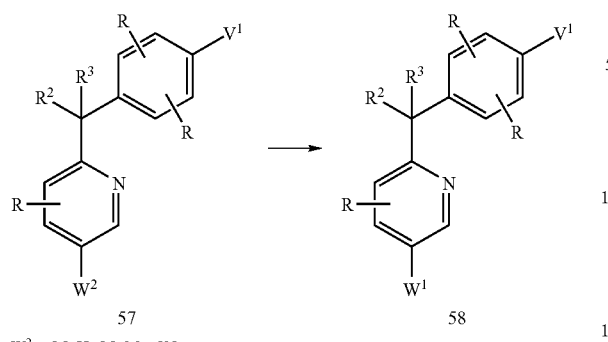

W² = CO₂H, CO₂Me, CN

Scheme R illustrates the preferred method for the resolution of a racemic compound of structural formula 59 in which the asterisked carbon is a center of chirality. Generally, the latter, or intermediates en route to their preparation, may be resolved to afford enantiomerically pure compounds such as 60 and 61 by chiral stationary phase liquid chromatography techniques or other suitable methods known in organic synthesis.

Scheme R

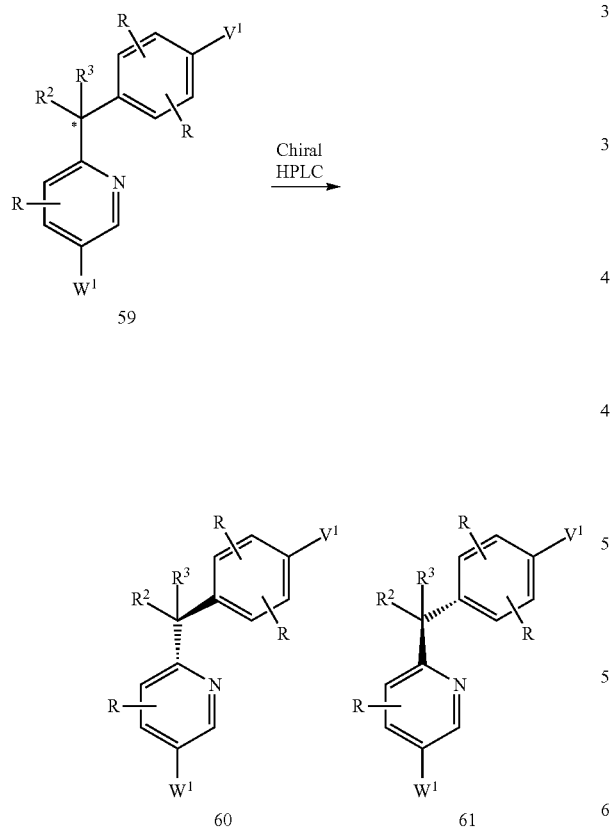

Intermediates used in the synthesis of compounds of this invention can be prepared using the following procedures. In the Tables associated with the following Schemes, compounds having mass spectral data were synthetically prepared.

Scheme i-1

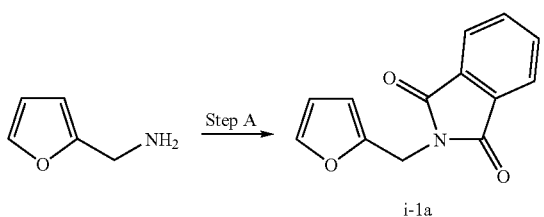

Preparation of i-1a

Step A: Preparation of 2-(2-furylmethyl)-1H-isoindole-1,3(2H)-dione(i-1a)

Furfurylamine (5.70 mL, 61.8 mmol) and phthalic anhydride (10.0 g, 90.9 mmol) were heated to 120° C. for 45 min. The reaction mixture was cooled to rt and treated with EtOH. The resultant suspension was filtered to afford the title compound i-1a as an off-white solid. ¹HNMR (500 MHz, CDCl₃): δ 7.88 (dd, 2H, J=3.2, 5.3 Hz), 7.73 (dd, 2H, J=3.0, 5.5 Hz), 6.38 (d, 1H, J=3.2 Hz), 6.32 (m, 1H), 4.88 (s, 2H).

Scheme i-2

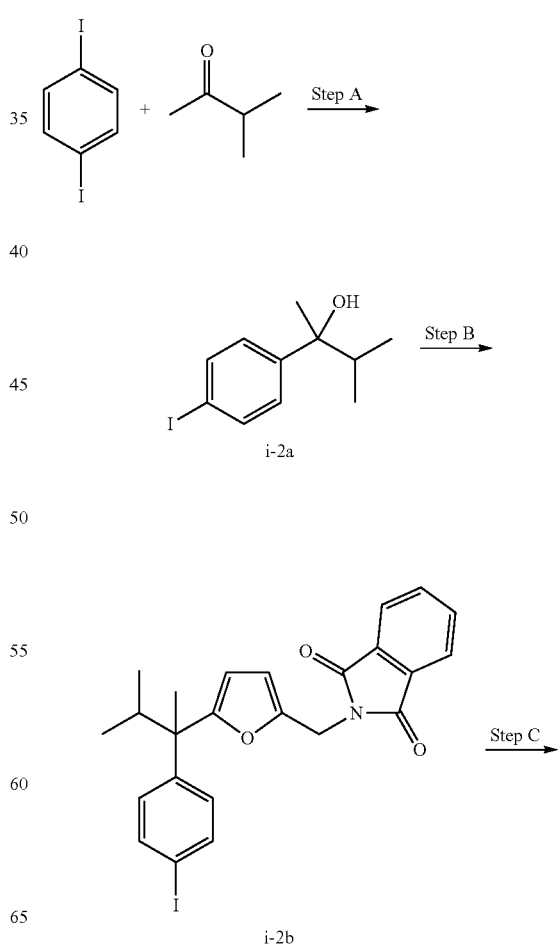

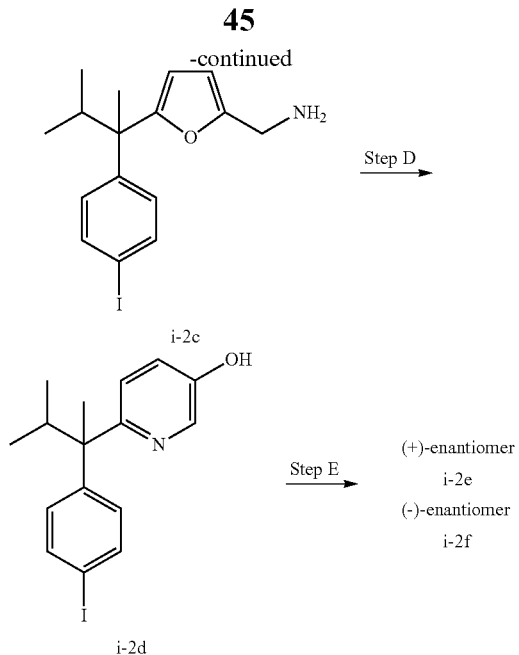

Preparation of i-2e and i-2f

Step A: Preparation of 2-(4-iodophenyl)-3-methylbutan-2-ol (i-2a)

n-Butyllithium (37.0 mL of a 2.5 M solution in hexanes, 92.8 mmol) was added to a stirred solution of 1,4-diiodobenzene (30.0 g, 90.9 mmol) in THF (200 mL) at −78° C. After approximately 20 min, 3-methyl-2-butanone (10.2 mL, 95.5 mmol) was added, and the resulting mixture was allowed to stir at −78° C. for about 1 h. The reaction mixture was poured into aqueous 1N HCl and extracted twice with diethyl ether. The combined organic extracts were washed water and brine, dried (magnesium sulfate) and concentrated in vacuo to afford the title compound i-2a. m/z (ES) 273 (M-OH)$^+$. $^1$HNMR (500 MHz, CDCl$_3$): δ 7.67 (d, 2H, J=8.5 Hz), 7.20 (d, 2H, J=8.7 Hz), 2.00 (m, 1H), 1.52 (s, 3H), 0.92 (d, 3H, J=6.7 Hz), 0.81 (d, 3H, J=6.9 Hz).

Step B: Preparation of 2-({5-[1-(4-iodophenyl)-1,2-dimethylpropyl]-2-furyl}methyl)-1H-isoindole-1,3(2H)-dione (i-2b)

Tetrafluoroboric acid (13.0 mL of a 54% wt solution in diethyl ether, 96.1 mmol) was added to a stirred solution of i-2a (23.2 g, 80.1 mmol) in DCM (200 mL) at −78° C. After approximately 5 min, i-1a (19.1 g, 84.1 mmol) was added in one portion and the resulting suspension stirred at −78° C. for about 15 min. After warming to rt over approximately 2 h, the reaction mixture was quenched cautiously with saturated aqueous sodium bicarbonate, and the organic layer was separated. The aqueous layer was extracted twice with DCM and the combined organic extracts were washed with brine, dried (sodium sulfate) and concentrated in vacuo. The crude residue was purified by flash chromatography on silica gel (gradient elution; 5%-20% EtOAc/hexanes as eluent) to afford the title compound i-2b. m/z (ES) 500 (MH)$^+$. $^1$HNMR (500 MHz, CDCl$_3$): δ 7.88 (dd, 2H, J=3.0, 5.5 Hz), 7.77 (dd, 2H, J=3.0, 5.5 Hz), 7.47 (dd, 2H, J=2.5, 9.0 Hz), 7.06 (dd, 2H, J=2.3, 8.8 Hz), 6.24 (d, 1H, J=3.0 Hz), 6.01 (d, 1H, J=3.0 Hz), 4.85 (m, 2H), 2.58 (m, 1H), 1.50 (s, 3H), 0.82 (d, 3H, J=6.5 Hz), 0.68 (d, 3H, J=6.5 Hz).

Step C: Preparation of 1-{5-[1-(4-iodophenyl)-1,2-dimethylpropyl]-2-furyl}methanamine (i-2c)

Hydrazine monohydrate (27.0 mL, 566 mmol) was added to a stirred solution of i-2b (18.8 g, 37.8 mmol) in EtOH (200 mL). The reaction mixture was heated at reflux for approximately 1 h, then cooled to room temperature and filtered. The residue was washed four times with EtOAc, and the collected filtrate was partially concentrated in vacuo. The resultant solution was washed with water and brine, dried (sodium sulfate) and concentrated in vacuo to afford the title compound i-2c. $^1$HNMR (500 MHz, CDCl$_3$): δ 7.62 (d, 2H, J=8.5 Hz), 7.09 (d, 2H, J=8.7 Hz), 6.06 (m, 2H), 3.81 (s, 2H), 2.58 (m, 1H), 1.55 (s, 3H), 0.92 (d, 3H, J=6.8 Hz), 0.74 (d, 3H, J=6.9 Hz).

Step D: Preparation of 6-[1-(4-iodophenyl)-1,2-dimethylpropyl]pyridin-3-ol (i-2d)

Bromine (32.0 mL of a 1.0 M solution in MeOH) was added dropwise via a pressure equalizing addition funnel to a stirred solution of i-2c (13.9 g, 37.8 mmol) in MeOH (15.0 mL) and water (35.0 mL) at 0° C. After approximately 1 h, the reaction mixture was quenched with saturated aqueous sodium bicarbonate and extracted twice with EtOAc. The combined organic extracts were washed with brine, dried (sodium sulfate), and concentrated in vacuo. The crude residue was purified by flash chromatography on silica gel (gradient elution; 0%-50% EtOAc/hexanes as eluent) to afford the title compound i-2d. m/z (ES) 368 (MH)$^+$. $^1$HNMR (500 MHz, CDCl$_3$): δ 8.11 (m, 1H), 7.55 (d, 2H, J=8.2 Hz), 7.08 (m, 3H), 7.01 (m, 1H), 2.94 (m, 1H), 1.62 (s, 3H), 0.83 (d, 3H, J=6.7 Hz), 0.79 (d, 3H, J=6.8 Hz).

Step E: Preparation of (i-2e) and (i-2f)

Enantiomers i-2e and i-2f were separated using preparative normal phase chiral HPLC. A solution of i-2d in MeOH was injected onto a CHIRALCEL® OD-H (available from Chiral Technologies, Inc., Exton, Pa.) semi-preparative (250×21 mm) HPLC column (eluting with 15% MeOH/CO$_2$ with a column temperature of 40° C. at 50 mL/min with UV detection at 220 nm). The enantiomers were separated with the faster eluting enantiomer i-2e having a retention time of 5.83 min and the slower eluting enantiomer i-2f having a retention time of 6.40 min. The separated fractions were concentrated to provide the enantiomers i-2e and i-2f. The (−)-enantiomer i-2f is preferred for making final products when R$^2$ is i-propyl and R$^3$ is —CH$_3$.

Intermediate 6-[1-(4-iodophenyl)-2,2-dimethylpropyl]pyridin-3-ol (i-2g) can be prepared from pivaldehyde in either racemic or chiral form following procedures similar to those described for preparing intermediates i-2d, i-2e and i-2f.

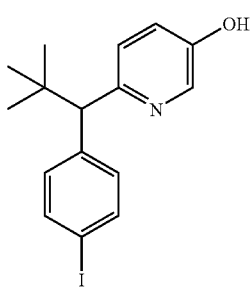

i-2g

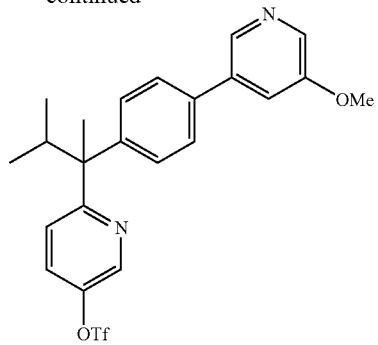

i-3c

Preparation of i-3c

Step A: Preparation of 6-{1,2-dimethyl-1-[4-(4,4,5,5-tetramethyl-1,3,2-dioxaborolan-2-yl)phenyl]propyl}pyridin-3-ol (i-3a)

[1,1'-Bis(diphenylphosphino)ferrocene]dichloropalladium(II) (700 mg, 0.900 mmol) was added to a stirred suspension of i-2f (16.6 g, 45.2 mmol), bis(pinacolato)diboron (12.1 g, 47.5 mmol) and potassium acetate (13.3 g, 136 mmol) in DMSO (150 mL) at rt. The resulting suspension was heated to 80° C. for approximately 2 h. After cooling to rt, the reaction mixture was diluted with EtOAc and filtered through a short column of CELITE®, eluting with EtOAc. The filtrate was washed with saturated aqueous sodium bicarbonate, water and brine, dried (sodium sulfate) and concentrated in vacuo to afford the title i-3a. m/z (ES) 368 (MH)+. $^1$HNMR (500 MHz, CDCl$_3$): δ 8.21 (d, 1H, J=2.8 Hz), 7.71 (d, 2H, J=8.2 Hz), 7.34 (d, 2H, J=82 Hz), 7.06 (d, 1H, J=8.7 Hz), 7.02 (dd, 1H, J=2.8, 8.7 Hz), 3.02 (m, 1H), 1.66 (s, 3H), 1.33 (s, 12H), 0.84 (d, 3H, J=6.6 Hz), 0.78 (d, 3H, J=6.9 Hz).

Step B: Preparation of 6-{1-[4-(5-methoxypyridin-3-yl)phenyl]-1,2-dimethylpropyl}pyridin-3-ol (i-3b)

[1,1'-Bis(diphenylphosphino)ferrocene]dichloropalladium(1) (700 mg, 0.900 mmol) was added to a stirred solution of i-3a (16.6 g, 45.2 mmol), 3-bromo-5-methoxypyridine (10.2 g, 54.2 mmol) and sodium carbonate (68.0 mL of a 2.0 M aqueous solution, 136 mmol) in EtOH:toluene (120 mL of an 80:20 mixture, respectively) at rt. The resulting solution was heated to 95° C. for approximately 4 h. After cooling to rt, the reaction mixture was filtered through a short column of CELITE®, eluting with EtOAc. The filtrate was washed with saturated aqueous sodium bicarbonate, water and brine, dried (sodium sulfate) and concentrated in vacuo. The crude residue was purified by flash chromatography on silica gel (gradient elution; 10%-60% EtOAc/hexanes as eluent) to afford the title compound i-3b. m/z (ES) 349 (MH)+. $^1$HNMR (500 MHz, CDCl$_3$): δ 8.38 (br s, 1H), 8.25 (m, 2H), 7.44 (m, 4H), 7.41 (m, 1H), 7.10 (dd, 1H, J=3.0, 8.7 Hz), 7.06 (dt, 1H, J=2.8, 8.5 Hz), 3.92 (d, 3H, J=0.9 Hz), 3.05 (m, 1H), 1.69 (d, 3H, J=1.4 Hz), 0.88 (dd, 3H, J=1.1, 6.4 Hz), 0.83 (d, 3H, J=6.9 Hz).

Step C: Preparation of 6-{1-[4-(5-methoxypyridin-3-yl)phenyl]-1,2-dimethylpropyl}pyridin-3-yl trifluoromethanesulfonate (i-3c)

2-[N,N-Bis(trifluoromethansulfonyl)amino]pyridine (14.7 g, 41.1 mmol) was added to a stirred solution of i-3b Scheme i-3

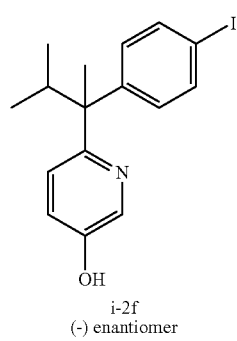

i-2f
(−) enantiomer

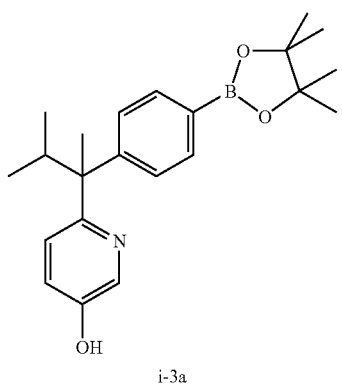

i-3a

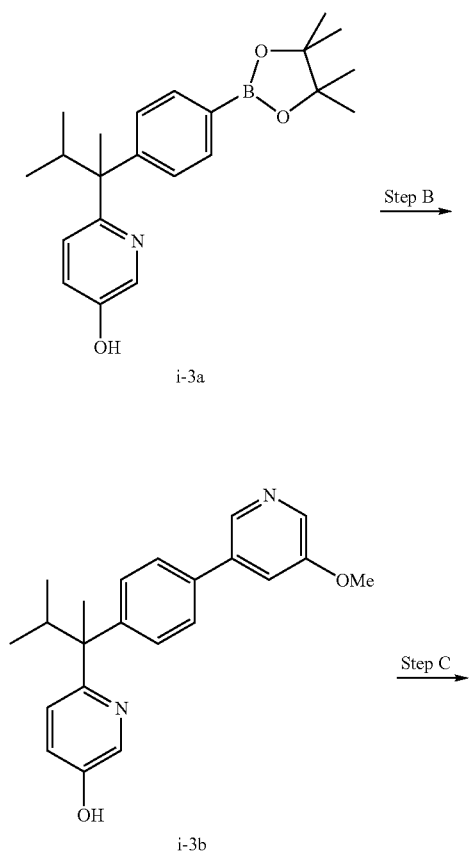

i-3b (13.6 g, 39.1 mmol), triethylamine (7.10 mL, 50.8 mmol) and DMAP (10 mg) in DCM (150 mL) at 0° C. After approximately 30 min, the reaction mixture was poured into saturate aqueous sodium bicarbonate and extracted three times with DCM. The combined organic extracts were washed with water and brine, dried (sodium sulfate) and concentrated in vacuo. The crude residue was purified by flash chromatography on silica gel (gradient elution; 0%-40% EtOAc/hexanes as eluent) to afford the title compound i-3c. m/z (ES) 481 (MH)$^+$. $^1$HNMR (500 MHz, CDCl$_3$): δ 8.59 (d, 1H, J=3.0 Hz), 8.47 (d, 1H, J=1.3 Hz), 8.30 (d, 1H, J=2.5 Hz), 7.53 (d, 2H, J=8.2 Hz), 7.52 (m, 1H), 7.46 (d, 2H, J=8.5 Hz), 7.38 (m, 1H), 7.36 (d, 1H, J=8.9 Hz), 3.94 (s, 3H), 3.13 (m, 1H), 1.76 (s, 3H), 0.87 (d, 3H, J=6.8 Hz), 0.85 (d, 3H, J=6.9 Hz).

Preparation of i-3d, i-3e., i-3f, i-39, and i-3h

Following procedures similar to those described for the preparation of intermediate i-3c, the following additional intermediates i-3d-i-3e and i-3f-i-3h can be prepared from i-2f and i-2g, respectively. For example, intermediate i-3f can be prepared following procedures similar to those described for the preparation of i-3c, but substituting racemic or chiral i-2g in place of i-2f.

Intermediates i-3d and i-3e can be prepared from i-3a following procedures as described in scheme i-3, steps B and C, but substituting 3-chloro-6-(2,5-dimethyl-1H-pyrrol-1-yl) pyridazine or 5-bromo-2-(2,5-dimethyl-1H-pyrrol-1-yl)pyrimidine in place of 3-bromo-5-methoxypyridine. Intermediates i-3g and i-3h can similarly be prepared, but starting with racemic or chiral i-2g.

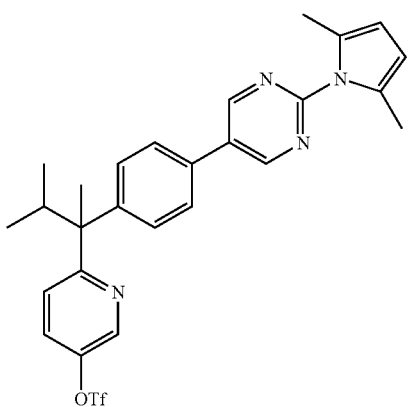
i-3d

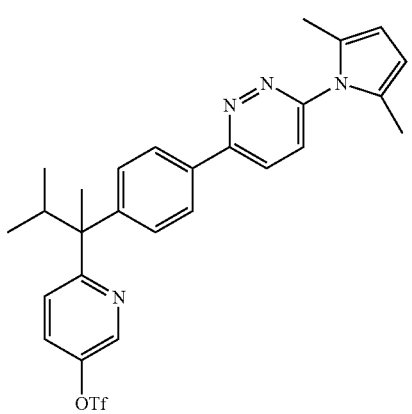
i-3e

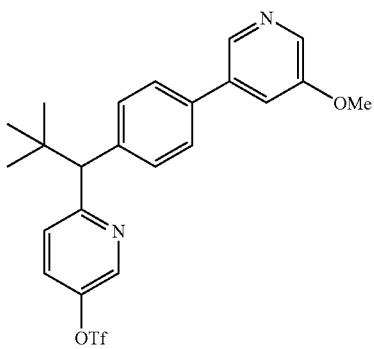
i-3f

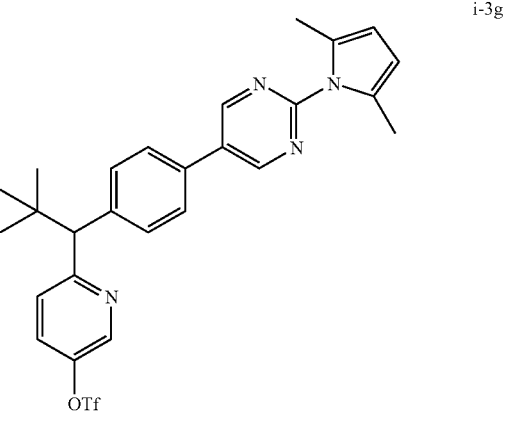 [SMILES: Cc1ccc(C)n1-c1ccc(-c2ccc(C(c3ccc(OS(=O)(=O)C(F)(F)F)cn3)C(C)(C)C)cc2)nn1]
i-3g

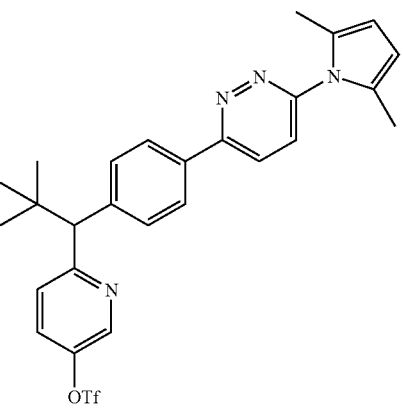
i-3h

For i-3d: m/z (ES) 545 (MH)$^+$. $^1$HNMR (500 MHz, CDCl$_3$): δ 8.96 (s, 2H), 8.63 (d, 1H, J=2.7 Hz), 7.58 (m, 1H), 7.57 (d, 2H, J=8.3 Hz), 7.52 (d, 2H, J=8.4 Hz), 7.41 (d, 1H, J=8.7 Hz), 5.94 (s, 2H), 3.16 (m, 1H), 2.39 (s, 6H), 1.79 (s, 3H), 0.89 (d, 3H, J=6.7 hz), 0.86 (d, 3H, J=6.7 Hz).

For i-3e: m/z (ES) 545 (MH)$^+$.

Preparation of i-3d

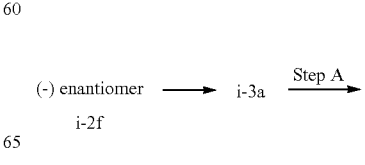

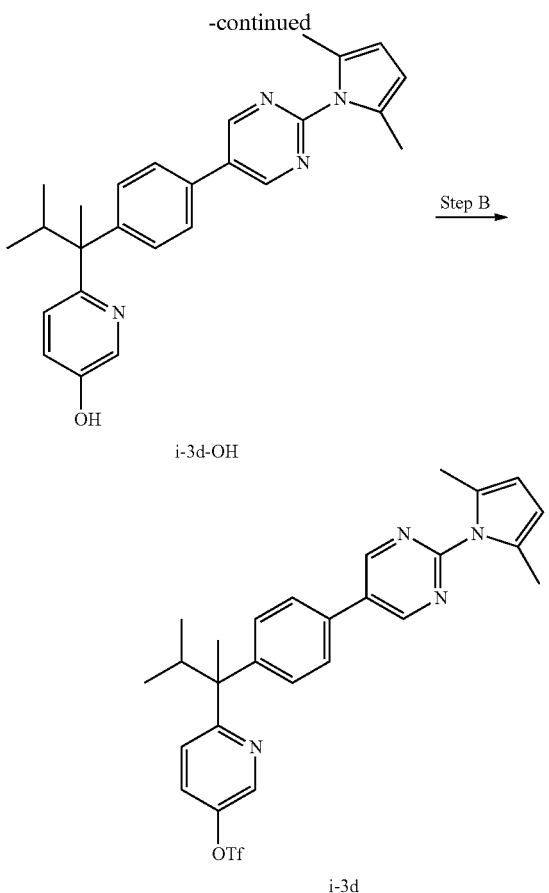

crude residue was purified by flash chromatography on silica gel (gradient elution; 30%-80% EtOAc/hexanes as eluent) to afford i-3d. m/z (ES) 545 (MH)⁺. ¹HNMR (500 MHz, CDCl₃): δ 8.97 (s, 2H), 8.61 (d, 1H, J=3.0 Hz), 7.57 (d, 2H, J=8.4 Hz), 7.53 (m, 1H), 7.53 (d, 2H, J=8.0 Hz), 7.37 (d, 1H, J=8.7 Hz), 5.95 (s, 2H), 3.15 (m, 1H), 2.41 (s, 6H), 1.78 (s, 3H), 0.89 (d, 3H, J=6.7 Hz), 0.86 (d, 3H, J=6.9 Hz).

Preparation of 3-chloro-6-(2,5-dimethyl-1H-pyrrol-1-yl)pyridazine and 5-bromo-2-(2,5-dimethyl-1H-pyrrol-1-yl)pyrimidine

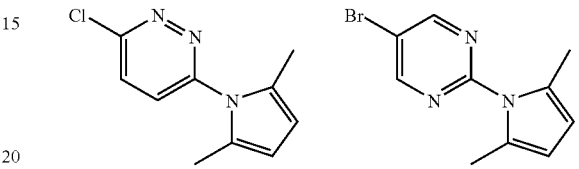

A mixture of p-TSA (117 mg, 0.618 mmol), 2,5-hexanedione (4.36 mL, 37.1 mmol) and 3-amino-6-chloropyridazine (4.00 g, 30.9 mmol) in toluene (150 mL) was heated at 140° C. for 5 h in a round bottom flask equipped with a condenser and Dean-Stark apparatus. The reaction mixture was cooled to rt and charcoal was added. The mixture was filtered through Celite® and concentrated in vacuo to afford the title compound i-3e. m/z (ES) 208 (MH)⁺.

5-bromo-2-(2,5-dimethyl-1H-pyrrol-1-yl)pyrimidine was prepared following the procedure as described above but substituting 2-amino-5-bromopyrimidine for 3-amino-6-chloropyridazine. m/z (ES) 252 (MH)⁺.

Scheme i-4

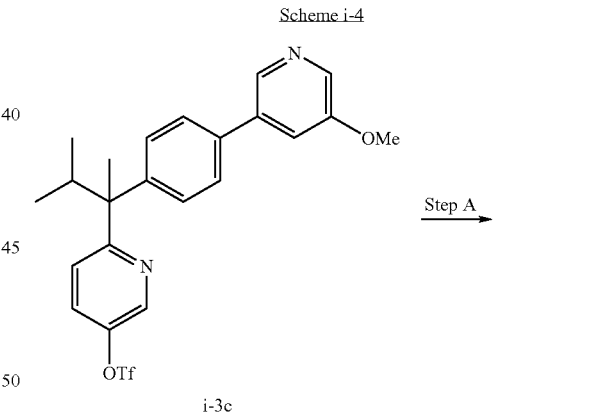

Step A: Preparation of 6-(1-{-4-[2-(2,5-dimethyl-1H-pyrrol-1-yl)pyrimidin-5-yl]phenyl}-1,2-dimethylpropyl)pyridin-3-ol (i-3d-OH)

[1,1'-Bis(diphenylphosphino)ferrocene]dichloropalladium(II) (3.01 g, 3.69 mmol) was added to a stirred solution of i-3a (13.9 g, 37.9 mmol), 5-bromo-2-(2,5-dimethyl-1H-pyrrol-1-yl)pyrimidine (10.5 g, 41.6 mmol) and sodium carbonate (57.0 mL of a 2.0 M aqueous solution, 114 mmol) in EtOH:toluene (250 mL of an 80:20 mixture, respectively) at rt. The resulting solution was heated to 100° C. for approximately 1.5 h. After cooling to rt, the reaction mixture was filtered through a short column of CELITE®, eluting with EtOAc. The filtrate was washed with saturated aqueous ammonium chloride and brine, dried (sodium sulfate) and concentrated in to afford the title compound i-3d-OH. m/z (ES) 413 (MH)⁺.

Step B: Preparation of 6-(1-{4-[2-(2,5-dimethyl-1H-pyrrol-1-yl)pyrimidin-5-yl]phenyl}-1,2-dimethylpropyl)pyridin-3-yl trifluoromethanesulfonate (i-3d)

2-[N,N-Bis(trifluoromethansulfonyl)amino]pyridine (13.2 g, 37.0 mmol) was added to a stirred solution of i-3d-OH (15.6 g, 37.9 mmol), triethylamine (6.50 mL, 46.6 mmol) and DMAP (256 mg, 2.10 mmol) in DCM (270 mL) at 0° C. After approximately 2 h, the reaction mixture was poured into saturated aqueous sodium bicarbonate and extracted three times with EtOAc. The combined organic extracts were washed with saturated aqueous sodium bicarbonate and brine, dried (sodium sulfate) and concentrated in vacuo. The

Preparation of i-4-a

Step A: Preparation of methyl 6-{1-[4-(5-methoxyayridin-3-yl)phenyl]-1,2-dimethylpropyl}nicotinate (i-4-a)

Palladium (II) acetate (6.00 mg, 0.0260 mmol) and 1,1'-bis(diphenylphosphino)ferrocene (28.0 mg, 0.0520 mmol) were added successively to a stirred solution of i-3c (82.0 mg, 0.171 mmol) in triethylamine:DMF:methanol (2.20 mL of a 1:10:10 mixture, respectively) at rt. The reaction mixture was saturated with carbon monoxide and then heated to 75° C. under a carbon monoxide atmosphere (balloon) for approximately 6 h. After cooling to rt, the reaction mixture was filtered through a short column of CELITE®, eluting with EtOAc. The filtrate was washed with water and brine, dried (sodium sulfate) and concentrated in vacuo. Purification of the crude residue by flash chromatography on silica gel (gradient elution; 15%-35% EtOAc/hexanes as eluent) afforded the title compound i-4-a. m/z (ES) 391 (MH)$^+$. $^1$HNMR (500 MHz, CDCl$_3$): δ 9.22 (d, 1H, J=1.6 Hz), 8.46 (s, 1H), 8.29 (d, 1H, J=2.5 Hz), 8.17 (dd, 1H, J=1.1, 8.5 Hz), 7.50 (m, 4H), 7.35 (m, 2H), 3.95 (s, 3H), 3.92 (d, 3H, J=1.6 Hz), 3.19 (m, 1H), 1.77 (s, 3H), 0.88 (d, 3H, J=6.6 Hz), 0.86 (d, 3H, J=6.9 Hz).

Following procedures similar to those described for the preparation of intermediate i-4a, the following additional intermediates i-4b-f can be prepared from i-3d-h, respectively.

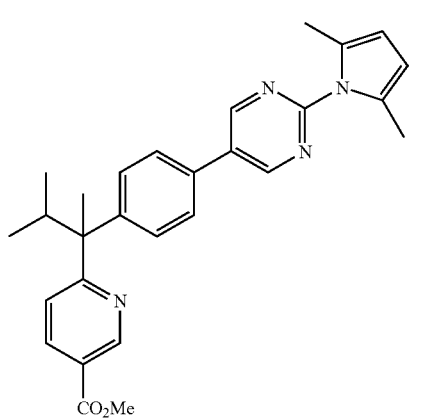

i-4b

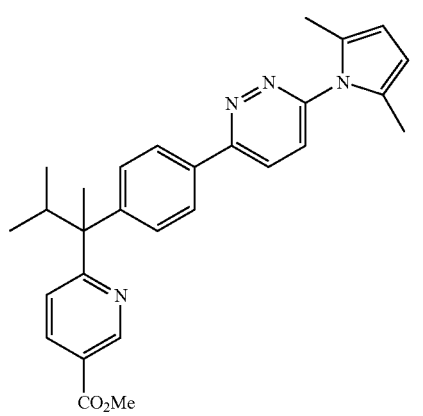

i-4c

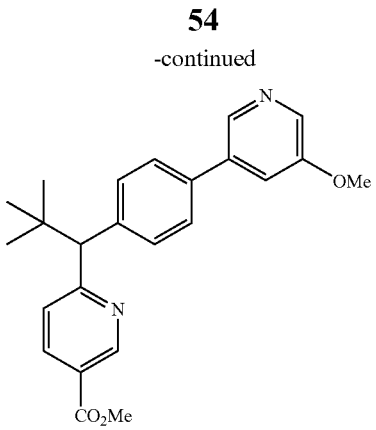

i-4d

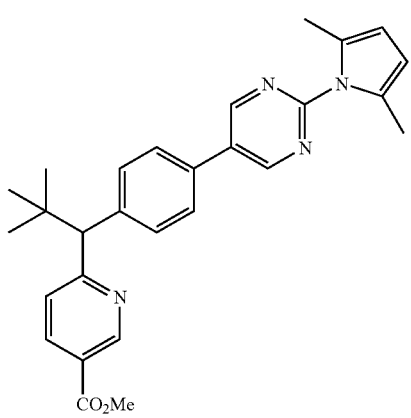

i-4e

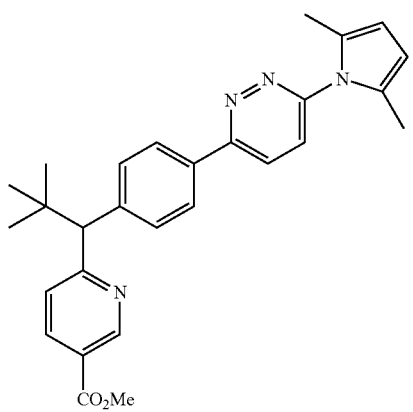

i-4f

For i-4c: m/z (ES) 455 (MH)$^+$. $^1$HNMR (500 MHz, CDCl$_3$): δ 9.22 (d, 1H, J=2.3 Hz), 8.16 (1H, dd, J=2.2, 8.4 Hz), 8.06 (2H, d, J=8.4 Hz), 7.97 (1H, d, J=8.9 Hz), 7.55 (2H, d, J=8.7 Hz), 7.45 (1H, d, J=8.9 Hz), 7.34 (1H, d, J=8.5 Hz), 5.99 (2H, s), 3.94 (3H, s), 3.20 (1H, m), 2.21 (6H, s), 1.78 (3H, s), 0.88 (3H, d, J=6.7 Hz), 0.85 (3H, d, J=6.6 Hz).

Scheme i-5

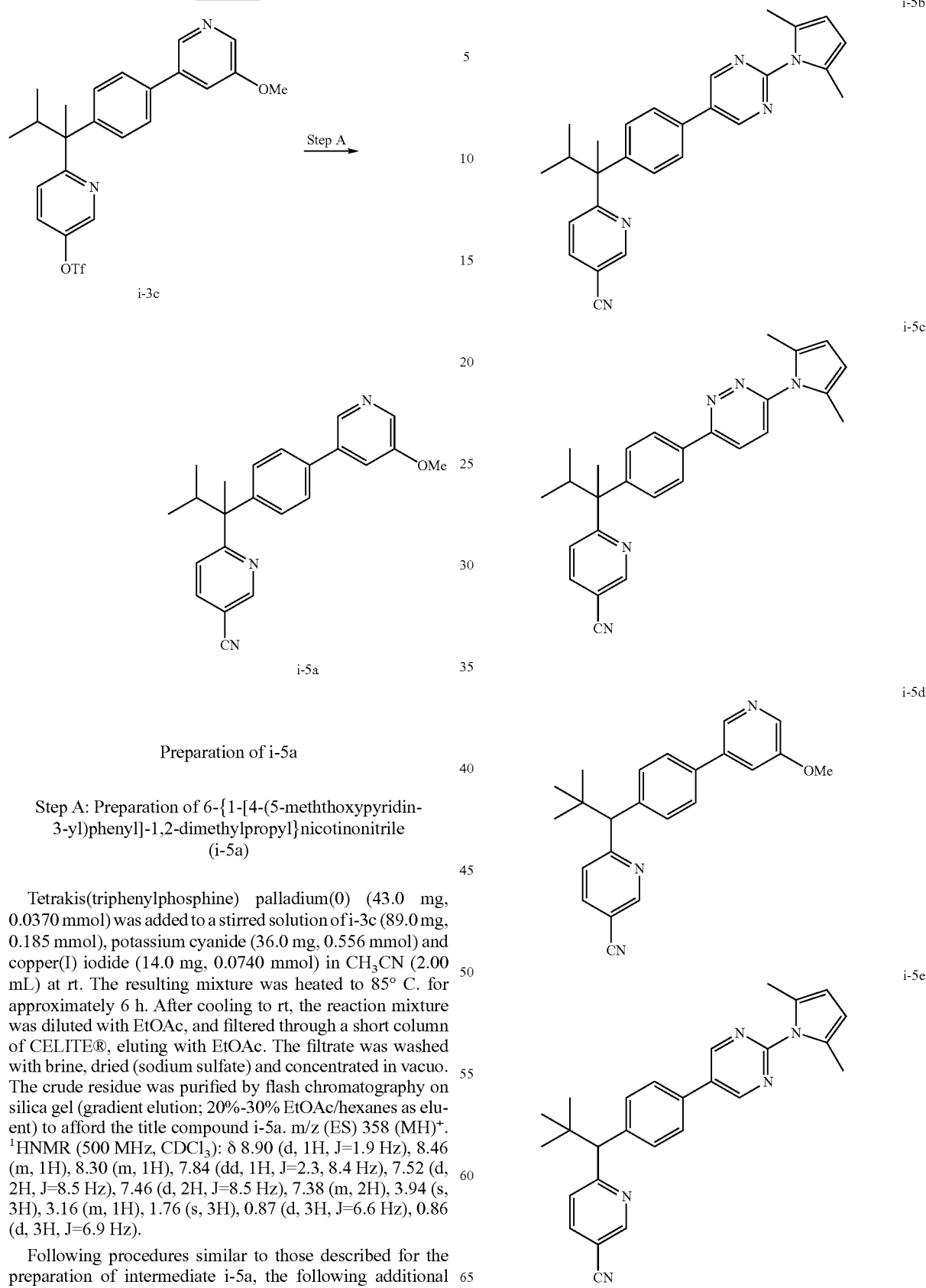

Preparation of i-5a

Step A: Preparation of 6-{1-[4-(5-meththoxypyridin-3-yl)phenyl]-1,2-dimethylpropyl}nicotinonitrile (i-5a)

Tetrakis(triphenylphosphine) palladium(0) (43.0 mg, 0.0370 mmol) was added to a stirred solution of i-3c (89.0 mg, 0.185 mmol), potassium cyanide (36.0 mg, 0.556 mmol) and copper(I) iodide (14.0 mg, 0.0740 mmol) in CH$_3$CN (2.00 mL) at rt. The resulting mixture was heated to 85° C. for approximately 6 h. After cooling to rt, the reaction mixture was diluted with EtOAc, and filtered through a short column of CELITE®, eluting with EtOAc. The filtrate was washed with brine, dried (sodium sulfate) and concentrated in vacuo. The crude residue was purified by flash chromatography on silica gel (gradient elution; 20%-30% EtOAc/hexanes as eluent) to afford the title compound i-5a. m/z (ES) 358 (MH)$^+$. $^1$HNMR (500 MHz, CDCl$_3$): δ 8.90 (d, 1H, J=1.9 Hz), 8.46 (m, 1H), 8.30 (m, 1H), 7.84 (dd, 1H, J=2.3, 8.4 Hz), 7.52 (d, 2H, J=8.5 Hz), 7.46 (d, 2H, J=8.5 Hz), 7.38 (m, 2H), 3.94 (s, 3H), 3.16 (m, 1H), 1.76 (s, 3H), 0.87 (d, 3H, J=6.6 Hz), 0.86 (d, 3H, J=6.9 Hz).

Following procedures similar to those described for the preparation of intermediate i-5a, the following additional intermediates i-5b-f can be prepared from i-3d-h, respectively.

-continued

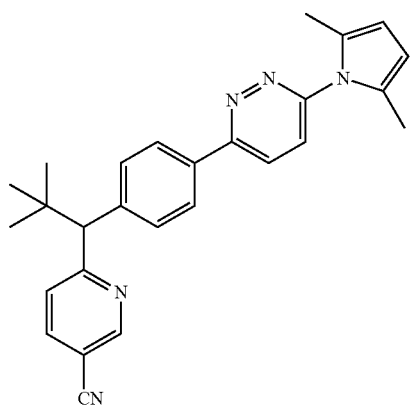

i-5f

Scheme i-6

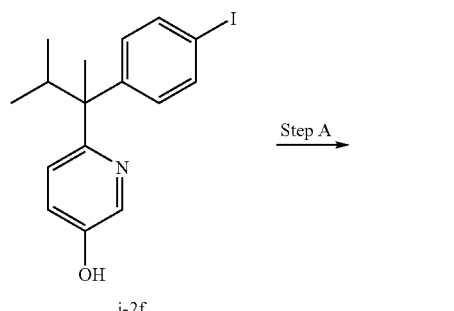

i-2f

Step A →

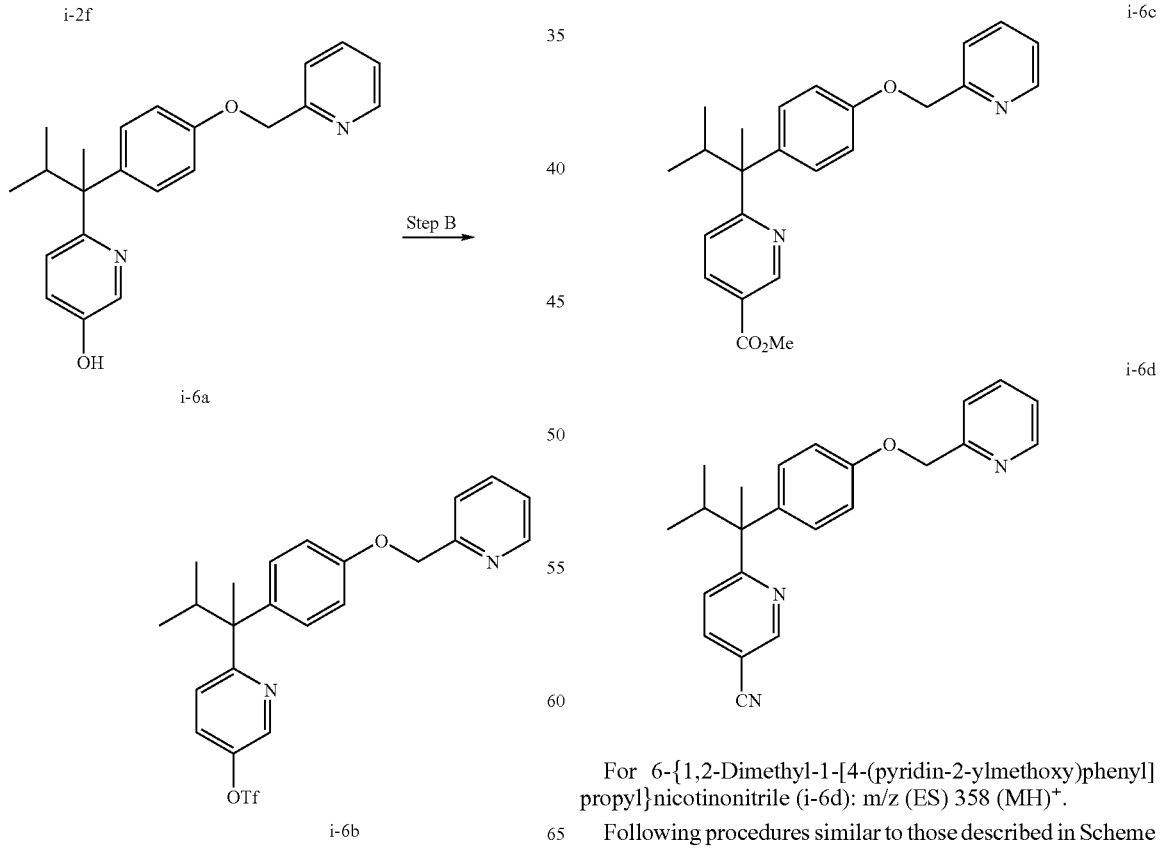

i-6a

Step B → i-6b

Preparation of i-6a and i-6b

Step A: Preparation of 6-{1,2-dimethyl-1-[4-(pyridin-2-ylmethoxy)phenyl]propyl}pyridin-3-ol (i-6a)

A neat mixture of 2-pyridinemethanol (442 µL, 4.58 mmol), copper (I) iodide (38.0 mg, 0.200 mmol), 1,10-phenanthroline (72.0 mg, 0.200 mmol), cesium carbonate (1.30 g, 3.99 mmol) and i-2f (310 mg, 0.845 mmol) was heated to 110° C. for approximately 20 h. After cooling to rt, the reaction was poured into brine, and the resulting suspension was filtered. The filter cake was dissolved in ether, and washed twice with brine, dried (magnesium sulfate) and concentrated in vacuo. The crude residue was purified by flash chromatography on silica gel (gradient elution; 40%-70% EtOAc/hexanes as eluent) to afford the title compound i-6a. m/z (ES) 349 (MH)+.

Step B: Preparation of 6-{1,2-dimethyl-1-[4-(pyridin-2-ylmethoxy)phenyl]propyl}pyridin-3-yl trifluoromethanesulfonate (i-6b)

Compound i-6b was prepared following a similar procedure to that described for the preparation of i-3c from i-3b. m/z (ES) 481 (MH)+.

Compounds i-6c and i-6d can be prepared following similar procedures to those described in Step A of Scheme i-4 and Step A of Scheme i-5, respectively.

For 6-{1,2-Dimethyl-1-[4-(pyridin-2-ylmethoxy)phenyl]propyl}nicotinonitrile (i-6d): m/z (ES) 358 (MH)+.

Following procedures similar to those described in Scheme i-6, the following additional compounds represented in Table i-6 can be prepared:

TABLE i-6 i-6A
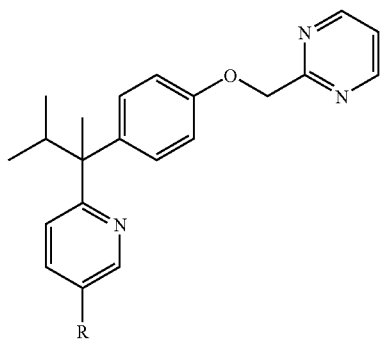

i-6B
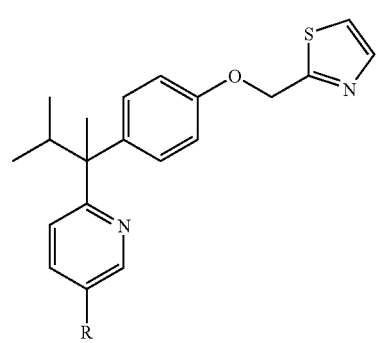

i-6C
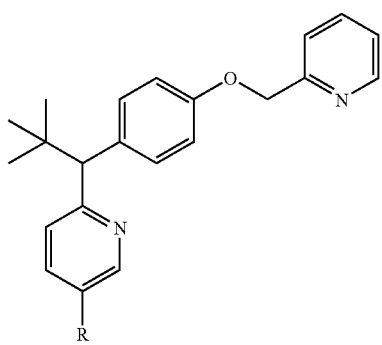

i-6D
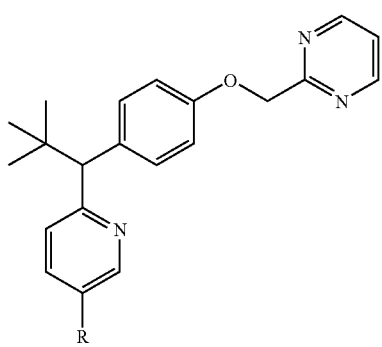

TABLE i-6-continued i-6E

| Ex. i-6A | Ex. i-6B | Ex. i-6C | Ex. i-6D | Ex. i-6E | R |
|---|---|---|---|---|---|
| a | a | a | a | a | —CO$_2$Me |
| b | b | b | b | b | —CN |

For 6-{1,2-Dimethyl-1-[4-(1,3-thiazol-2-ylmethoxy)phenyl]propyl}nicotinonitrile (i-6Bb): m/z (ES) 364 (MH)$^+$.

For Methyl 6-{2,2-dimethyl-1-[4-(pyridin-2-ylmethoxy)phenyl]propyl}nicotinate (i-6Ca): m/z (ES) 391 (MH)$^+$.

For 6-{2,2-Dimethyl-1-[4-(pyridin-2-ylmethoxy)phenyl]propyl}nicotinonitrile (i-6Cb): m/z (ES) 358 (MH)$^+$.

Scheme i-7

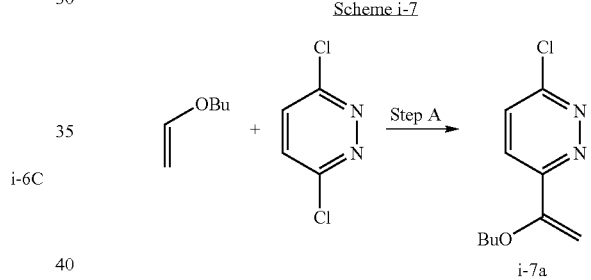

Preparation of 3-(1-butoxyvinyl)-6-chloropyridazine (i-7a)

THF (24.0 mL) was added rapidly dropwise to tert-butyllithium (150 mL of a 1.7 M solution in pentane) at −78° C. After 15 min, n-butyl vinyl ether (14.0 mL, 109.4 mmol) was added, and the resulting mixture was warmed to −30° C., at which point modest gas evolution was observed. As gas evolution ceased, a second portion of n-butyl vinyl ether (14.0 mL, 109.4 mmol) was added, maintaining the reaction temperature at −30° C. After gas evolution had ceased, the reaction mixture was cooled to −78° C., and a solution of zinc chloride (29.8 g, 219 mmol) in THF (250 mL) was added rapidly dropwise. After 15 min, the reaction was warmed to −10° C. and transferred via cannula to a stirred solution of 3,6-dichloropyridazine (32.6 g, 219 mmol) and [1,1'-bis(diphenylphosphino)ferrocene]dichloropalladium(II) (16.0 g, 21.9 mmol) in THF (200 mL) at 0° C. After 1 h at 0° C., the reaction mixture was diluted with EtOAc and filtered through a short column of CELITE®, eluting with EtOAc. The filtrate was washed with water and brine, dried (sodium sulfate), and concentrated in vacuo. The crude residue was purified by flash chromatography on silica gel (gradient elution; 0%-15% EtOAc/hexanes as eluent) to afford the title compound i-7a.

$^1$HNMR (500 MHz, CDCl$_3$): δ 7.80 (d, 1H, J=8.9 Hz), 7.52 (d, 1H, J=8.9 Hz), 5.76 (d, 1H, J=2.5 Hz), 4.55 (d, 1H, J=2.5 Hz), 3.97 (t, 2H, J=6.4 Hz), 1.83 (m, 2H), 1.57 (m, 2H), 1.02 (t, 3H, J=7.5 Hz).
In the Tables in the following Examples, compounds having mass spectral data were synthetically prepared.
Example 1
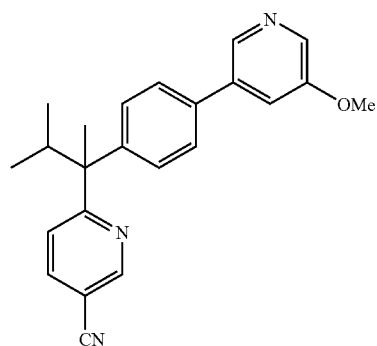
i-5a
Step A
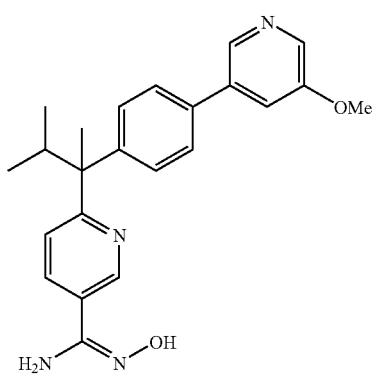
1a
Step B
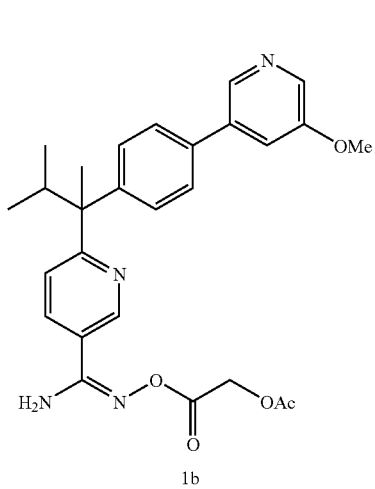
1b
Step C
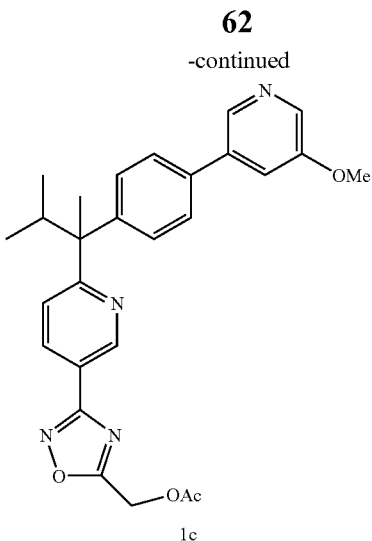
1c
Step D
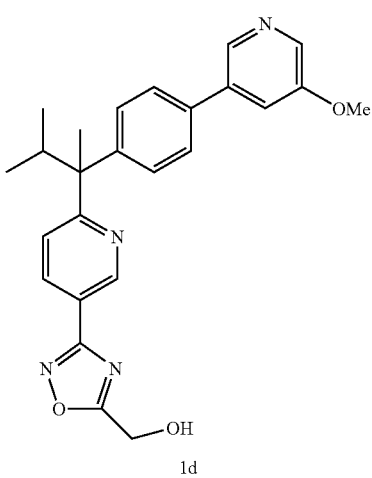
1d
Step E
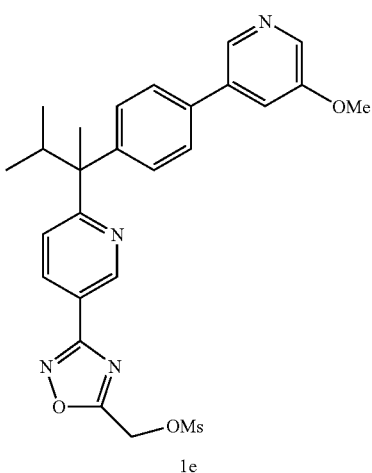
1e
Step F

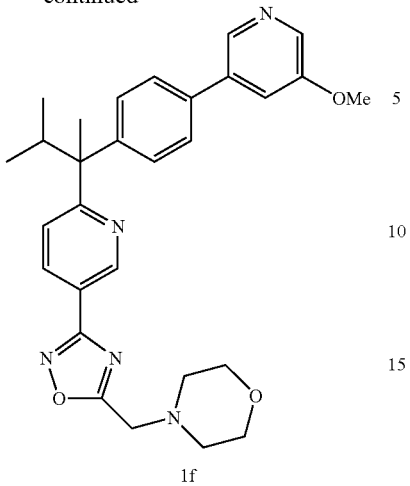

Preparation of 1f

Step A: Preparation of N'-hydroxy-6-{1-[4-(5-methoxypyridin-3-yl)phenyl]-1,2-dimethylpropyl}pyridine-3-carboximidamide (1a)

Hydroxylamine (378 μL of a 50% solution in $H_2O$, 5.75 mmol) was added to a stirred solution of i-5a (685 mg, 1.92 mmol) in EtOH (17.0 mL) at rt, and the resulting reaction mixture was heated to 80° C. for approximately 2 h. After cooling to rt, the reaction mixture was concentrated in vacuo, and the crude residue was purified by flash chromatography on silica gel (gradient elution; 0%-7% methanol/DCM as eluent) to afford the title compound 1a. m/z (ES) 391 (MH)$^+$. $^1$HNMR (500 MHz, CD$_3$OD): δ 8.78 (d, 1H, J=2.0 Hz), 8.36 (d, 1H, J=1.8 Hz), 8.19 (d, 1H, J=2.7 Hz), 7.91 (dd, 1H, J=2.4, 8.3 Hz), 7.59 (m, 3H), 7.49 (d, 2H, J=8.4 Hz), 7.42 (d, 1H, J=8.5 Hz), 3.93 (s, 3H), 3.16 (m, 1H), 1.74 (s, 3H), 0.88 (d, 3H, J=6.7 Hz), 0.85 (d, 3H, J=6.9 Hz).

Step B: Preparation of 2-({[(1E)-amino(6-{1-[4-(5-methoxypyridin-3-yl)phenyl]-1,2-dimethylpropyl}pyridin-3-yl)methylene]amino}oxy)-2-oxoethyl acetate (1b)

Compound 1a (350 mg, 0.896 mmol) was added to a stirred solution of acetoxyacetic acid (126 mg, 1.07 mmol), 1[3-(dimethylamino)propyl]-3-ethylcarbodiimide hydrochloride (205 mg, 1.07 mmol) and 1-hydroxybenzotriazole (157 mg, 1.16 mmol) in DCM (8.00 mL) at rt. After approximately 1 h, the reaction mixture was poured into saturated aqueous sodium bicarbonate and extracted with EtOAc. The combined organic extracts were washed with water and brine, dried (sodium sulfate) and concentrated in vacuo to afford the title compound 1b, which was used without further purification in the subsequent reaction. m/z (ES) 491 (MH)$^+$ $^1$HNMR (500 MHz, CDCl$_3$): δ 8.90 (s, 1H), 8.51 (s, 1H), 8.29 (s, 1H), 7.92 (d, 1H, J=8.5 Hz), 7.83 (s, 1H), 7.54 (d, 2H, J=8.0 Hz), 7.50 (d, 2H, J=8.0 Hz), 7.35 (d, 1H, J=8.3 Hz), 5.21 (br, 2H), 4.90 (s, 2H), 4.03 (s, 3H), 3.17 (m, 1H), 2.22 (s, 3H), 1.76 (s, 3H), 0.88 (d, 3H, J=6.4 Hz), 0.84 (d, 3H, J=6.6 Hz).

Step C: Preparation of [3-(6-{1-[4-(5-methoxypyridin-3-yl)phenyl]-1,2-dimethylpropyl}pyridin-3-yl)-1,2,4-oxadiazol-5-yl]methyl acetate (1c)

A solution of 1b (0.896 mmol) in xylene (6.00 mL) was heated to 110° C. for approximately 1 h. After cooling to rt, the reaction mixture was concentrated in vacuo to afford the title compound 1c, which was used without further purification in the subsequent reaction. m/z (ES) 473 (MH)$^+$.

Step D: Preparation of [3-(6-{1-[4-(5-methoxypyridin-3-yl)phenyl]-1,2-dimethylpropyl}pyridin-3-yl)-1,2,4-oxadiazol-5-yl]methanol (1d)

A mixture of potassium carbonate (743 mg, 5.38 mmol) in water (1.00 mL) was added to a stirred solution of 1c (0.896 mmol) in methanol (3.00 mL) at rt. After approximately 1 h, the reaction mixture was poured into saturated aqueous sodium bicarbonate and extracted three times with EtOAc. The combined organic extracts were washed with water and brine, dried (sodium sulfate) and concentrated in vacuo. The crude residue was purified by flash chromatography on silica gel (gradient elution; 0%-6% methanol/DCM as eluent) to furnish the title compound 1d. m/z (ES) 431 (MH)$^+$. $^1$HNMR (500 MHz, CD$_3$OD): δ 9.19 (d, 1H, J=2.1 Hz), 8.65 (d, 1H, J=1.4 Hz), 8.46 (d, 1H, J=2.5 Hz), 8.32 (dd, 1H, J=2.2, 8.5 Hz), 8.24 (m, 1H), 7.72 (d, 2H, J=8.4 Hz), 7.62 (d, 2H, J=8.4 Hz), 7.59 (d, 1H, J=8.7 Hz), 4.88 (s, 2H), 4.07 (s, 3H), 3.24 (m, 1H), 1.80 (s, 3H), 0.91 (d, 3H, J=6.6 Hz), 0.87 (d, 3H, J=6.8 Hz).

Step E: Preparation of [3-(6-{1-[4-(5-methoxypyridin-3-yl)phenyl]-1,2-dimethylpropyl}pyridin-3-yl)-1,2,4-oxadiazol-5-yl]methyl methanesulfonate (1e)

Methanesulfonyl chloride (28.0 μL, 0.362 mmol) was added to a stirred solution of 1d (104 mg, 0.241 mmol) and N,N-diisopropylethylamine (105 μL, 0.602 mmol) in DCM (2.00 mL) at 0° C. After approximately 20 min, the reaction mixture was poured into water and extracted three times with EtOAc. The combined organic extracts were washed with water and brine, dried (sodium sulfate) and concentrated in vacuo to afford the title compound 1e, which was used without further purification.

Step F: Preparation of 4-{[3-(6-{1-[4-(5-methoxypyridin-3-yl)phenyl]-1,2-dimethylpropyl}pyridin-3-yl)-1,2,4-oxadiazol-5-yl]methyl}morpholine (1f)

Morpholine (70.0 μL, 0.803 mmol) was added to a stirred solution of 3e (0.0803 mmol) in DMF (800 mL) at rt. After approximately 1 h, the reaction mixture was poured into saturated aqueous sodium bicarbonate and extracted three times with EtOAc. The organic extracts were washed with water and brine, dried (sodium sulfate) and concentrated in vacuo. The crude residue was purified by preparative reversed phase HPLC on YMC Pack Pro C18 stationary phase (CH$_3$CN/H$_2$O as eluent, 0.05% TFA as modifier), followed by lyophilization of the purified fractions to afford the title compound 1f. m/z (ES) 500 (MH)$^+$. $^1$HNMR (500 MHz, CD$_3$OD): δ 9.20 (d, 1H, J=2.1 Hz), 8.62 (s, 1H), 8.40 (m, 1H), 8.33 (dd, 1H, J=2.3, 8.5 Hz), 8.17 (m, 1H), 7.71 (d, 2H, J=8.3 Hz), 7.61 (d, 2H, J=8.4 Hz), 7.60 (d, 1H, J=8.3 Hz), 4.31 (s, 2H), 4.06 (s, 3H), 3.82 (m, 4H), 3.24 (m, 1H), 2.98 (m, 4H), 1.80 (s, 3H), 0.91 (d, 3H, J=6.6 Hz), 0.87 (d, 3H, J=6.8 Hz).

Following procedures similar to those described in Example 1, the following additional compounds represented in Table 1 can be prepared:

TABLE 1

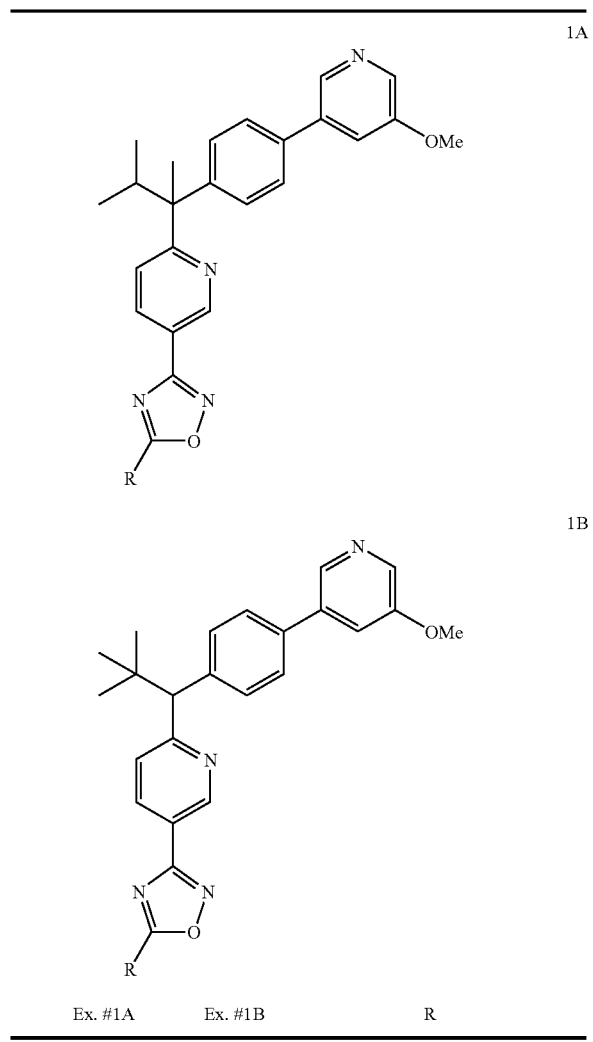

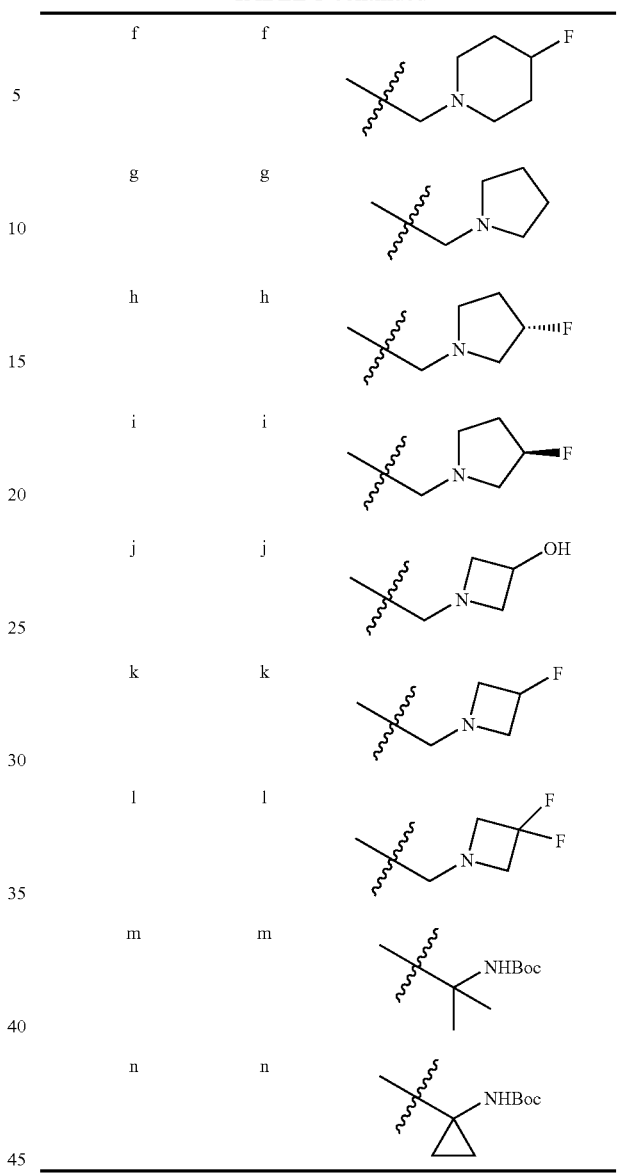

Table 1. Parent Ion m/z (MH)+ data for compounds

For 2-[3-(6-{1-[4-(5-methoxypyridin-3-yl)phenyl]-1,2-dimethylpropyl}pyridin-3-yl)-1,2,4-oxadiazol-5-yl]propan-2-ol (1Ac): m/z (ES) 457 (MH)+.

For 2-{1-[4-(5-methoxypyridin-3-yl)phenyl]-1,2-dimethylpropyl}-5-[5-(piperidin-1-ylmethyl)-1,2,4-oxadiazol-3-yl]pyridine (1Ae): m/z (ES) 498 (MH)+.

For 5-{5-[(4-fluoropiperidin-1-yl)methyl]-1,2,4-oxadiazol-3-yl}-2-{1-[4-(5-methoxypyridin-3-yl)phenyl]-1,2-dimethylpropyl}pyridine m/z (ES) 516 (MH)+.

For 2-{1-[4-(5-methoxypyridin-3-yl)phenyl]-1,2-dimethylpropyl}-5-[5-(pyrrolidin-1-ylmethyl)-1,2,4-oxadiazol-3-yl]pyridine (1Ag): m/z (ES) 484 (MH)+.

For 5-(5-{[(3S)-3-fluoropyrrolidin-1-yl]methyl}-1,2,4-oxadiazol-3-yl)-2-{1-[4-(5-methoxypyridin-3-yl)phenyl]-1,2-dimethylpropyl}pyridine (1Ah): m/z (ES) 502 (MH)+.

For 5-(5-{[(3R)-3-fluoropyrrolidin-1-yl]methyl}-1,2,4-oxadiazol-3-yl)-2-{1-[4-(5-methoxypyridin-3-yl)phenyl]-1,2-dimethylpropyl}pyridine (1Ai): m/z (ES) 502 (MH)+.

For tert-butyl {1-[3-(6-{1-[4-(5-methoxypyridin-3-yl)phenyl]-1,2-dimethylpropyl}pyridin-3-yl)-1,2,4-oxadiazol-5-yl]-1-methylethyl}carbamate (1Am): m/z (ES) 558 (MH)+.

For tert-butyl {1-[3-(6-{1-[4-(5-methoxypyridin-3-yl)phenyl]-1,2-dimethylpropyl}pyridin-3-yl)-1,2,4-oxadiazol-5-yl]cyclopropyl}carbamate (1An): m/z (ES) 556 (MH)+.

Example 2

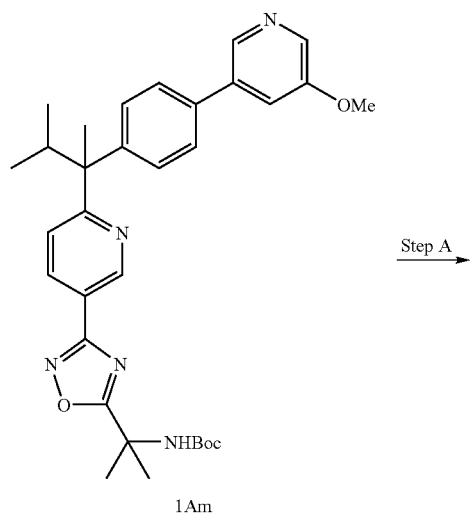

1Am

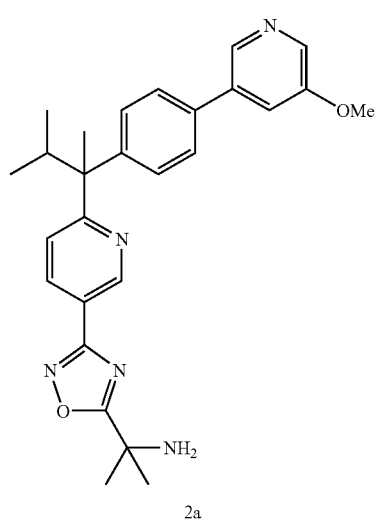

2a

Preparation of 2a

Step A: Preparation of 2-[3-(6-{1-[4-(5-methoxypyridin-3-yl)phenyl]-1,2-dimethylpropyl}pyridin-3-yl)-1,2,4-oxadiazol-5-yl]propan-2-amine (2a)

HCl (380 µL of a 4.0 M solution in 1,4-dioxane, 1.52 mmol)) in water (20.0 µL) was added to a stirred solution of 1Am (20.8 mg, 0.0370 mmol) in 1,4-dioxane (300 µL) at 10° C., and the resulting mixture was allowed to warm to rt. After approximately 1 h, the reaction mixture was poured into saturated aqueous sodium bicarbonate and extracted three times with EtOAc. The combined organic extracts were washed with water and brine, dried (sodium sulfate) and concentrated in vacuo. The crude residue was purified by preparative reversed phase HPLC on YMC Pack Pro C18 stationary phase (CH₃CN/H₂O as eluent, 0.05% TFA as modifier), followed by lyophilization of the purified fractions to afford the title compound 2a. m/z (ES) 458 (MH)+. ¹HNMR (500 MHz, CD₃OD): δ 9.22 (s, 1H), 8.75 (br, 1H), 8.55 (br, 1H), 8.47 (d, 1H, J=8.2 Hz), 8.42 (s, 1H), 7.78 (d, 2H, J=8.1 Hz), 7.73 (d, 1H, J=8.4 Hz), 7.64 (d, 2H, J=8.0 Hz), 4.11 (s, 3H), 3.22 (m, 1H), 1.88 (s, 6H), 1.82 (s, 3H), 0.92 (d, 3H, J=6.4 Hz), 0.87 (d, 3H, J=6.4 Hz).

Following procedures similar to those described in Example 2, the following additional compounds 2b-2d can be prepared:

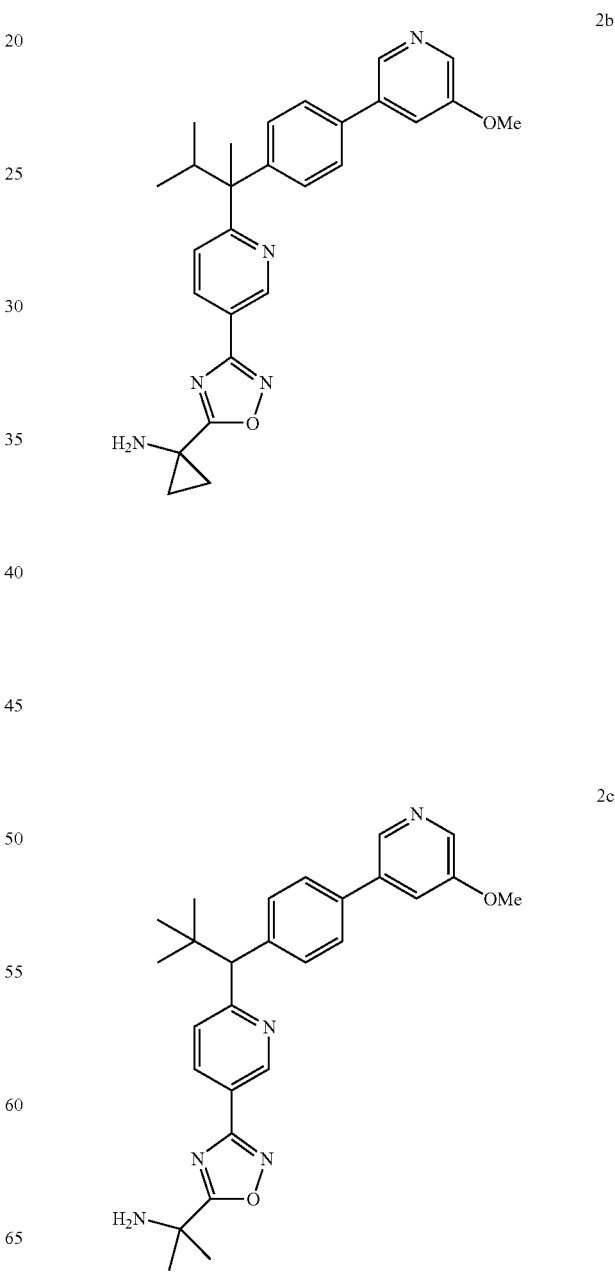

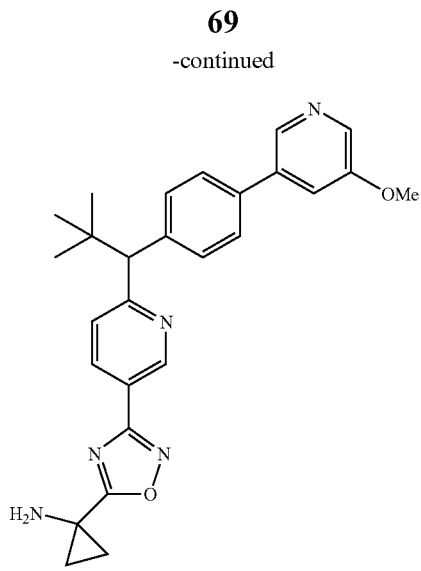

2d

Parent Ion m/z (MH)+ data for compounds

For 1-[3-(6-{1-[4-(5-methoxypyridin-3-Aphenyl]-1,2-dimethylpropyl}pyridin-3-yl)-1,2,4-oxadiazol-5-yl]cyclopropanamine (2b): m/z (ES) 456 (MH)+.

Example 3

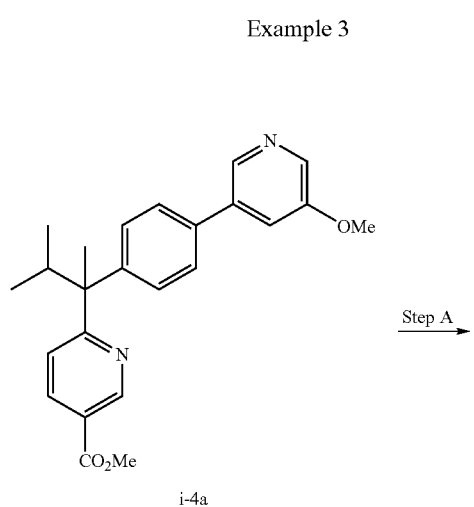

i-4a

Step A

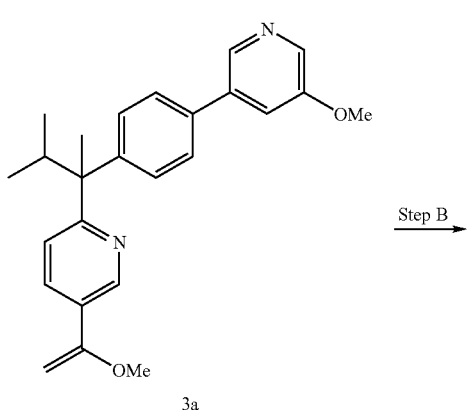

3a

Step B

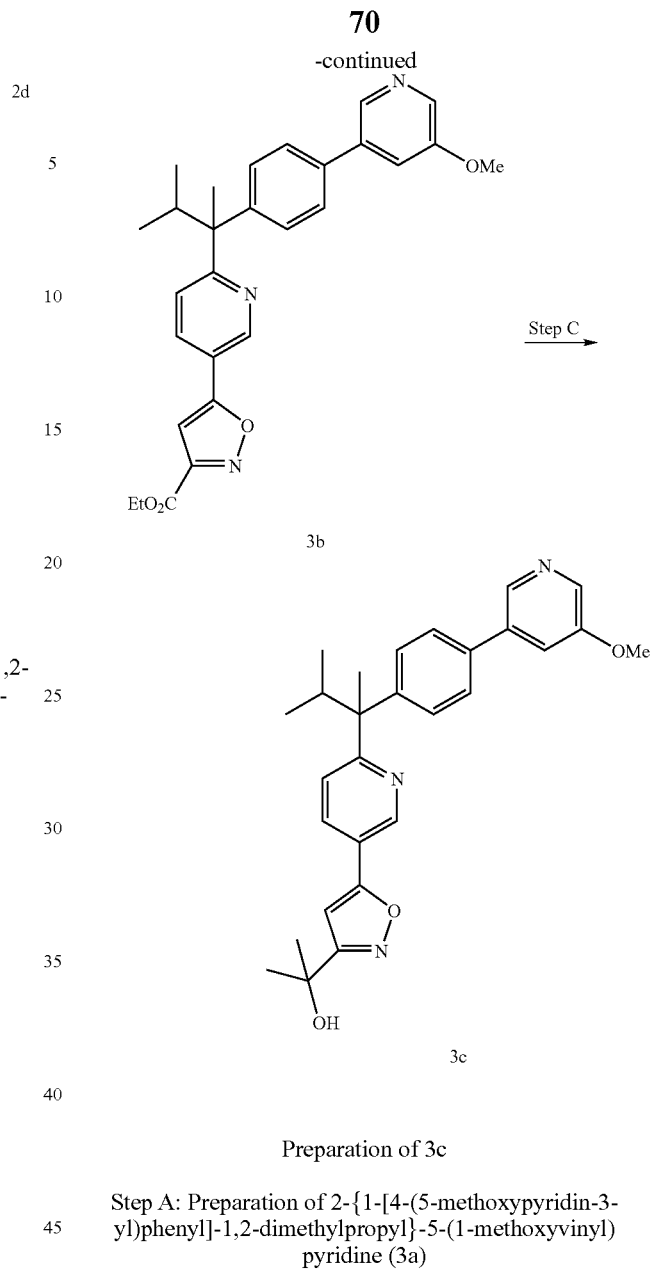

Preparation of 3c

Step A: Preparation of 2-{1-[4-(5-methoxypyridin-3-yl)phenyl]-1,2-dimethylpropyl}-5-(1-methoxyvinyl)pyridine (3a)

Tebbe reagent (0.510 mL of a 0.5 M solution in toluene, 0.256 mmol) was added to a stirred solution of i-4a (100 mg, 0.256 mmol) in THF (2.00 mL) at rt. After approximately 16 h, the reaction was quenched by addition of basic alumina, and the resulting suspension was filtered through a short column of basic alumina eluting with EtOAc. The filtrate was concentrated in vacuo, and the crude residue (3a) was used without purification in the subsequent reaction.

Step B: Preparation of ethyl 5-(6-{1-[4-(5-methoxypyridin-3-yl)phenyl]-1,2-dimethylpropyl}pyridin-3-yl)isoxazole-3-carboxylate (3b)

Ethyl 2-chloro-2-(hydroxyimino)acetate (116 mg, 0.768 mmol) was added to a stirred solution of 3a (0.256 mmol) and triethylamine (357 µL, 2.56 mmol) in THF (10.0 mL) at rt. After approximately 1 h, the reaction mixture was acidified to ~pH 1 by the addition of TFA, and the resulting mixture was heated to 50° C. for approximately 4.5 h. The reaction mixture was cooled to rt, neutralized with saturated aqueous sodium bicarbonate and concentrated in vacuo. The crude residue was purified by flash chromatography on silica gel (gradient elution; 0%-100% EtOAc/hexanes as eluent) to afford the title compound 3b. m/z (ES) 472 (MH)+. $^1$HNMR (500 MHz, CDCl$_3$): δ 9.05 (d, 1H, J=2.3 Hz), 8.46 (d, 1H, J=2.4 Hz), 8.29 (d, 1H, J=2.5 Hz), 8.00 (dd, 1H, J=2.3, 8.5 Hz), 7.51 (m, 4H), 7.41 (d, 1H, J=8.2 Hz), 7.36 (m, 1H), 6.98 (s, 1H), 4.50 (q, 2H, J=7.1 Hz), 3.92 (s, 3H), 3.71 (m, 1H), 1.78 (s, 1H), 1.47 (t, 3H, J=7.1 Hz), 0.91 (d, 3H, J=6.7 Hz), 0.88 (d, 3H, J=6.9 Hz).

Step C: Preparation of 2-[5-(6-{1-[4-(5-methoxypyridin-3-yl)phenyl]-1,2-dimethylpropyl}pyridin-3-yl)isoxazol-3-yl]propan-2-ol (3c)

Methyl magnesium bromide (300 μL of a 1.4M solution in toluene:THF (75:25), 0.420 mmol) was added to a stirred solution of 3b (40.0 mg, 0.0850 mmol) in THF (2.00 mL) at 0° C. After approximately 3 h, the reaction was quenched with saturated aqueous ammonium chloride and extracted three times with EtOAc. The combined organic extracts were washed with water and brine, dried (magnesium sulfate) and concentrated in vacuo. The crude residue was purified by preparative thin-layer chromatography on silica gel (60% EtOAc/hexanes as eluent) to afford the title compound 3c. m/z (ES) 458 (MH)+. $^1$HNMR (500 MHz, CDCl$_3$): δ 9.02 (m, 1H), 8.46 (m, 1H), 8.29 (m, 1H), 7.96 (m, 1H), 7.51 (m, 4H), 7.38 (m, 2H), 6.62 (s, 1H), 3.92 (s, 3H), 3.18 (m, 1H), 1.78 (s, 3H), 1.69 (s, 6H), 0.91 (d, 3H, J=6.6 Hz), 0.88 (d, 3H, J=6.9 Hz).

Following procedures similar to those described in Examples 1 and 3, the following additional compounds represented in Table 3 can be prepared:

TABLE 3

3A

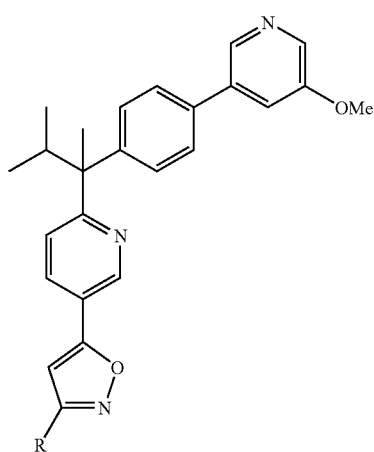

TABLE 3-continued

3B

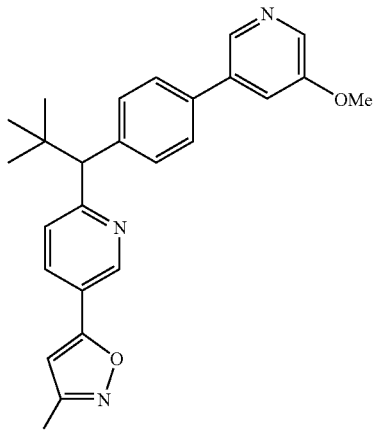

| Ex. #3A | Ex. #3B | R |
|---|---|---|
| — | a | —CH$_2$OH |
| — | b | (C(CH$_3$)$_2$OH) |
| c | c | (C(CH$_3$)(cyclopropyl)OH) |
| d | d | (CH$_2$-piperidinyl) |
| e | e | (CH$_2$-morpholinyl) |
| f | f | (CH$_2$-4-fluoropiperidinyl) |
| g | g | (CH$_2$-pyrrolidinyl) |
| h | h | (CH$_2$-(3S)-fluoropyrrolidinyl) |
| i | i | (CH$_2$-(3R)-fluoropyrrolidinyl) |
| j | j | (CH$_2$-3-hydroxyazetidinyl) |

TABLE 3-continued
| | | |
|---|---|---|
| k | k | 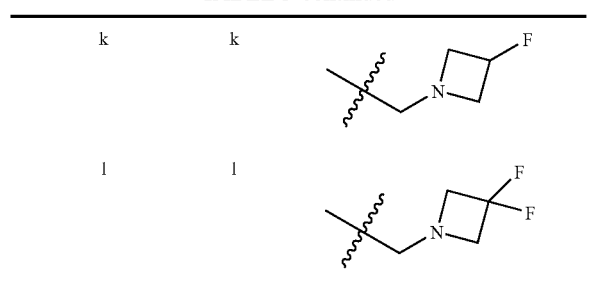 |
| l | l | |
Example 4
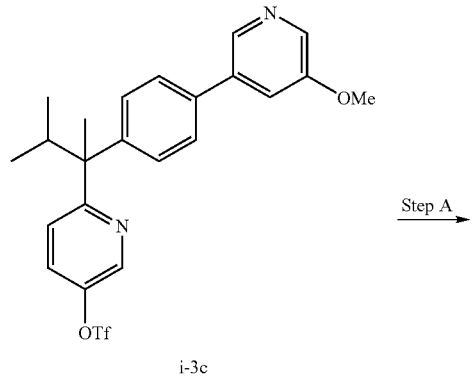
i-3c
Step A
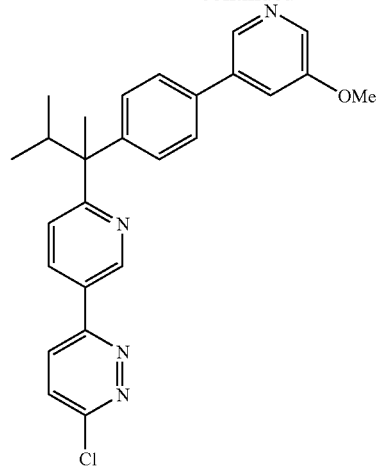
4b
Step C
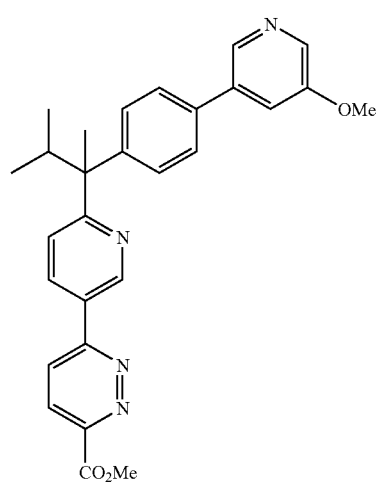
4c
Step D
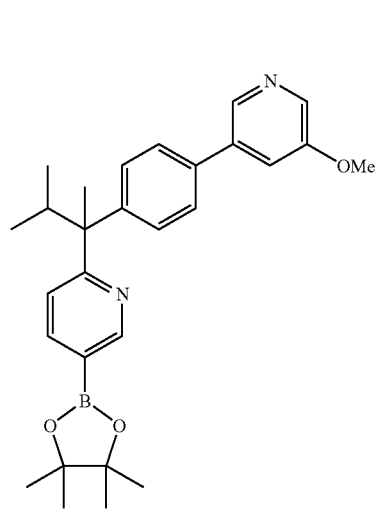
4a
Step B
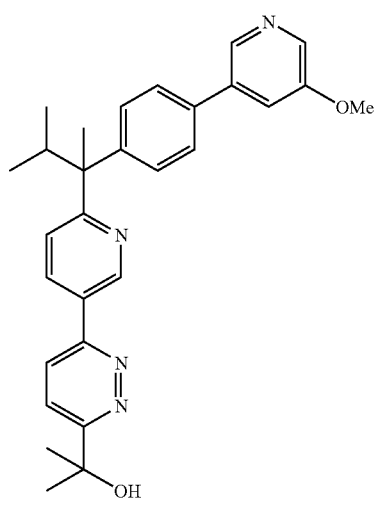
4d

Preparation of 4d

Step A: Preparation of 2-{1-[4-(5-methoxypyridin-3-yl)phenyl]-1,2-dimethylpropyl}-5-(4,4,5,5-tetramethyl-1,3,2-dioxaborolan-2-yl)pyridine (4a)

[1,1'-Bis(diphenylphosphino)ferrocene]dichloropalladium(II) (220 mg, 0.303 mmol) was added to a stirred suspension of i-3c (2.91 g, 6.06 mmol), bis(pinacolato)diboron (1.69 g, 6.66 mmol) and potassium acetate (1.71 g, 18.2 mmol) in DMSO (25.0 mL) at rt. The resulting suspension was heated to 80° C. for approximately 1.5 h. After cooling to rt, the reaction mixture was diluted with EtOAc and filtered through a short column of CELITE®, eluting with EtOAc. The filtrate was washed with water and brine, dried (sodium sulfate) and concentrated in vacuo to afford the title compound 4a. $^1$HNMR (500 MHz, CDCl$_3$): δ 8.96 (d, J=0.9 Hz), 8.45 (d, 1H, J=1.3 Hz), 8.28 (d, 1H, J=2.5 Hz), 7.95 (dd, 1H, J=1.9, 8.1 Hz), 7.48 (m, 4H), 7.37 (m, 1H), 7.26 (d, 1H, J=8.0 Hz), 3.93 (s, 3H), 3.18 (m, 1H), 1.75 (s, 3H), 1.27 (s, 12H), 0.88 (d, 3H, J=6.6 Hz), 0.84 (d, 3H, J=6.8 Hz).

Step B: Preparation of 3-chloro-6-(6-{1-[4-(5-methoxypyridin-3-yl)phenyl]-1,2-dimethylpropyl}pyridin-3-yl)pyridazine (4b)

[1,1'-Bis(diphenylphosphino)ferrocene]dichloropalladium(II) (700 mg, 0.960 mmol) was added to a stirred solution of 4a (2.20 g, 4.80 mmol), 3,6-dichloropyridazine (1.40 g, 5.80 mmol) and sodium carbonate (4.80 mL of a 2.0 M aqueous solution, 9.60 mmol) in EtOH:toluene (25.0 mL of an 80:20 mixture, respectively) at rt. The resulting solution was heated to 95° C. for approximately 2 h. After cooling to rt, the reaction mixture was filtered through a short column of CELITE®, eluting with EtOAc. The filtrate was washed with water and brine, dried (sodium sulfate) and concentrated in vacuo. The crude residue was purified by flash chromatography on silica gel (gradient elution; 0%-60% EtOAc/hexanes as eluent) to furnish the title compound 4b. m/z (ES) 445 (MH)$^+$. $^1$HNMR (500 MHz, CDCl$_3$): δ 9.19 (d, 1H, J=2.1 Hz), 8.46 (d, 1H, J=1.6 Hz), 8.36 (dd, 1H, J=2.5, 8.5 Hz), 8.29 (d, 1H, J=2.8 Hz), 7.86 (d, 1H, J=8.9 Hz), 7.62 (d, 1H, J=8.9 Hz), 7.52 (m, 4H), 7.46 (d, 1H, J=8.2 Hz), 7.37 (m, 1H), 3.93 (s, 3H), 3.21 (m, 1H), 1.80 (s, 3H), 0.93 (d, 3H, J=6.9 Hz), 0.89 (d, 3H, J=6.9 Hz).

Step C: Preparation of methyl 6-(6-{1-[4-(5-methoxypyridin-3-yl)phenyl]-1,2-dimethylpropyl}pyridin-3-yl)pyridazine-3-carboxylate (4c)

Palladium (II) acetate (81.0 mg, 0.360 mmol) and 1,1'-bis(diphenylphosphino)ferrocene (401 mg, 0.720 mmol) were added to a stirred solution of 4b (1.60 g, 3.62 mmol) in triethylamine:DMF:methanol (25.0 mL of a 1:10:10 mixture, respectively) at rt. The reaction mixture was saturated with carbon monoxide and then heated to 70° C. under a carbon monoxide atmosphere (balloon) for approximately 3.5 h. After cooling to rt, the reaction mixture was filtered through a short column of CELITE®, eluting with DCM. The filtrate was partially concentrated in vacuo and diluted with EtOAc. The organic phase was washed with water and brine, dried (sodium sulfate) and concentrated in vacuo. Purification of the crude residue by flash chromatography on silica gel (gradient elution; 40%-80% EtOAc/hexanes as eluent) afforded the title compound 4c. m/z (ES) 469 (MH)$^+$. $^1$HNMR. (500 MHz, CDCl$_3$): δ 9.31 (d, 1H, J=1.9 Hz), 8.45 (m, 2H), 8.29 (d, 2H, J=8.7 Hz), 8.03 (d, 1H, J=8.7 Hz), 7.50 (m, 6H), 4.12 (s, 3H), 3.94 (s, 3H), 3.22 (m, 1H), 1.81 (s, 3H), 0.93 (d, 3H, J=6.6 Hz), 0.89 (d, 3H, J=6.6 Hz).

Step D: Preparation of 2-[6-(6-{1-[4-(5-methoxypyridin-3-yl)phenyl]-1,2-dimethylpropyl}pyridin-3-yl)pyridazin-3-yl]propan-2-ol (4d)

Methyl magnesium bromide (1.10 mL of a 1.4 M toluene:THF (75:25) solution) was added to a stirred solution of 4c (360 mg, 0.768 mmol) in THF (5.00 mL) at 0° C. After approximately 45 min, the reaction was quenched by the addition of 1 N HCl, and the resulting mixture was poured into saturated aqueous sodium bicarbonate and extracted with EtOAc. The combined organic extracts were washed with brine, dried (sodium sulfate) and concentrated in vacuo. The crude residue was purified by flash chromatography on silica gel (gradient elution; 20%-100% EtOAc/hexanes as eluent) to afford the title compound 4d. m/z (ES) 469 (MH)$^+$. $^1$HNMR (500 MHz, CDCl$_3$): δ 9.21 (d, 1H, J=2.3 Hz), 8.46 (br, 1H), 8.40 (dd, 1H, J=2.3, 8.5 Hz), 8.28 (br, 1H), 7.90 (d, 1H, J=8.9 Hz), 7.78 (d, 1H, J=8.7 Hz), 7.52 (m, 4H), 7.45 (d, 1H, J=8.4 Hz), 7.40 (m, 1H), 3.93 (s, 3H), 3.20 (m, 1H), 1.80 (s, 3H), 1.70 (s, 6H), 0.92 (d, 3H, J=6.6 Hz), 0.88 (d, 3H, J=6.8 Hz).

Compound 4e was prepared from i-3d following procedures as described above for the preparation of 4d. m/z (ES) 533 (MH)$^+$.

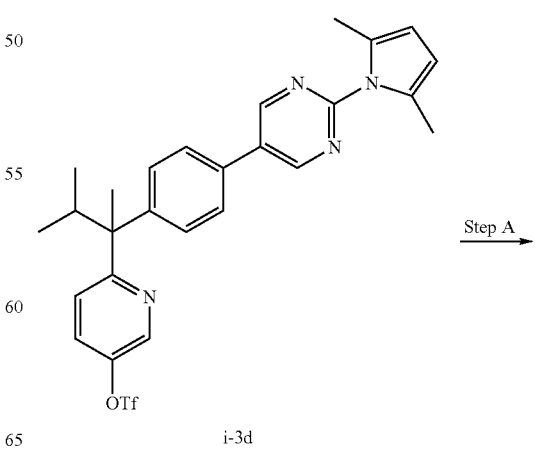

Step A i-3d

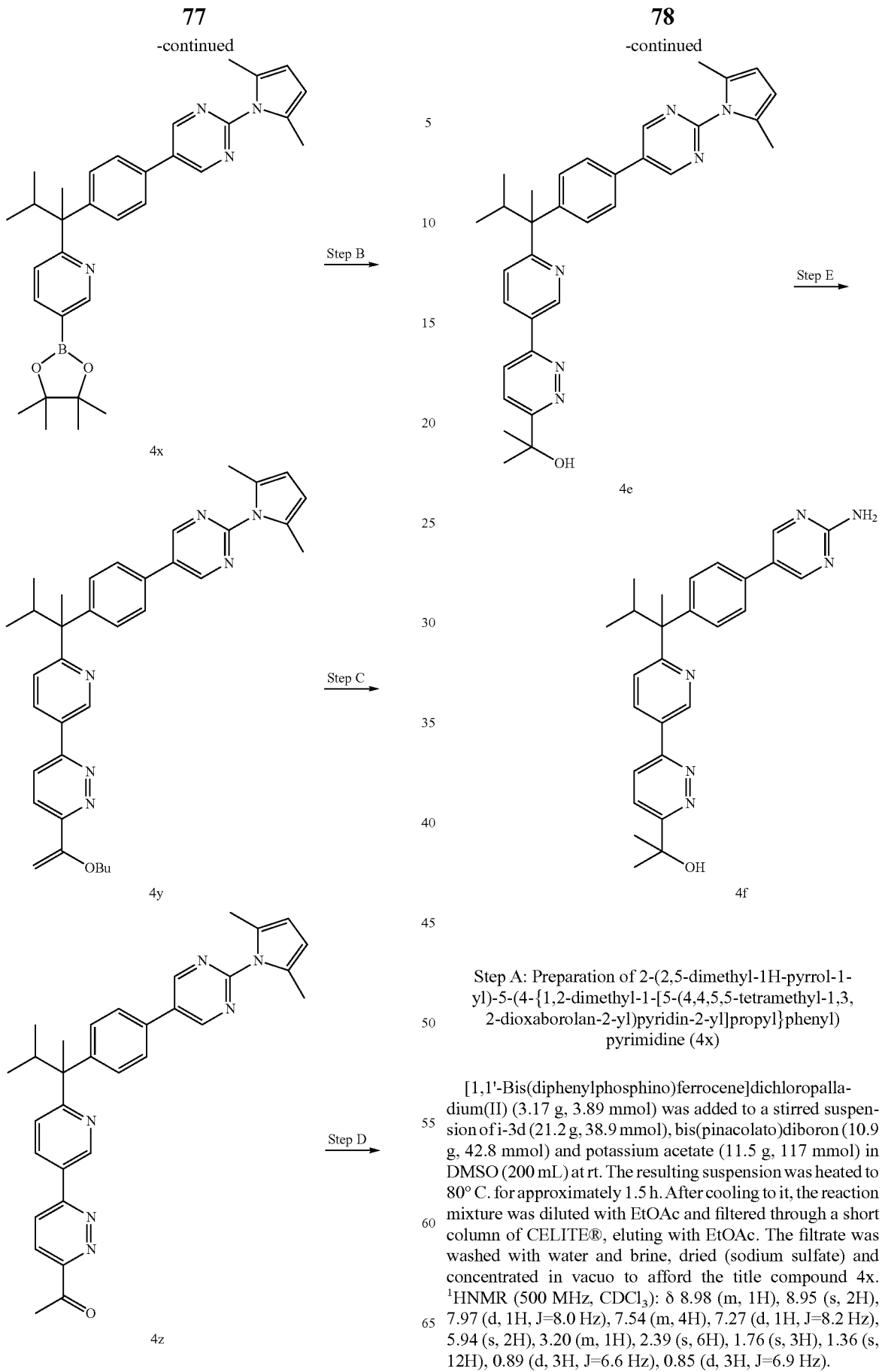

Step A: Preparation of 2-(2,5-dimethyl-1H-pyrrol-1-yl)-5-(4-{1,2-dimethyl-1-[5-(4,4,5,5-tetramethyl-1,3,2-dioxaborolan-2-yl)pyridin-2-yl]propyl}phenyl)pyrimidine (4x)

[1,1'-Bis(diphenylphosphino)ferrocene]dichloropalladium(II) (3.17 g, 3.89 mmol) was added to a stirred suspension of i-3d (21.2 g, 38.9 mmol), bis(pinacolato)diboron (10.9 g, 42.8 mmol) and potassium acetate (11.5 g, 117 mmol) in DMSO (200 mL) at rt. The resulting suspension was heated to 80° C. for approximately 1.5 h. After cooling to it, the reaction mixture was diluted with EtOAc and filtered through a short column of CELITE®, eluting with EtOAc. The filtrate was washed with water and brine, dried (sodium sulfate) and concentrated in vacuo to afford the title compound 4x. $^1$HNMR (500 MHz, CDCl$_3$): δ 8.98 (m, 1H), 8.95 (s, 2H), 7.97 (d, 1H, J=8.0 Hz), 7.54 (m, 4H), 7.27 (d, 1H, J=8.2 Hz), 5.94 (s, 2H), 3.20 (m, 1H), 2.39 (s, 6H), 1.76 (s, 3H), 1.36 (s, 12H), 0.89 (d, 3H, J=6.6 Hz), 0.85 (d, 3H, J=6.9 Hz).

Step B: Preparation of 3-(1-butoxyvinyl)-6-[6-(1-{4-[2-(2,5-dimethyl-1H-pyrrol-1-yl)pyrimidin-5-yl]phenyl}-1,2-dimethylpropyl)pyridin-3-yl]pyridazine (4y)

[1,1'-Bis(diphenylphosphino)ferrocene]dichloropalladim (II) (3.18 g, 3.89 mmol) was added to a stirred solution of 4x(20.3 g, 38.9 mmol), i-7a (9.93 g, 46.7 mmol) and sodium carbonate (38.9 mL of a 2.0 M aqueous solution, 77.8 mmol) in EtOH:toluene (175 mL of an 80:20 mixture, respectively) at it. The resulting solution was heated to 95° C. for approximately 3 h. After cooling to rt, the reaction mixture was filtered through a short column of CELITE®, eluting with EtOAc. The filtrate was washed with water and brine, dried (sodium sulfate) and concentrated in vacuo. The crude residue was purified by flash chromatography on silica gel (gradient elution; 0%-60% EtOAc/hexanes as eluent) to furnish the title compound m/z (ES) 573 (MH)$^+$. $^1$HNMR (500 MHz, CDCl$_3$): δ 9.26 (d, 1H, J=2.0 Hz), 8.96 (s, 2H), 8.46 (dd, 1H, J=2.2, 8.3 Hz), 7.90 (m, 2H), 7.58 (m, 4H), 7.46 (d, 1H, J=8.5 Hz), 5.93 (s, 2H), 5.85 (d, 1H, J=2.1 Hz), 4.57 (d, 1H, J=1.9 Hz), 3.99 (t, 2H, J=6.3 Hz), 3.24 (m, 1H), 2.39 (s, 6H), 1.83 (m, 2H), 1.82 (s, 3H), 1.56 (m, 2H), 1.03 (t, 3H, J=7.5 Hz), 0.96 (d, 3H, J=6.7 Hz), 0.89 (d, 3H, J=6.7 Hz).

Step C: Preparation of 1-{6-[6-(1-{4-[2-(2,5-dimethyl-1H-pyrrol-1-yl)pyrimidin-5-yl]phenyl}-1,2-dimethylpropyl)pyridin-3-yl]pyridazin-3-yl}ethanone (4z)

Hydrochloric acid (100 mL of a 1.0 M solution in EtOH) was added to a stirred solution of 4y (7.03 g, 12.3 mmol) in EtOH (50.0 mL) at 0° C. After approximately 15 min, a second portion of hydrochloric acid (100 mL of a 2.0 M aqueous solution) was added, and after another 15 min, a third portion of hydrochloric acid (100 mL of a 1.0 M solution in EtOH). After an additional 15 min, a final portion of hydrochloric acid (50 mL of a 6.0 M aqueous solution) was added, and the resulting reaction was aged for 30 min. The reaction was carefully neutralized by the addition of solid sodium bicarbonate. The resulting mixture was saturated with solid sodium chloride and extracted twice with EtOAc. The combined organic extracts were washed with brine, dried (sodium sulfate) and concentrated in vacuo to afford the title compound 4z m/z (ES) 517 (MH)$^+$. $^1$HNMR (500 MHz, CDCl$_3$): δ 9.32 (d, 1H, J=2.3 Hz), 8.95 (s, 2H), 8.47 (dd, 1H, J=2.3, 8.5 Hz), 8.22 (d, 1H, J=8.9 Hz), 8.04 (d, 1H, J=8.9 Hz), 7.58 (m, 4H), 7.50 (d, 1H, J=8.4 Hz), 5.91 (s, 2H), 3.24 (m, 1H), 2.94 (s, 3H), 2.37 (s, 6H), 1.82 (s, 3H), 0.94 (d, 3H, J=6.6 Hz), 0.89 (d, 3H, J=6.6 Hz).

Step D: Preparation of 2-{6-[6-(1-{4-[2-(2,5-dimethyl-1H-pyrrol-1-yl)pyrimidin-5-yl]phenyl}-1,2-dimethylpropyl)pyridin-3-yl]pyridazin-3-yl}propan-2-ol (4e)

Methyl magnesium bromide (32.4 mL of a 1.4 M solution in THF:toluene (25:75)) was added to a stirred solution of lithium chloride (1.93 g, 45.4 mmol) and 4z (11.7 g, 22.7 mmol) in THF (70 mL) at 0° C. After approximately 1 h at 0° C., the reaction was quenched by the dropwise addition of 1.0 M hydrochloric acid, and the resulting mixture stirred for 15 min. The resulting mixture was poured slowly into saturated aqueous sodium bicarbonate and extracted with EtOAc. The combined organic extracts were washed with brine, dried (magnesium sulfate) and concentrated in vacuo. The crude residue was purified by flash chromatography on silica gel (gradient elution; 35%-75% EtOAc/hexanes as eluent) to furnish the title compound 4e. m/z (ES) 533 (MH)$^+$. $^1$HNMR (500 MHz, CDCl$_3$): δ 9.23 (d, 1H, J=2.1 Hz), 8.95 (s, 2H), 8.39 (dd, 1H, J=2.3, 8.5 Hz), 7.89 (d, 1H, J=9.0 Hz), 7.79 (d, 1H, J=8.9 Hz), 7.57 (m, 4H), 7.46 (d, 1H, J=8.5 Hz), 5.92 (s, 2H), 4.20 (s, 1H), 3.22 (m, 1H), 2.38 (s, 6H), 1.81 (s, 3H), 1.70 (s, 6H), 0.93 (d, 3H, J=6.4 Hz), 0.88 (d, 3H, J=6.6 Hz).

Step E: Preparation of 2-[6-(6-{1-[4-(2-aminopyrimidin-5-yl)phenyl]-1,2-dimethylpropyl}pyridin-3-yl)pyridazin-3-yl]propan-2-ol (4f)

Hydroxylamine hydrochloride (94.0 mg, 1.350 mmol) was added to a stirred solution of 4e (72.0 mg, 0.135 mmol) and triethylamine (10.0 μL, 0.0730 mmol) in EtOH/water (900 μL of a 2:1 mixture, respectively) at rt, and the resulting mixture was heated at 80° C. for approximately 14 h. After cooling to rt, the reaction mixture was poured into saturated aqueous sodium bicarbonate and extracted three times with EtOAc. The combined organic extracts were washed with water and brine, dried (sodium sulfate) and concentrated in vacuo. The crude residue was purified by preparative reversed phase HPLC on YMC Pack Pro C18 stationary phase (CH$_3$CN/H$_2$O as eluent, 0.05% TFA as modifier), followed by lyophilization of the purified fractions to afford the title compound 4f. m/z (ES) 455 (MH)$^+$.

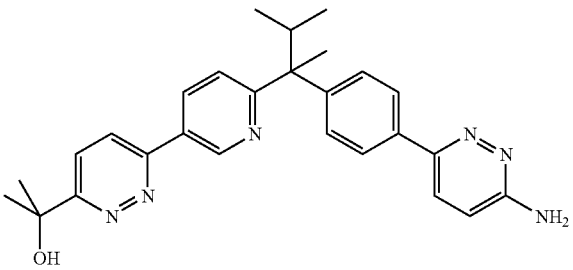

4g

Preparation of 2-[6-(6-{1-[4-(6-aminopyridazin-3-yl)phenyl]-1,2-dimethylpropyl}pyridin-3-yl)pyridazin-3-yl]propan-2-ol (4g)

Compound 4g was prepared from i-3e following procedures as described above for the preparation of compounds 4d and 4f. m/z (ES) 455 (MH)$^+$.

Following procedures similar to those described in Example 4 and the preceding schemes, the following additional compounds represented in Table 4 can be prepared:

TABLE 4
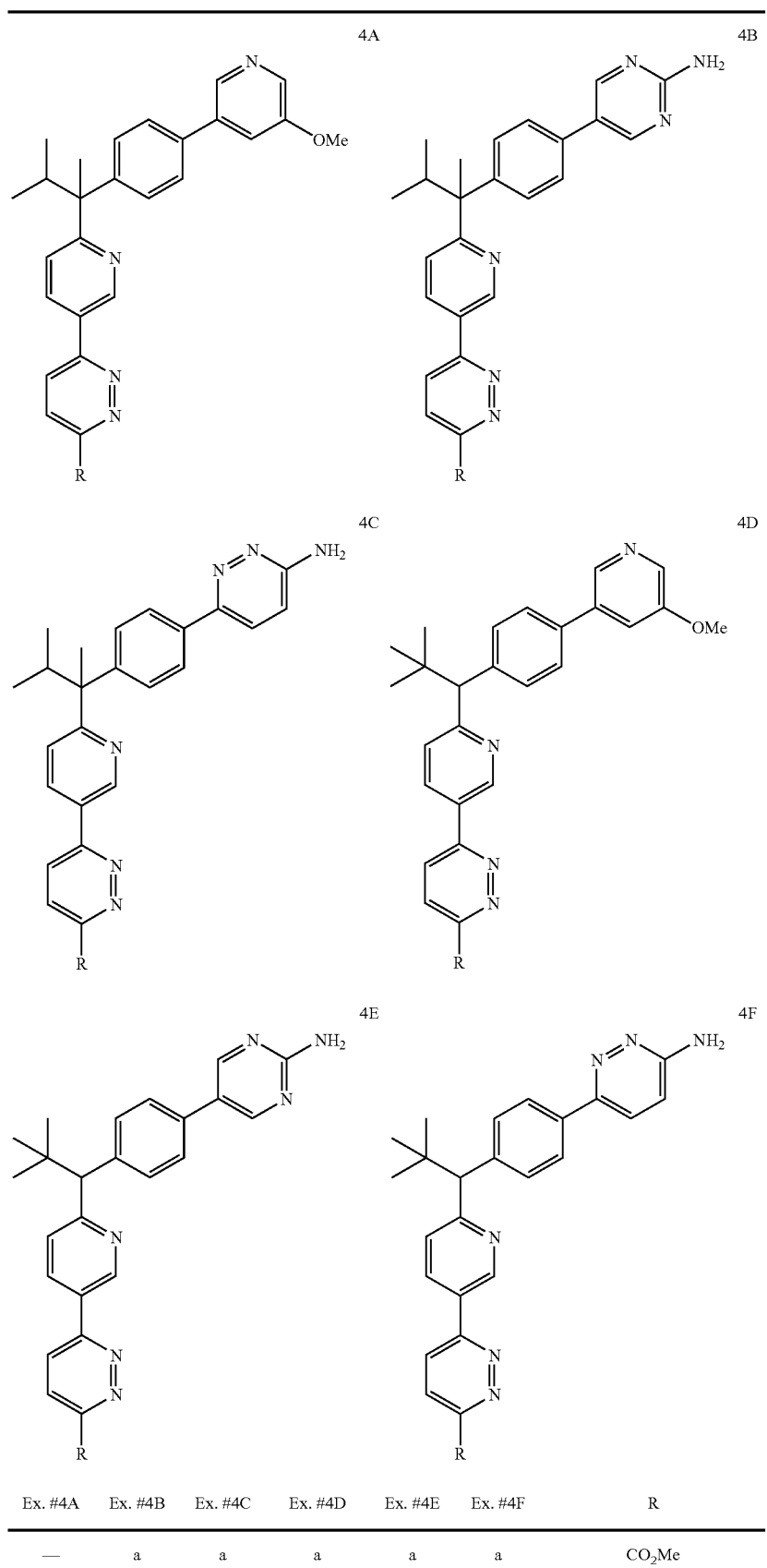
| Ex. #4A | Ex. #4B | Ex. #4C | Ex. #4D | Ex. #4E | Ex. #4F | R |
|---|---|---|---|---|---|---|
| — | a | a | a | a | a | CO$_2$Me |

TABLE 4-continued
| | | | | | | |
|---|---|---|---|---|---|---|
| — | b | b | b | b | b | 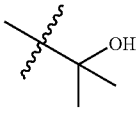 [SMILES: *C(C)(C)O] |
| c | c | c | c | c | c | Me |
| d | d | d | d | d | d | CF$_3$ |
| e | e | e | e | e | e | —CH$_2$OH |
| f | f | f | f | f | f | 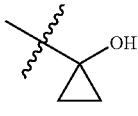 [SMILES: *C1(O)CC1] |
| g | g | g | g | g | g | 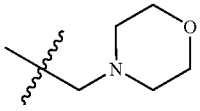 |
| h | h | h | h | h | h | 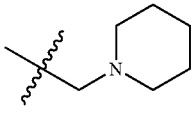 [SMILES: *CN1CCCCC1] |
| i | i | i | i | i | i | 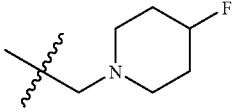 [SMILES: *CN1CCC(F)CC1] |
| j | j | j | j | j | j | 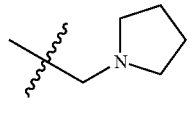 [SMILES: *CN1CCCC1] |
| k | k | k | k | k | k | 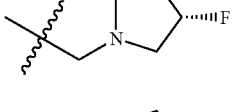 |
| l | l | l | l | l | l | 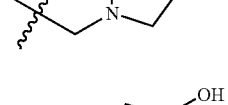 |
| m | m | m | m | m | m |  |
| n | n | n | n | n | n | 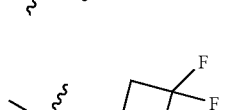 |
| o | o | o | o | o | o |  |
Table 4. Parent Ion m/z (MH)$^+$ data for compounds
For 3-(6-{1-[4-(5-methoxypyridin-3-yl)phenyl]-1,2-dimethylpropyl}pyridin-3-yl)-6-methylpyridazine (4Ac): m/z (ES) 425 (MH)$^+$.

For 3-(6-{1-[4-(5-methoxypyridin-3-yl)phenyl]-1,2-dimethylpropyl}pyridin-3-yl)-6-(trifluoromethyl)pyridazine (4Ad): m/z (ES) 479 (MH)⁺.

Example 5

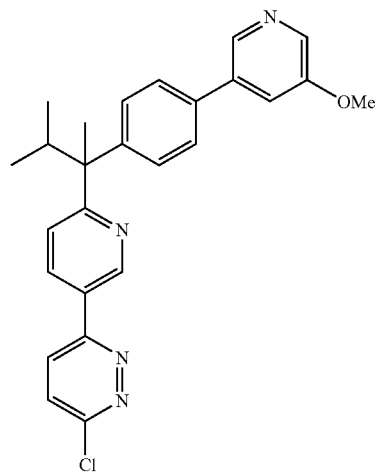

4b

Step A

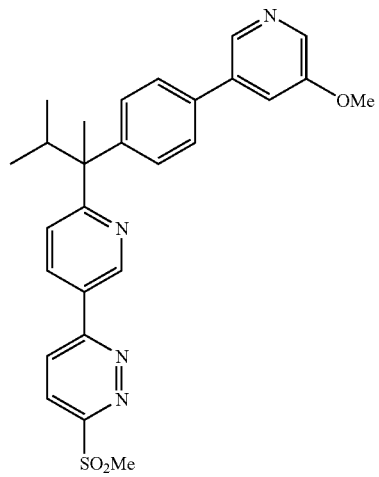

5a

Preparation of 5a

Step A: Preparation of 3-(6-{1-[4-(5-methoxypyridin-3-yl)phenyl]-1,2-dimethylpropyl}pyridin-3-yl)-6-(methylsulfonyl)pyridazine Sodium methansulfinate (69.0 mg, 0.680 mmol) was added to a stirred solution of 4b (150 mg, 0.340 mmol) in DMF (2.00 mL) at rt. The resulting mixture was heated to 120° C. for approximately 20 h. After cooling to rt, the reaction mixture was poured into saturated aqueous sodium bicarbonate and extracted three times with EtOAc. The combined organic extracts were washed with water and brine, dried (sodium sulfate) and concentrated in vacuo. Purification of the crude residue by flash chromatography on silica gel (gradient elution; 20%-60% EtOAc/hexanes as eluent) afforded the title compound 5a. m/z (ES) 489 (MH)⁺. ¹HNMR (500 MHz, CD₃OD): δ 9.36 (m, 1H), 8.74 (m, 1H), 8.68 (m, 1H), 8.55 (m, 2H), 8.41 (m, 1H), 8.38 (d; 1H, J=8.9 Hz), 7.83 (m, 1H), 7.79 (d, 2H, J=8.4 Hz), 7.66 (d, 2H, J=8.7 Hz), 4.10 (s, 3H), 3.30 (s, 3H), 3.25 (m, 1H), 1.86 (s, 3H), 0.96 (d, 3H, J=6.7 Hz); 0.90 (d, 3H, J=6.6 Hz).

Following procedures similar to those described in Example 5, the following additional compounds can be prepared:

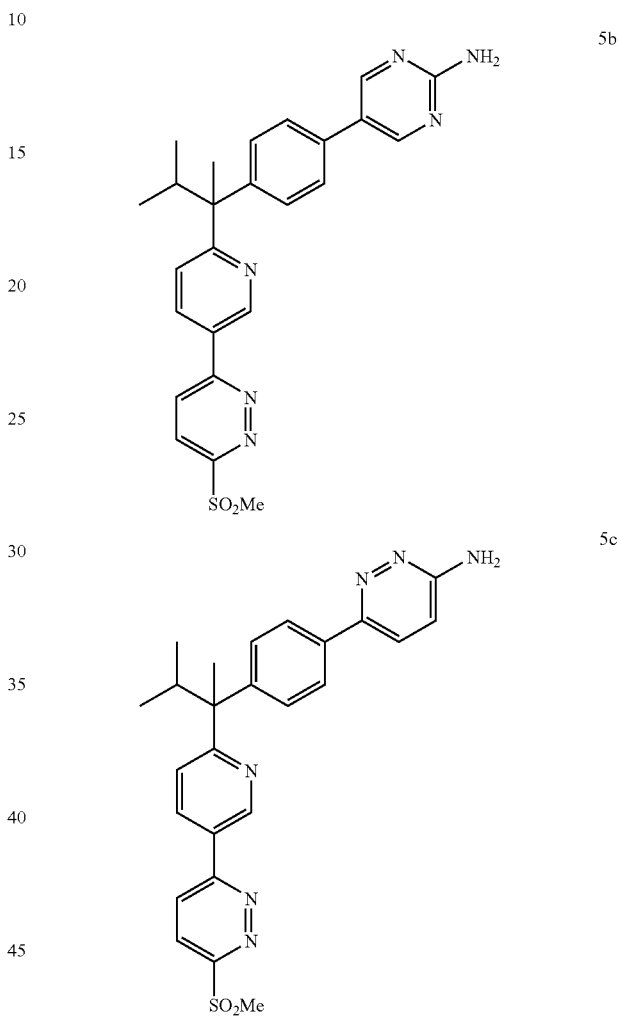

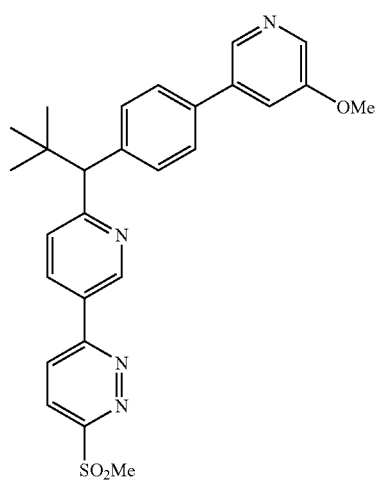

5e
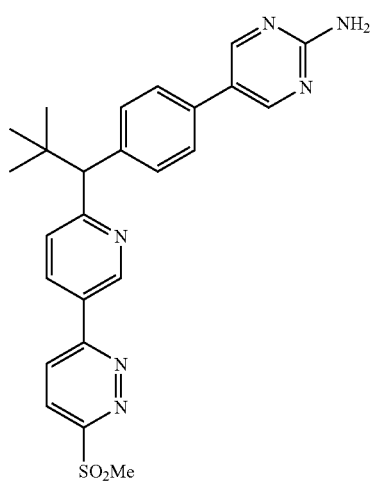
5f
Example 6
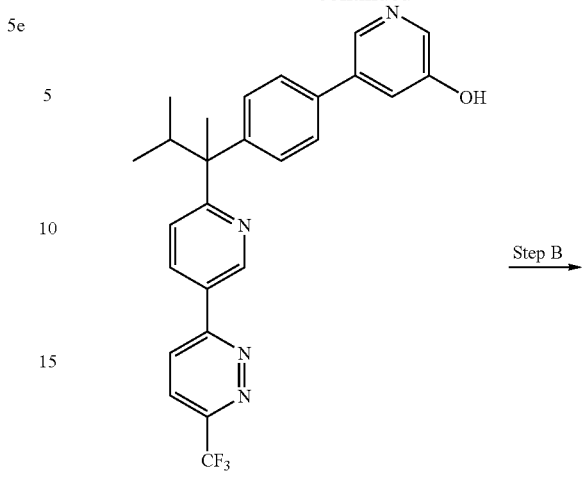
Step A
-continued
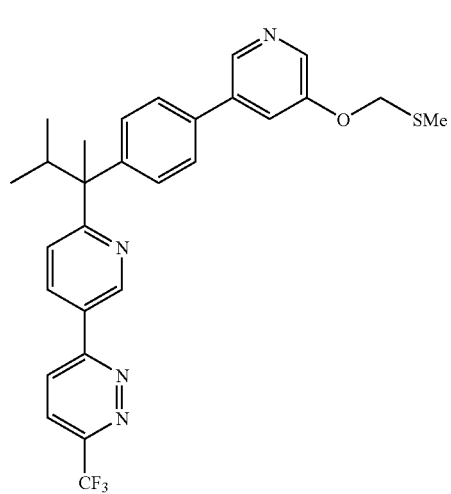

Preparation of 6c

Step A: Preparation of 5-[4-(1,2-dimethyl-1-{5-[6-(trifluoromethyl)pyridazin-3-yl]pyridin-2-yl}propyl) phenyl]pyridin-3-ol (6a)

Pyridinium chloride (160 mg, 1.30 mmol) was added to neat 4Ad (60.0 mg, 0.130 mmol) at rt, and the resulting mixture was heated in a sealed tube at 180° C. for approximately 2 h. After cooling to rt, the reaction mixture was quenched with saturated aqueous sodium bicarbonate and extracted three times with EtOAc. The combined organic extracts were washed with water and brine, dried (sodium sulfate) and concentrated in vacuo. Purification of the crude residue by flash chromatography on silica gel (gradient elution; 30%-75% EtOAc/hexanes as eluent) afforded the title compound 6a. m/z (ES) 465 (MH)$^+$.

Step B: Preparation of 3-{6-[1,2-dimethyl-1-(4-{5-[(methylthio)methoxy]pyridin-3-yl}phenyl)propyl] pyridin-3-yl}-6-(trifluoromethyl)pyridazine (6b)

Chloromethyl methyl sulfide (12.0 μL, 0.140 mmol) was added to a stirred suspension of 6a (42.0 mg, 0.0910 mmol) and cesium carbonate (46.0 mg, 0.140 mmol) in DMF (2.00 mL) at rt, and the resulting mixture was heated at 40° C. for approximately 2 h. The reaction mixture was cooled to rt, and second portions of cesium carbonate (46.0 mg, 0.140 mmol) and chloromethyl methyl sulfide (12.0 μL, 0.140 mmol) were added. The resulting mixture was heated at 40° C. for about another 3 h. After cooling to rt, the reaction mixture was poured into 10% aqueous sodium hydrosulfate and extracted three times with diethyl ether. The combined organic extracts were washed with water and brine, dried (sodium sulfate) and concentrated in vacuo. Purification of the crude residue by flash chromatography on silica gel (gradient elution; 20%-50% EtOAc/hexanes as eluent) afforded the title compound 6b. m/z (ES) 525 (MH)$^+$ $^1$HNMR (500 MHz, CDCl$_3$): δ 9.28 (d, 1H, J=2.1 Hz), 8.51 (br, 1H), 8.45 (dd, 1H, J=2.4, 8.3 Hz), 8.32 (br, 1H), 8.07 (d, 1H, J=8.9 Hz), 7.92 (d, 1H, J=9.0 Hz), 7.55 (m, 6H), 5.25 (s, 2H), 3.21 (m, 1H), 2.28 (s, 3H), 1.81 (s, 3H), 0.93 (d, 3H, J=6.4 Hz), 0.89 (d, 3H, J=6.6 Hz).

Step C: Preparation of 3-[6-(1-{4-[5-(fluoromethoxy)pyridin-3-yl]phenyl}-1,2-dimethylpropyl)pyridin-3-yl]-6-(trifluoromethyl)pyridazine (6c)

A solution of 6b (18.0 mg, 0.0340 mmol) in 1,2-dichloroethane (2.00 mL) was added to a stirred solution of xenon difluoride (58.0 mg, 0.340 mmol) in 1,2-dichloroethane (1.00 mL) at 0° C. After approximately 2 h, the reaction mixture was quenched with triethylamine (0.250 mL) and concentrated in vacuo. Purification of the crude residue by flash chromatography on silica gel (gradient elution; 10%-30% EtOAc/hexanes as eluent) afforded the title compound 6c. m/z (ES) 497 (MH)$^+$ Following procedures similar to those described in Example 6, the following additional compounds represented in Table 6 can be prepared:

TABLE 6

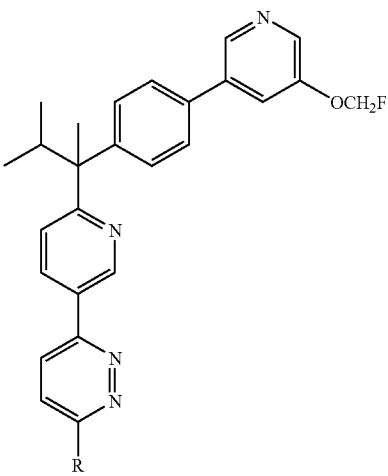

6A

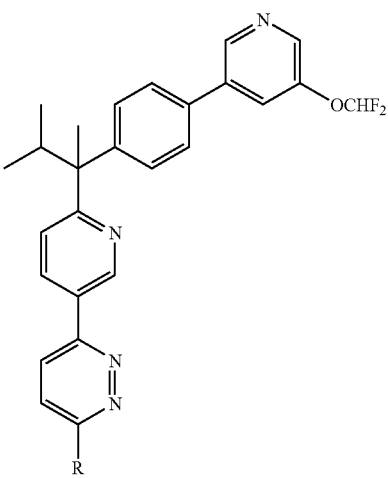

6B

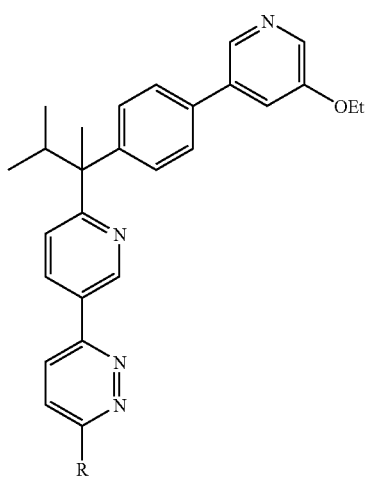

6C

TABLE 6-continued

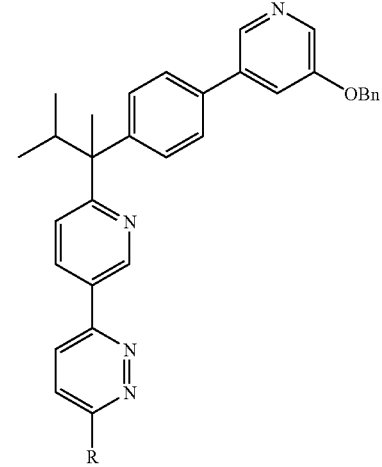

6D

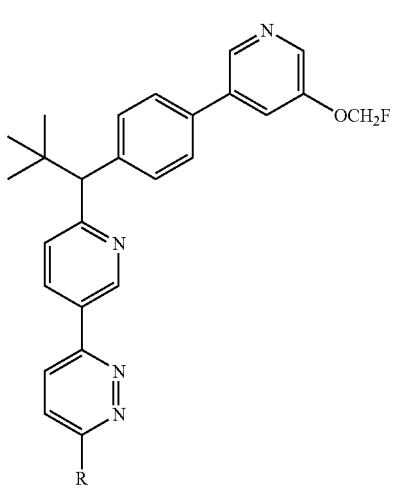

6E

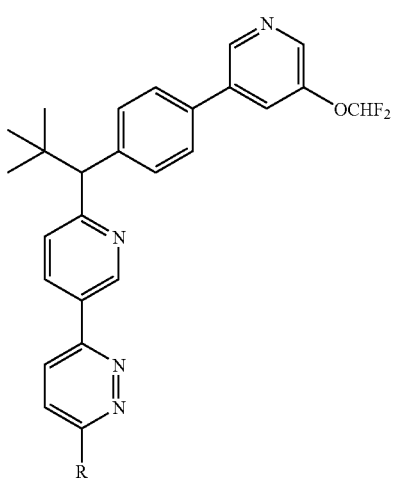

6F

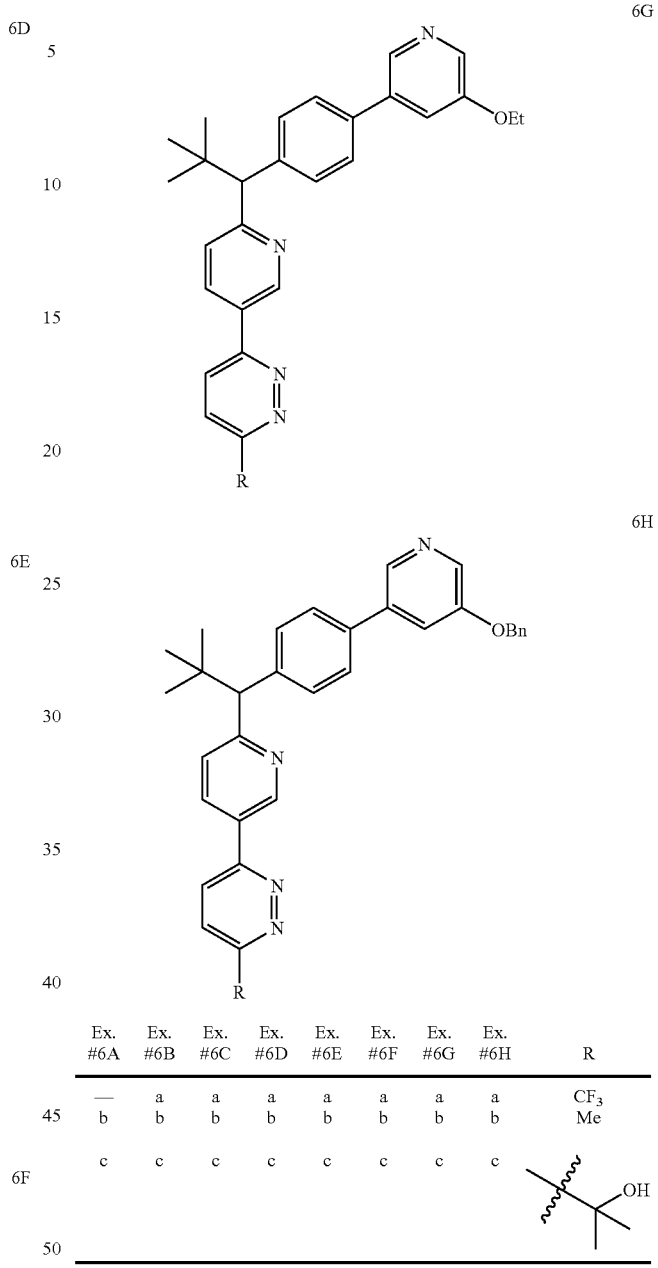

6G

6H

| Ex. #6A | Ex. #6B | Ex. #6C | Ex. #6D | Ex. #6E | Ex. #6F | Ex. #6G | Ex. #6H | R |
|---|---|---|---|---|---|---|---|---|
| — | a | a | a | a | a | a | a | CF₃ |
| b | b | b | b | b | b | b | b | Me |
| c | c | c | c | c | c | c | c | ⁓⧸⧹OH (dimethyl hydroxy) |

Table 6. Parent Ion m/z (MH)⁺ data for compounds

For 3-[6-(1-{4-[5-(difluoromethoxy)pyridin-3-yl]phenyl}-1,2-dimethylpropyl)pyridin-3-yl]-6-(trifluoromethyl)pyridazine (6Ba): m/z (ES) 515 (MH)⁺.

For 3-(6-{1-[4-(5-ethoxypyridin-3-yl)phenyl]-1,2-dimethylpropyl}pyridin-3-yl)-6-(trifluoromethyl)pyridazine (6Ca): m/z (ES) 493 (MH)⁺.

For 3-[6-(1-{4-[5-(benzyloxy)pyridin-3-yl]phenyl}-1,2-dimethylpropyl)pyridin-3-yl]-6-(trifluoromethyl)pyridazine (6Da): m/z (ES) 555 (MH)⁺.

Example 7

Following procedures similar to those described in the preceding examples, the following additional compounds represented in Table 7 can be prepared:

TABLE 7
7A 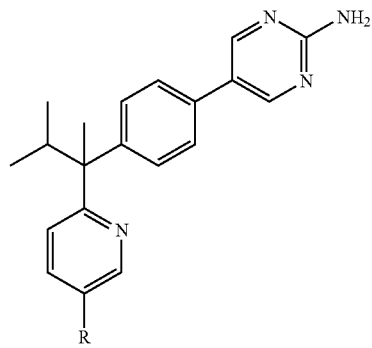
7B 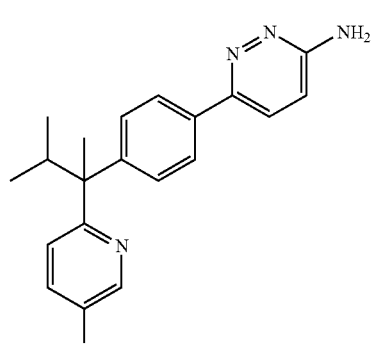
7C 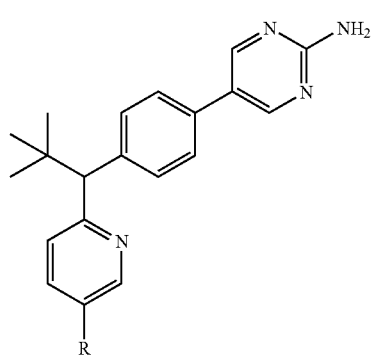
7D 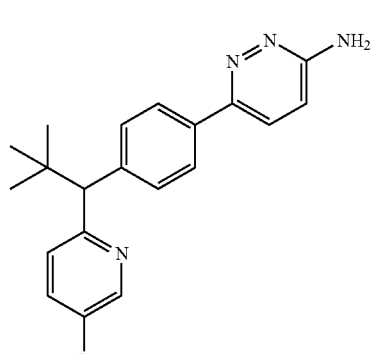
TABLE 7-continued
| Ex. #7A | Ex. #7B | Ex. #7C | Ex. #7D | R |
|---|---|---|---|---|
| a | a | a | a | 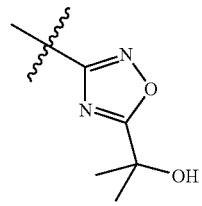 [SMILES: *c1noc(C(C)(C)O)n1] |
| b | b | b | b | 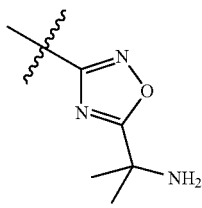 [SMILES: *c1noc(C(C)(C)N)n1] |
| c | c | c | c | 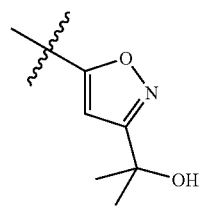 [SMILES: *c1cc(C(C)(C)O)no1] |
| d | d | d | d | 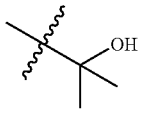 [SMILES: *C(C)(C)O] |
| e | e | e | e | —CO₂Me |
| f | f | f | f | —CN |
Table 7. Parent Ion m/z (MH)⁺ data for compounds
For 2-(6-{1-[4-(2-aminopyrimidin-5-yl)phenyl]-1,2-dimethylpropyl}pyridin-3-yl)propan-2-ol (7Ad): m/z (ES) 377 (MH)⁺.
For methyl 6-{1-[4-(2-aminopyrimidin-5-yl)phenyl]-1,2-dimethylpropyl}nicotinate (7Ae): m/z (ES) 377 (MH)⁺.
For 6-{1-[4-(2-aminopyrimidin-5-yl)phenyl]-1,2-dimethylpropyl}nicotinonitrile (7Af): m/z (ES) 344 (MH)⁺.

For 2-(6-(1-[4-(6-aminopyridazin-3-yl)phenyl]-1,2-dimethylpropyl)pyridin-3-yl)propan-2-ol (7Bd): m/z (ES) 377 (MH)+

Example 8

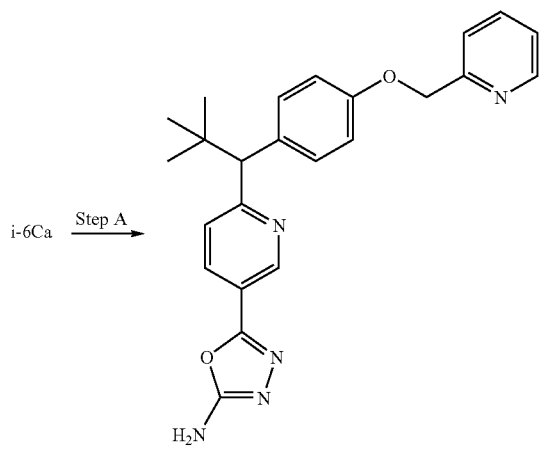

8a

Step A: Preparation of 5-(6-{2,2-dimethyl-1-[4-(pyridin-2-ylmethoxy)phenyl]pronyl}pyridin-3-yl)-1,3,4-oxadiazol-2-amine (8a)

Hydrazine monohydrate (1.50 mL, 31.0 mmol) was added to a stirred solution of i-6Ca (41.0 mg, 0.104 mmol) in ethanol (5 mL), and the resulting solution was heated at reflux for approximately 1.5 h. After cooling to rt, the volatiles were removed in vacuo, and the residue was partitioned between EtOAc, and water. The organic phase was separated, washed with water and brine, dried (sodium sulfate) and concentrated in vacuo. The crude residue was dissolved in dioxane (400 µL) to which aqueous sodium bicarbonate (17.0 mg, 0.208 mmol in 100 µL of water) was added dropwise via syringe. A solution of cyanogen bromide (17.0 mg, 0.156 mmol) in dioxane (100 µL) was then added slowly. After approximately 1 h, the reaction mixture was poured into saturated aqueous sodium bicarbonate and extracted twice with EtOAc. The combined organic extracts were washed with brine, dried (sodium sulfate) and concentrated in vacuo. Purification of the crude residue by preparative reversed phase HPLC on YMC Pack Pro C18 stationary phase (CH₃CN/H₂O as eluent, 0.05% TFA as modifier), followed by lyophilization of the purified fractions afforded the title compound 8a. m/z (ES) 416 (MH)+. ¹HNMR (500 MHz, CD₃OD): δ 9.08 (d, 1H, J=1.1 Hz), 8.76 (br s, 1H), 8.44 (m, 1H), 8.12 (dd, 1H, J=2.3, 8.2 Hz), 8.02 (d, 1H, J=8.0 Hz), 7.87 (m, 1H), 7.62 (d, 2H, J=8.7 Hz), 7.52 (d, 1H, J=8.2 Hz), 7.02 (d, 2H, J=8.7 Hz), 5.41 (s, 2H), 3.97 (s, 1H), 1.03 (s, 9H).

Following procedures similar to those described previously, the following additional compounds represented in Table 8 can be prepared:

TABLE 8

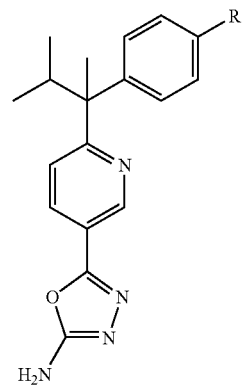

8A

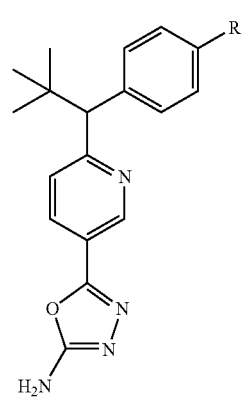

8B

| Ex. #8A | Ex. #8B | R |
|---|---|---|
| a | — | 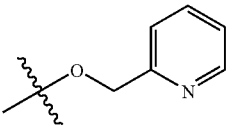 [SMILES: *OCc1ccccn1] |
| b | b | 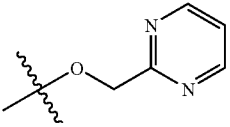 [SMILES: *OCc1ncccn1] |
| c | c | 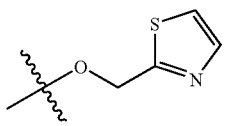 [SMILES: *OCc1nccs1] |
| d | d | 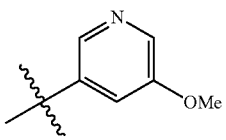 [SMILES: *c1cncc(OC)c1] |
| e | e | 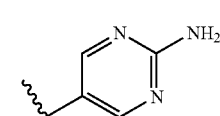 |

Example 9

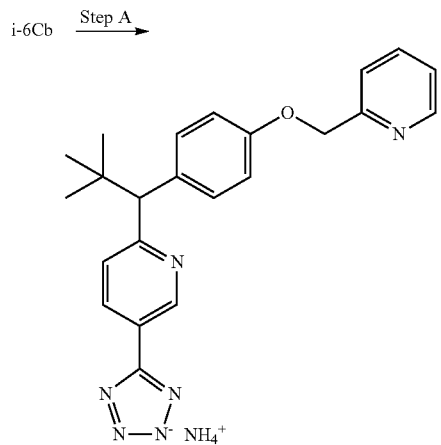

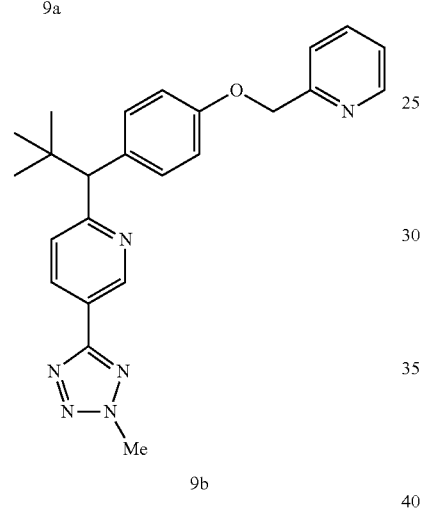

Step A: Preparation of ammonium 5-(6-{2,2-dimethyl-1-[4-(pyridin-2-ylmethoxy)phenyl]propyl}pyridin-3-yl)tetrazol-2-ide (9a)

Azidotrimethyltin (330 mg, 1.60 mmol) was added to a stirred solution of i-6Cb (145 mg, 0.406 mmol) in toluene (5.00 mL), and the resulting solution was heated to reflux for approximately 18 h. After cooling to rt, the reaction mixture was partially concentrated and diluted with ethanol. Hydrochloric acid (1 N in ethanol) was added, and after 1.5 h of vigorous agitation, the volatiles were removed in vacuo and the crude residue purified by flash chromatography on silica gel (gradient elution; 0%-100% DCM:methanol:axnmonium hydroxide (85:15:1)/DCM as eluent) to afford the title compound 9a. m/z (ES) 401 (MH)$^+$.

Step B: Preparation of 2-{2,2-dimethyl-1-[4-(pyridin-2-ylmethoxy)phenyl]propyl}-5-(2-methyl-2H-tetrazol-5-yl)pyridine (9b)

Iodomethane (30.0 μL, 0.482 mmol) was added to a stirred suspension of cesium carbonate (195 mg, 0.598 mmol) and 9a (50.0 mg, 0.119 mmol) in DMF (2.00 mL) at rt. After approximately 2 h, the reaction mixture was poured into saturated aqueous sodium bicarbonate and extracted three times with ethyl acetate. The combined organic extracts were washed three times with water and once with brine, dried (sodium sulfate) and concentrated in vacuo. Purification of the crude residue by flash chromatography on silica gel (gradient elution; 10%-60% EtOAc/hexanes as eluent) afforded the title compound 9b. m/z (ES) 415 (MH)$^+$.

Following procedures similar to those described previously, the following additional compounds represented in Table 9 can be prepared:

TABLE 9

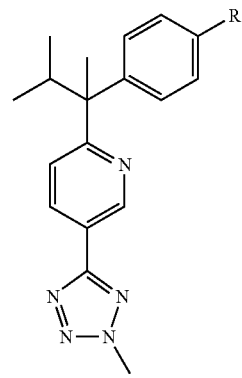

9A

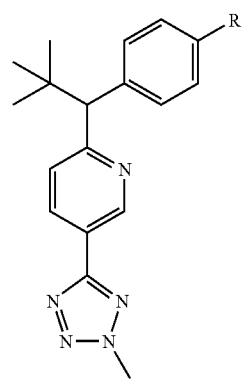

9B

| Ex. #9A | Ex. #9B | Z$^2$ |
|---------|---------|-------|
| a | — | 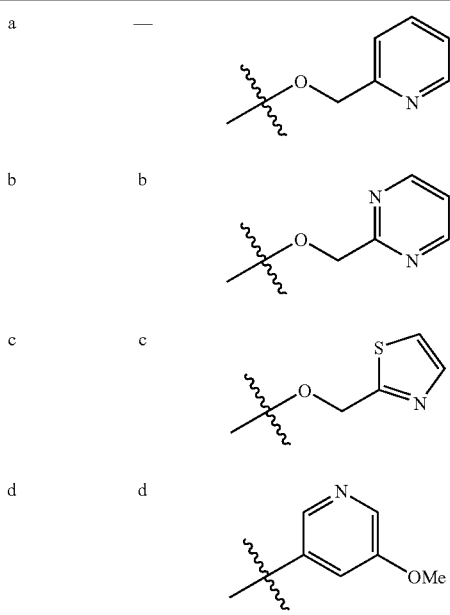 |
| b | b | |
| c | c | |
| d | d | |

TABLE 9-continued
| e | e | 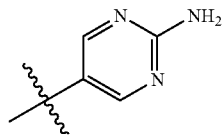 [SMILES: *c1cnc(N)nc1] |
Example 10
Following procedures similar to those described in previous examples, the following additional compounds represented in Table 10 can be prepared:
TABLE 10
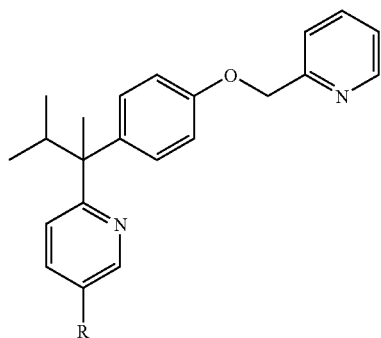
10A
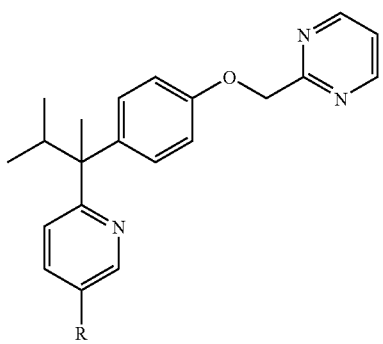
10B
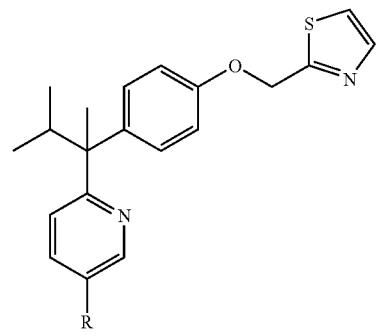
10C
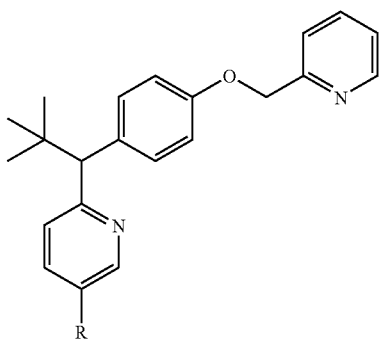
10D
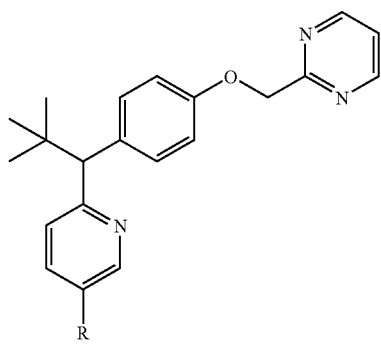
10E
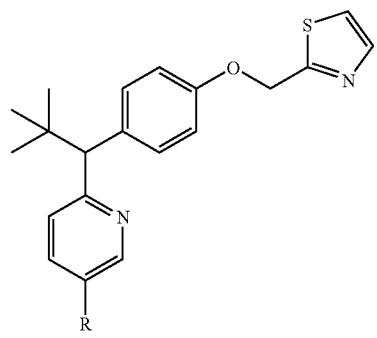
10F
| Ex. 10A | Ex. 10B | Ex. 10C | Ex. 10D | Ex. 10E | Ex. 10F | R |
|---|---|---|---|---|---|---|
| a | a | a | a | a | a | 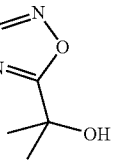 |

TABLE 10-continued
| | | | | | | |
|---|---|---|---|---|---|---|
| b | b | b | b | b | b | 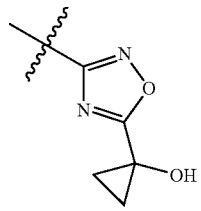 [SMILES: *c1noc(C2(O)CC2)n1] |
| c | c | c | c | c | c | 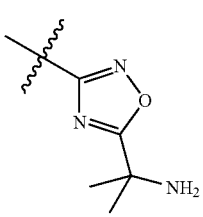 [SMILES: *c1noc(C(C)(C)N)n1] |
| d | d | d | d | d | d | 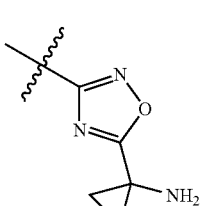 |
| e | e | e | e | e | e | 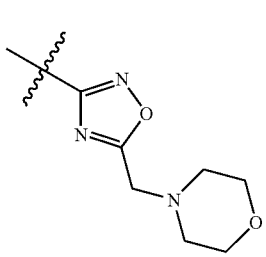 [SMILES: *c1noc(CN2CCOCC2)n1] |
| f | f | f | f | f | f | 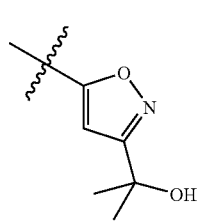 [SMILES: *c1cc(C(C)(C)O)no1] |
| g | g | g | g | g | g | 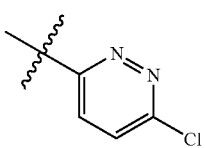 [SMILES: *c1ccc(Cl)nn1] |
| h | h | h | h | h | h | 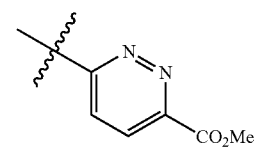 [SMILES: *c1ccc(C(=O)OC)nn1] |
| i | i | i | i | i | i | 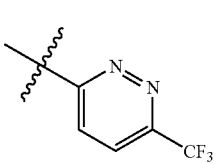 [SMILES: *c1ccc(C(F)(F)F)nn1] |

TABLE 10-continued

| | | | | | | |
|---|---|---|---|---|---|---|
| j | j | j | j | j | j | 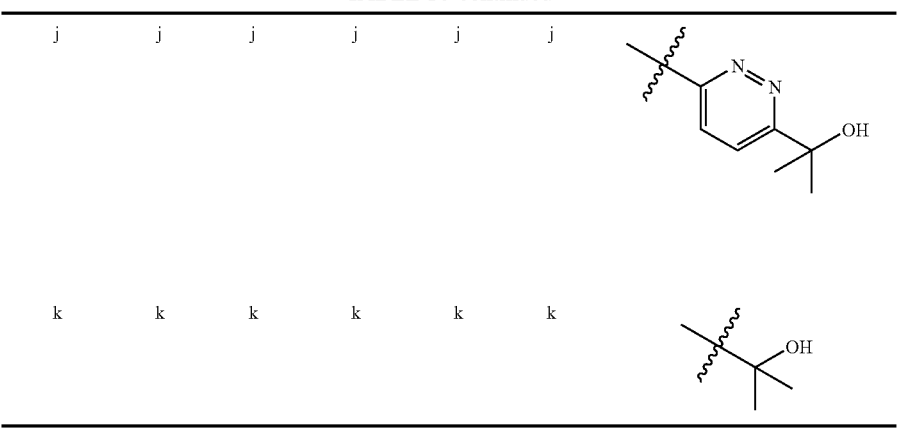 |
| k | k | k | k | k | k | |

Table 10. Parent Ion m/z (MH)+ data for compounds

For 2-[3-(6-{1,2-dimethyl-1-[4-(pyridin-2-ylmethoxy)phenyl]propyl}pyridin-3-yl)-1,2,4-oxadiazol-5-yl]propan-2-ol (10Aa): m/z (ES) 459 (MH)+.

For 1-[3-(6-{1,2-dimethyl-1-[4-(pyridin-2-ylmethoxy)phenyl]propyl}pyridin-3-yl)-1,2,4-oxadiazol-5-yl]cyclopropanamine (10Ad): m/z (ES) 456 (MH)+.

For 4-{[3-(6-{1,2-dimethyl-1-[4-(pyridin-2-ylmethoxy)phenyl]propyl}pyridin-3-yl)-1,2,4-oxadiazol-5-yl]methyl}morpholine (10Ae): m/z (ES) 500 (MH)+.

For 3-chloro-6-(6-{1,2-dimethyl-1-[4-(pyridin-2-ylmethoxy)phenyl]propyl}pyridin-3-yppyridazine (10Ag): m/z (ES) 445 (MH)+.

For methyl 6-(6-{1,2-dimethyl-1-[4-(pyridin-2-ylmethoxy)phenyl]propyl}pyridin-3-yl)pyridazine-3-carboxylate (10Ah): m/z (ES) 469 (MH)+.

For 2-[6-(6-{1,2-dimethyl-1-[4-(pyridin-2-ylmethoxy)phenyl]propyl}pyridin-3-yl)pyridazin-3-yl]propan-2-ol (10Aj): m/z (ES) 469 (MH)+.

For 2-[3-(6-{1,2-dimethyl-1-[4-(1,3-thiazol-2-ylmethoxy)phenyl]propyl}pyridin-3-yl)-1,2,4-oxadiazol-5-yl]propan-2-ol (10Ca): m/z (ES) 465 (MH)+.

For 1-[3-(6-{1,2-dimethyl-1-[4-(1,3-thiazol-2-ylmethoxy)phenyl]propyl}pyridin-3-yl)-1,2,4-oxadiazol-5-yl]cyclopropanamine (10Cd): m/z (ES) 462 (MH)+.

FLAP Binding Assay

Compound A

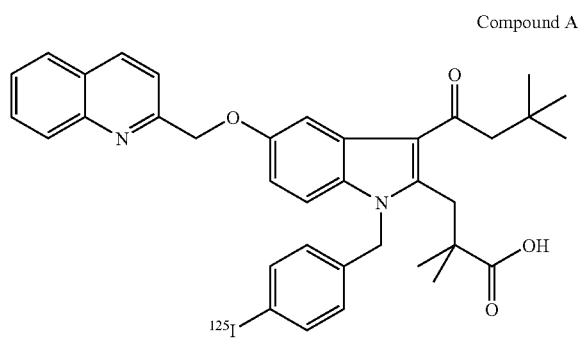

Compound B

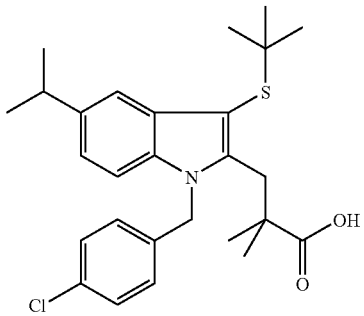

A 100,000×g pellet from human leukocyte 10,000×g supernatants (1) is the source of FLAP. The 100,000×g pellet membranes were resuspended in Tris-Tween assay buffer (100 mM Tris HCl pH 7.4, 140 mM NaCl, 2 mM EDTA, 0.5 mM dithiothreitol, 5% glycerol, 0.05% Tween 20) to yield a final protein concentration of 50 µg to 150 µg/ml. Aliquots (100 µl) of membrane suspension were added to 12 mm×75 mm polypropylene tubes containing 100 µl Tris-Tween assay buffer, 30,000 cpm of Compound A in 5 µl MeOH:assay buffer (1:1), and 2 µl dimethyl sulfoxide or competitor (i.e., the compound to be tested) in dimethyl sulfoxide. Compound B (10 µM final concentration) was used to determine non-specific binding. After a 20 minute incubation at room temperature, tube contents were diluted to 4 ml with cold 0.1 M Tris HCl pH 7.4, 0.05% Tween 20 wash buffer and the membranes were collected by filtration of GFB filters presoaked in the wash buffer. Tubes and filters were rinsed with 2×4 ml aliquots of cold wash buffer. Filters were transferred to 12 mm×3.5 mm polystyrene tubes for determination of radioactivity by gamma-scintillation counting.

Specific binding is defined as total binding minus non-specific binding. Total binding was Compound A bound to membranes in the absence of competitor; non-specific binding was Compound A bound in the presence of 10 uM Compound B. Preparation of Compound A is described in reference 1, below. The IC$_{50}$ values were obtained by computer analysis (see reference 2, below) of the experimental data. Representative tested compounds of the invention were determined to have an IC$_{50}$<50 nM, and examples are provided below:

| Example | IC50 |
|---|---|
| 1Ac | 2.1 nM |
| 2b | 3.6 nM |
| 4d | 1.1 nM |
| 4f | 0.5 nM |
| 4g | 0.6 nM |
| 4Ad | 1.4 nM |
| 5a | 0.7 nM |
| 6c | 2.8 nM |
| 6Da | 2.4 nM |
| 7Ad | 1.2 nM |
| 7Bd | 2.3 nM |
| 8a | 5.8 nM |
| 9b | 14 nM |
| 10Ah | 0.7 nM |
| 10Aj | 0.7 nM |
| 10Ca | 2.9 nM |

REFERENCES

1. Charleson, S., Prasti, P., Leger, S., Gillard, J. W, Vickers, P. J., Mancini, J. A., Charleson, P., Guay, J., Ford-Hutchinson, A. W., and Evans, J. F. (1992) Characterization of a 5-lipoxygenase-activating protein binding assay: correlation of affinity for 5-lipoxygenase-activating protein with leukotriene synthesis inhibition. Mol Pharmacol 41:873-879.
2. Kinetic, EBDA, Ligand, Lowry: A collection of Radioligand Binding Analysis Programs by G. A. McPherson. Elsevier-BIOSOFT.

While the invention has been described with reference to certain particular embodiments thereof, numerous alternative embodiments will be apparent to those skilled in the art from the teachings described herein. Recitation of a specific compound in the claims (i.e., a species) without a chiral designation is intended to encompass the racemate, enantiomeric mixtures, each individual enantiomer, a diastereoisomeric mixture and each individual diastereoisomer of the compound where such forms are possible due to the presence of one or more asymmetric centers. All patents, patent applications and publications cited herein are incorporated by reference in their entirety.

What is claimed is:
1. A compound represented by structural Formula Ia:

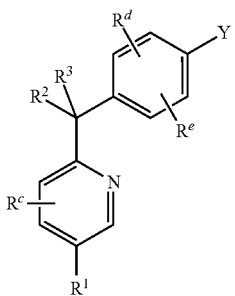

Ia or a pharmaceutically acceptable salt thereof wherein:
$R^1$ is selected from the group consisting of:
(a) a 5-membered aromatic or partially unsaturated heterocyclic ring containing 2 to 4 heteroatoms selected from N, S and O, wherein the heterocyclic ring is optionally substituted with $R^6$;
(b) a 6-membered aromatic or partially unsaturated heterocyclic ring containing 1 to 2 heteroatoms selected from N and O, wherein the heterocyclic ring is optionally substituted with $R^6$;
(c) an 8-membered aromatic or partially unsaturated ortho-fused bicyclic ring system containing 3-5 heteroatoms selected from one sulfur and 2-4 of nitrogen wherein one carbon in the ring is optionally substituted with a group selected from =O, =S, —SMe, —NH$_2$, —CF$_3$, —Cl, —C$_{1-4}$alkyl and C$_{1-4}$alkyl substituted with a group selected from —NH$_2$, —OH, —OC$_{1-4}$alkyl, —CN and 1-3 of fluoro;
(d) a 9-membered aromatic or partially unsaturated ortho-fused bicyclic ring system containing 3-4 nitrogen atoms, wherein one carbon in the ring is optionally substituted with a group selected from =O, =S, —SMe, —NH$_2$, —CF$_3$, —Cl, —C$_{1-4}$alkyl and C$_{1-4}$alkyl substituted with a group selected from —NH$_2$, —OH, —OC$_{1-4}$alkyl, —CN and 1-3 of fluoro;
(e) —C$_{1-6}$alkyl, —C$_{2-6}$alkenyl, and —C$_{2-6}$alkynyl, said alkyl, alkenyl and alkynyl groups being optionally substituted with $R^{12}$ and optionally substituted with $R^{13}$;
(f) —C$_{3-6}$ cycloalkyl optionally substituted with 1-3 substituents selected from the group consisting of fluoro, —NH$_2$, —OH and —C$_{1-3}$alkyl optionally substituted with 1-3 of fluoro;
(g) —O—R$^{6a}$ wherein R$^{6a}$ is selected from the group consisting of (1) —C$_{1-6}$alkyl optionally substituted with $R^{12}$ and optionally substituted with $R^{13}$, (2) —C$_{3-6}$ cycloakyl optionally substituted with $R^{12}$ and optionally substituted with $R^{13}$ and (3) —C$_{2-6}$alkyl-R$^{10}$;
with the proviso that R$^{6a}$ is not —C$_{1-6}$alkyl substituted with $Z^1$; and
(h) —OH, —CN, —CO$_2$R$^{4a}$, —C(O)NR$^7$R$^8$, NR$^7$R$^8$, —NR$^b$SO$_p$R$^a$, NR$^b$C(O)R$^a$, —NR$^b$C(O)NR$^a$R$^b$, —S(O)$_p$R$^a$, and —S(O)$_p$NR$^a$R$^b$;
p is an integer selected from 0, 1 and 2;
$R^2$ is selected from the group consisting of (a) —C$_{1-6}$alkyl optionally substituted with one or more substituents selected from the group consisting of —OH and fluoro, (b) —C$_{3-6}$ cycloalkyl optionally substituted with 1-3 of fluoro, and

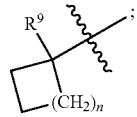

(c)

n is an integer selected from 0, 1, 2 and 3;
$R^3$ is selected from the group consisting of —H, —F, —OH, and —C$_{1-3}$alkyl optionally substituted with 1-5 fluoro;
$R^{4a}$ is selected from the group consisting of —H, —C$_{1-6}$alkyl and —C$_{3-6}$cycloalkyl;
$R^6$ is selected from the group consisting of (a)—C$_{1-6}$alkyl optionally substituted with one or more substituents selected from the group consisting of —OH, -NH$_2$, -CN, -O -C$_{1-4}$alkyl and fluoro, (b) -C$_{1-6}$alkyl-R$^{10}$, (c)—OC$_{1-6}$alkyl optionally substituted with one or more substituents selected from the group consisting of —OH, -NH$_2$ and fluoro, (d) -C$_{3-6}$ cycloalkyl optionally substituted with one or more substituents selected from the group consisting of methyl, —OH, -NH$_2$, -CF$_3$ and fluoro, (e) –NR$^7$R$^8$, (f) –SO$_2$C$_{1-3}$akyl, (g) –CO$_2$–R$^8$, (h) –OH, (i) =O (oxo), (j) –SH, (k) —S, (1) –SMe, (m) –C1, (n) –CF$_3$, (o) –CN and (p) R$^{10}$;

R$^7$ is selected from the group consisting of (a) —H, (b) —C$_{1-6}$ alkyl optionally substituted with one or more substitutents selected from the group consisting of —F, —NH$_2$ and —OH, (c) —C$_{3-6}$ cycloaklyl optionally substituted with one or more substitutents selected from the group consisting of methyl, —CF$_3$, —F, —NH$_2$ and —OH, (d) —COC$_{1-6}$alkyl optionally substituted with one or more substitutents selected from the group consisting of —F and —OH, (e) —COC$_{3-6}$cycloalkyl optionally substituted with one or more substituents selected from the group consisting of methyl, —CF$_3$, —F, —NH$_2$ and —OH, and (f) a 4-6 membered saturated heterocyclic ring containing one N, wherein the ring is bonded to the nitrogen in —NR$^7$R$^8$ through a carbon atom in the ring, and wherein the ring is optionally substituted with one or more substitutents selected from the group consisting of methyl, —CF$_3$, —F, —NH$_2$ and —OH;

R$^8$ is selected from the group consisting of (a) —H, (b) —C$_{1-6}$alkyl optionally substituted with one or more substituents selected from the group consisting of —F, —NH$_2$ and —OH, and (c) —C$_{3-6}$cycloalkyl optionally substituted with one or more substituents selected from the group consisting of methyl, —CF$_3$, —F, —NH$_2$ and —OH;

R$^9$ is selected from the group consisting of —H, —C$_{1-3}$alkyl and —F;

R$^{10}$ is a heterocyclic ring selected from the group consisting of (a) azetidinyl optionally substituted with one or more of methyl, —F and —OH, (b) pyrrolidinyl optionally substituted with one or more of methyl, —F and —OH, (c) piperidinyl optionally substituted with one or more of methyl, —F and —OH and (d) morpholinyl optionally substituted with one or more of methyl, —F and —OH;

Y is selected from the group consisting of (a) a 5-membered aromatic or partially unsaturated heterocyclic ring containing 1 to 4 heteroatoms selected from 1 to 4 of N and zero to 1 of S, wherein the heterocyclic ring is optionally substituted with R$^{11}$, (b) a 6-membered aromatic or partially unsaturated heterocyclic ring containing 1 to 2 N heteroatoms, wherein the heterocyclic ring is optionally substituted with R$^{11}$, (c) a 9-membered bicyclic aromatic or partially unsaturated heterocyclic ring containing 1 to 4 N heteroatoms, wherein the heterocyclic ring is optionally substituted with R$^{11}$, (c) a 10-membered bicyclic aromatic or partially unsaturated heterocyclic ring containing 1 to 4 N heteroatoms, wherein the heterocyclic ring is optionally substituted with R$^{11}$;

R$^{11}$ is selected from the group consisting of —F, —NH$_2$, —OH, —OC$_{3-4}$cycloalkyl, —C$_{1-3}$alkyl optionally substituted with 1-3 fluoro, and —OC$_{1-3}$alkyl optionally substituted with phenyl or 1-3 fluoro;

R$^{12}$ is selected from the group consisting of: —CO$_2$R$^{4a}$, —C(O)NR$^7$R$^8$, —N(R$^a$)$_2$, —NR$^b$SO$_p$R$^a$, —NR$^b$C(O)R$^a$, —NR$^b$C(O)NR$^a$R$^b$, —S(O)$_p$NR$^a$R$^b$, —S(O)$_p$R$^a$, —F, —CF$_3$, phenyl, Hetcy and Z$^1$;

R$^{13}$ is selected from the group consisting of —OH, —NH$_2$ and 1-5 of —F;

each R$^a$ is independently selected from the group consisting of
a) —H,
b) —C$_{1-4}$alkyl, —C$_{2-4}$alkenyl and —C$_{2-4}$alkynyl, wherein each is optionally substituted with 1-2 substitutents selected from the group consisting of —OH, —OC$_{1-4}$alkyl, —CN, —NH$_2$, —NHC$_{1-4}$alkyl, and —N(C$_{1-4}$alkyl)$_2$, and —CF$_3$, and optionally with 1-3 of fluoro,
c) Hetcy and Hetcy-C$_{1-4}$alkyl-, the Hetcy moieties being optionally substituted on carton with 1-2 substitutents selected from the group consisting of —F, —OH, —CO$_2$H, —C$_{1-4}$alkyl, —Co$_2$C$_{1-4}$alkyl, —Oc$_{1-4}$alkyl, —NH$_2$, —NHC$_{1-4}$alkyl, —N(C$_{1-4}$alkyl)$_2$, —NHC(O)C$_{1-4}$oxo, —C(O)NHC$_{1-4}$alkyl and —C(O)N(C$_{1-4}$alkyl)$_2$; and optionally substituted on nitrogen when present with a group selected from —C$_{1-4}$alkyl and —C$_{1-4}$acyl; and the alkyl portion of Hetcy-C$_{1-4}$alkyl- being optionally substituted with a member selected from the group consisting of —OH, —CN, —OC$_{1-4}$alkyl, NH$_2$, —NHC$_{1-4}$alkyl, —N(C$_{1-4}$alkyl)$_2$ and 1-3 of fluoro, and
d) Z$^2$ and Z$^2$—C$_{1-4}$alkyl, the alkyl portion of Z$^2$—C$_{1-4}$alkyl- being optionally substituted with substituent selected from the grow consisting of —OH, —CN, —OC$_{1-4}$alkyl, —NH$_2$, NHC$_{1-4}$alkyl, —N(C$_{1-4}$alkyl)$_2$ and 1-3 of fluoro;

each R$^b$ is independently selected from the group consisting of —H and —C$_{1-3}$alkyl optionally substituted with 1-2 members selected from the group consisting of NH$_2$, —OH, —F, —CN and —CF$_3$;

R$^c$, R$^d$, R$^e$ are each independently selected from —H, —F, —Cl, —OH, —CN, —C$_{1-4}$alkyl optionally substituted with 1-3 of fluoro, and —OC$_{1-4}$alkyl optionally substituted with 1-3 of fluoro;

Hetcy is selected from the group consisting of azetidinyl, pyrrolidinyl, piperidinyl, piperazinyl, morpholinyl, tetrahydrofuranyl and β-lactamyl, δ-lactamyl, γ-lactamyl and tetrahydropyranyl;

Z$^1$ is selected from the group consisting of
a) Z$^2$,
b) an 8-membered aromatic or partially unsaturated ortho-fused bicyclic ring system containing 3-5 heteroatoms selected from one sulfur and 2-4 of nitrogen wherein one carbon in the ring is optionally substituted with a group selected from =O, =S, —Sme, —NH$_2$, —CF$_3$, Cl, —C$_{1-4}$alkyl and C$_{1-4}$alkyl substituted with a group selected from —NH$_2$, —OH, —OC$_{1-4}$alkyl, —CN and 1-3 of fluoro, and
c) a 9-membered aromatic or partially unsaturated ortho-fused bicyclic ring system containing 3-4 nitrogen atoms, wherein one carbon in the ring is optionally substituted with a group selected from =O, =S, —SMe, —NH$_2$, —CF$_3$, —Cl, —C$_{1-4}$alkyl and C$_{1-4}$alkyl substituted with a group selected from —NH$_2$, —OH, —OC$_{1-4}$alkyl, —CN and 1-3 of fluoro; and Z$^2$ is selected from the group consisting of:
a) a 5-membered aromatic or partially unsaturated heterocyclic ring containing 2-4 nitrogen atoms, wherein one nitrogen in the ring is optionally substituted with a group selected from —C$_{1-4}$alkyl and —C$_{1-4}$alkyl substituted with a group selected from —NH$_2$, —OH, —CN and 1-3 of fluoro, and one carbon in the ring is optionally substituted with a group selected from =O, =S, —SMe, —NH$_2$, —CF$_3$, —Cl, —C$_{1-4}$alkyl and —C₁₋₄alkyl substituted with a group selected from —NH₂, —OH, —OC₁₋₄alkyl, —CN and 1-3 of fluoro, b) a 5-membered aromatic partially unsaturated heterocyclic ring containing 2-3 heteroatoms selected from one oxygen or one sulfur and 1-2 of nittrogen, wherein one nitrogen in the ring is optionally substituted with a group selected from C₁₋₄alkyl and C₁₋₄alkyl substituted with a group selected from —NH₂, —OH, —CN and 1-3 of fluoro and one carbon in the ring is optionally substituted with a group selected from =O, =S, —SMe, —NH₂, —CF₃, —Cl, and C₁₋₄alkyl optionally substituted with a group selected from —NH₂, —OH, —OC₁₋₄alkyl, —CN and 1-3 of fluoro, and c) a 6-membered aromatic or partially unsaturated heterocyclic ring containing 1-2 nitrogen atoms, wherein one nitrogen in the ring is optionally substituted with a group selected from —C₁₋₄alkyl and —C₁₋₄alkyl substituted with a group selected from —NH₂, —OH, —CN and 1-3 of fluoro, and one carbon in the ring is optionally substituted with a group selected from =O, =S, —SMe, —NH₂, —CF₃, —Cl, —C₁₋₄alkyl and —C₁₋₄alkyl substituted with a group selected from —NH₂, —OH, —OC₁₋₄alkyl, —CN and 1-3 of fluoro.

2. The compound of claim 1 wherein Y is selected from (a) a 5-membered aromatic heterocyclic ring containing 1 to 2 heteroatoms selected from 1 to 2 of N and zero to 1 of S, wherein the heterocyclic ring is optionally substituted with $R^{11}$, and (b) a 6-membered aromatic heterocyclic ring containing 1 to 2 N heteroatoms, wherein the heterocyclic ring is optionally substituted with $R^{11}$.

3. The compound of claim 2 wherein Y is selected from:

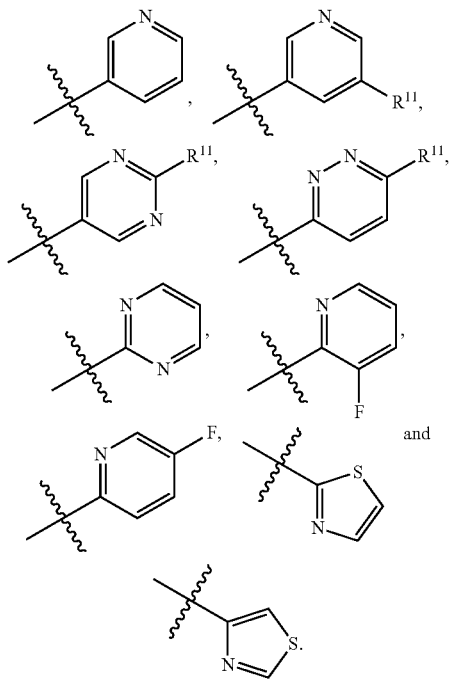

4. The compound of claim 2 wherein $R^2$ is selected from the group consisting of i-propyl, t-butyl, cyclopropyl, cyclobutyl,

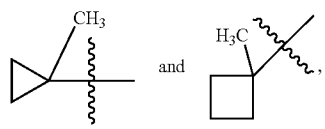

and $R^3$ is selected from the group consisting of —H and —CH₃.

5. The compound of claim 4 wherein $R^1$ is selected from the group consisting of:

(a) a 5-membered aromatic or partially unsaturated heterocyclic ring containing a total of 2 to 4 heteroatoms selected from two to four of N, zero to one of O, and zero to one of S, wherein the heterocyclic ring is optionally substituted with $R^6$, (b) a 6-membered aromatic or partially unsaturated heterocyclic ring containing 1 to 2 heteroatoms selected from N and O, wherein the heterocyclic ring is optionally substituted with $R^6$, (c) —C₁₋₄alkyl optionally substituted with $R^{12}$ and optionally substituted with $R^{13}$, (d) —OR$^{6a}$ wherein R$^{6a}$ is —C₁₋₄alkyl optionally substituted with $R^{13}$, (e) —CO₂C₁₋₆alkyl, (f) —C(O)NR⁷R⁸, (g) —CN, and (h) —C₃₋₆ cycloalkyl optionally substituted with $R^{12}$ and optionally substituted with $R^{13}$.

6. The compound of claim 5 wherein $R^1$ is selected from the group consisting of:

(a) —C(CH₃)₂OH, (b) —C(CH₃)₂NH₂ (c) —C₃₋₆ cycloalkyl optionally substituted with one or more substituents selected from the group consisting of —OH and —NH₂, (d) —OCH₃ optionally substituted with 1-3 of fluoro, (e) —CN, (f) —CO₂C₁₋₆alkyl, and (g) —C(O)NR⁷R⁸ wherein R⁸ is —H and R⁷ is selected from (i) —H, —C₁₋₆alkyl optionally substituted with one or more substituents selected from the group consisting of —F and —OH, (iii) —C₃₋₆ cycloalkyl optionally substituted with one or more substituents selected from the group consisting of —F and —OH, and (iv) a 4-6 membered saturated heterocyclic ring containing one N, wherein the ring is bonded to the nitrogen in —NR⁷R⁸ through a carbon atom in the ring, and wherein the ring is optionally substituted with one or more substituents selected from the group consisting of methyl, —CF₃, —F, —NH₂ and —OH, (h) a 5-membered aromatic or partially unsaturated heterocyclic ring optionally substituted with $R^6$, wherein the ring is selected from:

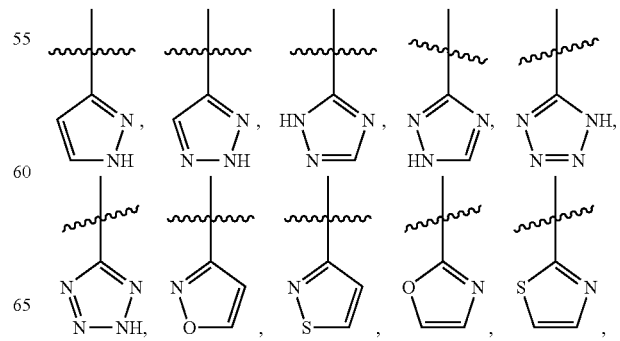

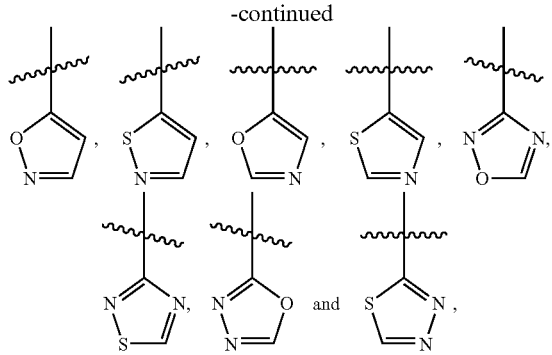

and (i) a 6-membered aromatic heterocyclic ring optionally substituted with $R^6$, wherein the ring is selected from:

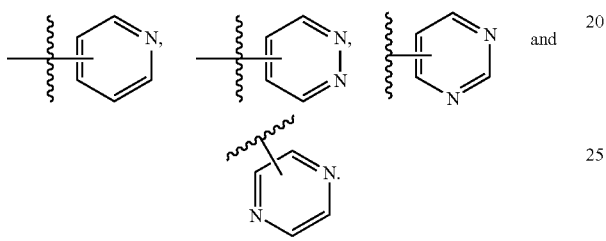

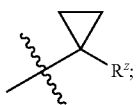

7. The compound of claim 5 wherein R6, when present, is selected from the group consisting of:
(a) —$CR^xR^yR^z$ wherein $R^x$ is selected from —H, —$C_{1-3}$alkyl and —F, $R^y$ is selected from —H, —$C_{1-3}$alkyl and —F, and $R^z$ is selected from —H, —$C_{1-3}$alkyl, —$OC_{1-3}$alkyl, —F, —$NH_2$ and —OH; or $R^x$ and $R^y$ are joined together with the carbon to which they are attached to form a cyclopropyl ring having the following structure

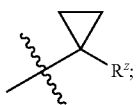

(b) —$C_{1-3}$alkyl-$R^{10}$,
(c) —$R^{10}$,
(d) —$OC_{1-4}$alkyl optionally substituted with 1-5 fluoro,
(e) —$NR^7R^8$,
(f) —$SO_2CH_3$,
(g) oxo and
(h) —$CO_2C_{1-6}$alkyl.

8. The compound of claim 5 wherein $R^{10}$ is selected from

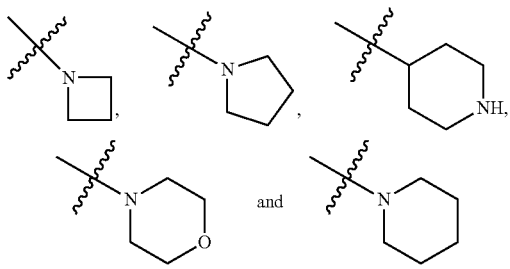

optionally substituted with a substituent selected from methyl, —OH and 1-2 of fluoro.

9. The compound of claim 5 wherein $R^c$, $R^d$ and $R^e$ are each —H.

10. The compound of claim 1 or a pharmaceutically acceptable salt thereof wherein Y is a 6-membered aromatic heterocyclic ring containing 1 to 2 N heteroatoms wherein the heterocyclic ring is optionally substituted with $R^{11}$.

11. The compound of claim 10 wherein Y is selected from:

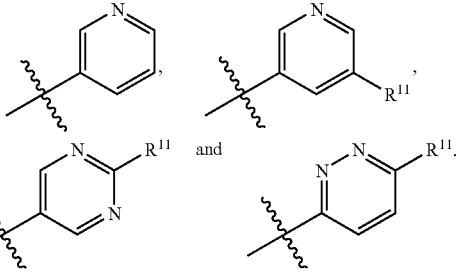

12. The compound of claim 11 wherein $R^2$ is selected from the group consisting of i-propyl, t-butyl, cyclopropyl, cyclobutyl,

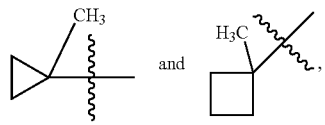

and $R^3$ is selected from the group consisting of —H and —$CH_3$.

13. The compound of claim 12 wherein $R^1$ is selected from the group consisting of:
(a) a 5-membered aromatic or partially unsaturated heterocyclic ring containing a total of 2 to 4 heteroatoms selected from two to four of N, zero to one of O, and zero to one of S, wherein the heterocyclic ring is optionally substituted with $R^6$,
(b) a 6-membered aromatic or partially unsaturated heterocyclic ring containing 1 to 2 heteroatoms selected from N and O, wherein the heterocyclic ring is optionally substituted with $R^6$,
(c) —$C_{1-4}$alkyl optionally substituted with $R^{12}$ and optionally substituted with $R^{13}$,
(d) —$OR^{6a}$ wherein $R^{6a}$ is —$C_{1-4}$alkyl optionally substituted with $R^{13}$, (e) —$CO_2C_{1-6}$alkyl, (f) —$C(O)NR^7R^8$, (g) —CN, and
(h) —$C_{3-6}$ cycloalkyl optionally substituted with $R^{12}$ and optionally substituted with $R^{13}$.

14. A compound selected from the group consisting of:
4-{[3-(6-{1-[4-(5-methoxypyridin-3-yl)phenyl]-1,2-dimethylpropyl}pyridin-3-yl)-1,2,4-oxadiazol-5-yl]methyl}morpholine;
2-[3-(6-{1-[4-(5-methoxypyridin-3-yl)phenyl]-1,2-dimethylpropyl}pyridin-3-yl)-1,2,4-oxadiazol-5-yl]propan-2-ol;
2-{1-[4-(5-methoxypyridin-3-yl)phenyl]-1,2-dimethylpropyl}-5-[5-(piperidin-1-ylmethyl)-1,2,4-oxadiazol-3-yl]pyridine;
5-{5-[(4-fluoropiperidin-1-yl)methyl]-1,2,4-oxadiazol-3-yl}-2-{1-[4-(5-methoxypyridin-3-yl)phenyl]-1,2-dimethylpropyl}pyridine;

2-{1-[4-(5-methoxypyridin-3-yl)phenyl]-1,2-dimethylpropyl}-5-[5-(pyrrolidin-1-ylmethyl)-1,2,4-oxadiazol-3-yl]pyridine;

5-(5-{[(3S)-3-fluoropyrrolidin-1-yl]methyl}-1,2,4-oxadiazol-3-yl)-2-{1-[4-(5-methoxypyridin-3-yl)phenyl]-1,2-dimethylpropyl}pyridine;

5-(5-{[(3R)-3-fluoropyrrolidin-1-yl]methyl}-1,2,4-oxadiazol-3-yl)-2-{1-[4-(5-methoxypyridin-3-yl)phenyl]-1,2-dimethylpropyl}pyridine;

2-[3-(6-{1-[4-(5-methoxypyridin-3-yl)phenyl]-1,2-dimethylpropyl}pyridin-3-yl)-1,2,4-oxadiazol-5-yl]propan-2-amine;

1-[3-(6-{1-[4-(5-methoxypyridin-3-yl)phenyl]-1,2-dimethylpropyl}pyridin-3-yl)-1,2,4-oxadiazol-5-yl]cyclopropanamine;

2-[5-(6-{1-[4-(5-methoxypyridin-3-yl)phenyl]-1,2-dimethylpropyl}pyridin-3-yl)isoxazol-3-yl]propan-2-ol;

2-[6-(6-{1-[4-(5-methoxypyridin-3-yl)phenyl]-1,2-dimethylpropyl}pyridin-3-yl)pyridazin-3-yl]propan-2-ol;

2-{6-[6-(1-{4-[2-(2,5-dimethyl-1H-pyrrol-1-yl)pyrimidin-5-yl]phenyl}-1,2-dimethylpropyl)pyridin-3-yl]pyridazin-3-yl}propan-2-ol;

2-[6-(6-{1-[4-(2-aminopyrimidin-5-yl)phenyl]-1,2-dimethylpropyl}pyridin-3-yl)pyridazin-3-yl]propan-2-ol;

2-[6-(6-{1-[4-(6-aminopyridazin-3-yl)phenyl]-1,2-dimethylpropyl}pyridin-3-yl)pyridazin-3-yl]propan-2-ol;

3-(6-{1-[4-(5-methoxypyridin-3-yl)phenyl]-1,2-dimethylpropyl}pyridin-3-yl)-6-methylpyridazine;

3-(6-{1-[4-(5-methoxypyridin-3-yl)phenyl]-1,2-dimethylpropyl}pyridin-3-yl)-6-(trifluoromethyl)pyridazine;

3-(6-{1-[4-(5-methoxypyridin-3-yl)phenyl]-1,2-dimethylpropyl}pyridin-3-yl)-6-(methyl sulfonyl)pyridazine;

3-[6-(1-{4-[5-(fluoromethoxy)pyridin-3-yl]phenyl}-1,2-dimethylpropyl)pyridin-3-yl]-6-(trifluoromethyl)pyridazine;

3-[6-(1-{4-[5-(difluoromethoxy)pyridin-3-yl]phenyl}-1,2-dimethylpropyl)pyridin-3-yl]-6-(trifluoromethyl)pyridazine;

3-(6-{1-[4-(5-ethoxypyridin-3-yl)phenyl]-1,2-dimethylpropyl}pyridin-3-yl)-6-(trifluoromethyl)pyridazine;

3-[6-(1-{4-[5-(benzyloxy)pyridin-3-yl]phenyl}-1,2-dimethylpropyl)pyridin-3-yl]-6-(trifluoromethyl)pyridazine;

2-(6-{1-[4-(2-aminopyrimidin-5-yl)phenyl]-1,2-dimethylpropyl}pyridin-3-yl)propan-2-ol;

methyl 6-{1-[4-(2-aminopyrimidin-5-yl)phenyl]-1,2-dimethylpropyl}nicotinate;

6-{1-[4-(2-aminopyrimidin-5-yl)phenyl]-1,2-dimethylpropyl}nicotinonitrile;

2-(6-{1-[4-(6-aminopyridazin-3-yl)phenyl]-1,2-dimethylpropyl}pyridin-3-yl)propan-2-ol;

5-(6-{2,2-dimethyl-1-[4-(pyridin-2-ylmethoxy)phenyl]propyl}pyridin-3-yl)-1,3,4-oxadiazol-2-amine;

2-{2,2-dimethyl-1-[4-(pyridin-2-ylmethoxy)phenyl]propyl}-5-(2-methyl-2H-tetrazol-5-yl)pyridine;

2-[3-(6-{1,2-dimethyl-1-[4-(pyridin-2-ylmethoxy)phenyl]propyl}pyridin-3-yl)-1,2,4-oxadiazol-5-yl]propan-2-ol;

1-[3-(6-{1,2-dimethyl-1-[4-(pyridin-2-ylmethoxy)phenyl]propyl}pyridin-3-yl)-1,2,4-oxadiazol-5-yl]cyclopropanamine;

4-{[3-(6-{1,2-dimethyl-1-[4-(pyridin-2-ylmethoxy)phenyl]propyl}pyridin-3-yl)-1,2,4-oxadiazol-5-yl]methyl}morpholine;

3-chloro-6-(6-{1,2-dimethyl-1-[4-(pyridin-2-ylmethoxy)phenyl]propyl}pyridin-3-yl)pyridazine;

6-(6-{1,2-dimethyl-1-[4-(pyridin-2-ylmethoxy)phenyl]propyl}pyridin-3-yl)pyridazine-3-carboxylate;

2-[6-(6-{1,2-dimethyl-1-[4-(pyridin-2-ylmethoxy)phenyl]propyl}pyridin-3-yl)pyridazin-3-yl]propan-2-ol;

2-[3-(6-{1,2-dimethyl-1-[4-(1,3-thiazol-2-ylmethoxy)phenyl]propyl}pyridin-3-yl)-1,2,4-oxadiazol-5-yl]propan-2-ol; and 1-[3-(6-{1,2-dimethyl-1-[4-(1,3-thiazol-2-ylmethoxy)phenyl]propyl}pyridin-3-yl)-1,2,4-oxadiazol-5-yl]cyclopropanamine;

or a pharmaceutically acceptable salts thereof.

15. The compound of claim 1 which is 2-[3-(6-{1-[4-(5-methoxypyridin-3-yl)phenyl]-(1R)-1,2-dimethylpropyl}pyridin-3-yl)-1,2,4-oxadiazol-5-yl]propan-2-ol, or a pharmaceutically acceptable salt thereof.

16. The compound of claim 1 which is 2-[5-(6-{1-[4-(5-methoxypyridin-3-yl)phenyl]-(1R)-1,2-dimethylpropyl}pyridin-3-yl)isoxazol-3-yl]propan-2-ol, or a pharmaceutically acceptable salt thereof.

17. The compound of claim 1 which is 2-[6-(6-{1-[4-(5-methoxypyridin-3-yl)phenyl]-(1R)-1,2-dimethylpropyl}pyridin-3-yl)pyridazin-3-yl]propan-2-ol, or a pharmaceutically acceptable salt thereof.

18. A compound which is 2-[6-(6-{1-[4-(2-aminopyrimidin-5-yl)phenyl]-(1R)-1,2-dimethylpropyl}pyridin-3-yl)pyridazin-3-yl]propan-2-ol, or a pharmaceutically acceptable salt thereof.

19. The compound of claim 1 which is 2-[6-(6-{1-[4-(6-aminopyridazin-3-yl)phenyl]-(1R)-1,2-dimethylpropyl}pyridin-3-yl)pyridazin-3-yl]propan-2-ol, or a pharmaceutically acceptable salt thereof.

20. The compound of claim 1 which is 2-(6-{1-[4-(2-aminopyrimidin-5-yl)phenyl]-(1R)-1,2-dimethylpropyl}pyridin-3-yl)propan-2-ol, or a pharmaceutically acceptable salt thereof.

21. The compound of claim 1 which is 2-(6-{1-[4-(6-aminopyridazin-3-yl)phenyl]-(1R)-1,2-dimethylpropyl}pyridin-3-yl)propan-2-ol, or a pharmaceutically acceptable salt thereof.

22. A pharmaceutical composition comprised of a therapeutically effective amount of a compound of claim 1 and a pharmaceutically acceptable carrier.

23. A method for treatment of asthma comprising administering a therapeutically effective amount of a compound of claim 1 to a patient in need of such treatment.

24. A pharmaceutical composition comprised of a therapeutically effective amount of the compound of claim 18 and a pharmaceutically acceptable carrier.

* * * * *